US012758484B2

(12) United States Patent
Brightman et al.

(10) Patent No.: US 12,758,484 B2
(45) **Date of Patent: *Oct. 13, 2026**

(54) TOPICAL FORMULATIONS OF RECOMBINANT COLLAGENS

(71) Applicant: Geltor, Inc., San Leandro, CA (US)

(72) Inventors: Laura Brightman, Oakland, CA (US); Alexander Lorestani, Oakland, CA (US); Nikolay Ouzounov, San Ramon, CA (US)

(73) Assignee: Geltor, Inc., San Leandro, CA (US)

( * ) Notice: Subject to any disclaimer, the term of this patent is extended or adjusted under 35 U.S.C. 154(b) by 654 days.

This patent is subject to a terminal disclaimer.

(21) Appl. No.: 17/491,228

(22) Filed: Sep. 30, 2021

(65) Prior Publication Data

US 2022/0257492 A1 Aug. 18, 2022

Related U.S. Application Data

(63) Continuation of application No. PCT/US2020/025934, filed on Mar. 31, 2020.

(60) Provisional application No. 62/827,662, filed on Apr. 1, 2019.

(51) Int. Cl.

*A61K 38/39* (2006.01)
*A61K 8/65* (2006.01)
*A61P 17/18* (2006.01)
*A61Q 19/00* (2006.01)
*A61Q 19/08* (2006.01)

(52) U.S. Cl.

CPC .............. *A61K 8/65* (2013.01); *A61Q 19/007* (2013.01); *A61Q 19/08* (2013.01)

(58) Field of Classification Search

CPC ........ A61K 38/39; A61K 8/65; A61K 9/0014; A61P 17/18; A61Q 19/007; A61Q 19/08

See application file for complete search history.

(56) References Cited

U.S. PATENT DOCUMENTS 4,515,893 A 5/1985 Kung et al.
4,816,397 A 3/1989 Boss et al.
4,816,567 A 3/1989 Cabilly et al.
4,946,778 A 8/1990 Ladner et al.
5,091,313 A 2/1992 Chang
5,602,183 A 2/1997 Martin et al.
5,622,700 A 4/1997 Jardieu et al.
5,672,347 A 9/1997 Aggarwal et al.
5,693,762 A 12/1997 Queen et al.
5,714,338 A 2/1998 Wai Fei et al.
5,721,108 A 2/1998 Robinson et al.
5,725,856 A 3/1998 Hudziak et al.
5,736,137 A 4/1998 Anderson et al.
6,413,742 B1 7/2002 Olsen et al.
6,428,978 B1 8/2002 Olsen et al.
6,617,431 B1 9/2003 Gruber et al.
6,653,450 B1 11/2003 Berg et al.
6,682,760 B2 1/2004 Noff et al.
6,903,200 B1 * 6/2005 Chou .................... C07H 21/02 435/325
6,992,172 B1 1/2006 Chang et al.
7,125,837 B1 10/2006 Keating et al.
7,229,788 B1 6/2007 Weiss
7,495,076 B2 2/2009 Gu et al.
7,700,126 B2 4/2010 Ng et al.
7,754,447 B2 7/2010 Glover et al.
7,759,090 B2 7/2010 Chou et al.
7,803,577 B2 9/2010 Weiss
7,932,053 B2 4/2011 Bank et al.
7,932,353 B2 4/2011 Van Es et al.
8,252,553 B2 8/2012 Hook et al.
8,507,652 B2 8/2013 Da Cruz
8,618,250 B2 12/2013 Russell et al.
8,759,487 B2 6/2014 Shoseyov et al.
8,889,626 B2 11/2014 Lin et al.
8,956,632 B2 2/2015 Boutros
9,040,484 B2 5/2015 Marinkovich et al.
9,072,724 B2 7/2015 Hausmanns et al.
9,156,950 B2 10/2015 Garralda et al.
9,328,154 B2 5/2016 Chilkoti
9,382,310 B2 7/2016 Mirochnitchenko et al.
9,591,853 B2 3/2017 Belgorodsky et al.
9,675,635 B2 6/2017 Minatelli et al.
9,676,837 B2 6/2017 Viswanathan et al.
9,725,498 B2 8/2017 Russell et al.
9,962,582 B2 5/2018 Antku
10,053,501 B2 8/2018 Ramshaw et al.
10,155,793 B2 12/2018 Ramshaw et al.

(Continued)

FOREIGN PATENT DOCUMENTS

CN 1403479 A 3/2003
CN 1422280 A 6/2003

(Continued)

OTHER PUBLICATIONS

A0A158RFW1 from UniProt, pp. 1-6, Integrated into UniProtKB/TrEMBL on Jun. 8, 2016. (Year: 2016).*
Yampolsky et al., "The Exchangeability of Amino Acids in Proteins," Genetics, 2005, 170: 1459-1472. (Year: 2005).*
Pai et al. Topical peptides as cosmeceuticals. Indian Journal of Dermatology, Venereology, and Leprology, vol. 83, Issue 1, pp. 9-18 (Jan.-Feb. 2017).
U.S. Appl. No. 17/493,598 Office Action dated Nov. 21, 2023.
U.S. Appl. No. 17/532,978 Office Action dated Dec. 22, 2023.
Zhuang, et al. Effects of collagen and collagen hydrolysate from jellyfish umbrella on histological and immunity changes of mice photoaging. Nutrients. vol. 5 (2013): 223-233.
Co-pending U.S. Appl. No. 18/191,556, inventors Co; Julia et al., filed Mar. 28, 2023.

(Continued)

*Primary Examiner* — Julie Ha

(74) *Attorney, Agent, or Firm* — Casimir Jones, S.C.; Rikki A. Hullinger

(57) ABSTRACT

Methods of improving firmness, elasticity, brightness, hydration, tactile texture or visual texture of skin are described herein. In some aspects, the methods comprise topically applying non-naturally occurring truncated collagen molecules to skin.

12 Claims, 13 Drawing Sheets

Specification includes a Sequence Listing.

(56) References Cited

U.S. PATENT DOCUMENTS

| | | | |
|---|---|---|---|
| 10,232,008 B1 | 3/2019 | Moran | |
| 10,358,464 B2 | 7/2019 | Hook et al. | |
| 10,941,406 B2 | 3/2021 | Ouzounov | |
| 11,028,148 B2 | 6/2021 | Ouzounov et al. | |
| 11,041,015 B2 | 6/2021 | Ouzounov et al. | |
| 11,168,126 B2 | 11/2021 | Ouzounov et al. | |
| 11,174,300 B2 | 11/2021 | Ouzounov et al. | |
| 11,180,541 B2 | 11/2021 | Ouzounov et al. | |
| 11,214,609 B2 * | 1/2022 | Ouzounov | A61K 38/39 |
| 11,332,505 B2 | 5/2022 | Ouzounov et al. | |
| 2002/0132753 A1 | 9/2002 | Rosen et al. | |
| 2008/0200409 A1 | 8/2008 | Wilson et al. | |
| 2010/0209940 A1 | 8/2010 | Veidal et al. | |
| 2013/0078209 A1 | 3/2013 | Yu et al. | |
| 2013/0237486 A1 | 9/2013 | Bella | |
| 2014/0200531 A1 | 7/2014 | Jordan et al. | |
| 2014/0309401 A1 | 10/2014 | Hayashida et al. | |
| 2015/0150764 A1 | 6/2015 | Pinsky | |
| 2016/0130315 A1 | 5/2016 | Kim et al. | |
| 2016/0215018 A1 | 7/2016 | Yang et al. | |
| 2018/0282776 A1 | 10/2018 | Douchin et al. | |
| 2019/0106702 A1 | 4/2019 | Ouzounov | |
| 2019/0153068 A1 * | 5/2019 | Ouzounov | A61Q 19/08 |
| 2019/0276515 A1 | 9/2019 | Bruno-Bonnet et al. | |
| 2020/0009184 A1 | 1/2020 | Akthakul et al. | |
| 2020/0184381 A1 | 6/2020 | Persikov et al. | |
| 2020/0255497 A1 | 8/2020 | Ouzounov et al. | |
| 2022/0127333 A1 | 4/2022 | Ouzounov et al. | |
| 2022/0281954 A1 | 9/2022 | Ouzounov et al. | |
| 2022/0332775 A1 | 10/2022 | Ouzounov et al. | |

FOREIGN PATENT DOCUMENTS

| | | | |
|---|---|---|---|
| CN | 1653087 | A | 8/2005 |
| CN | 1793177 | A | 6/2006 |
| CN | 101311193 | A | 11/2008 |
| CN | 101311196 | A | 11/2008 |
| CN | 101374859 | A | 2/2009 |
| CN | 102471769 | A | 5/2012 |
| CN | 103897057 | A | 7/2014 |
| CN | 104313053 | A | 1/2015 |
| CN | 104667335 | A | 6/2015 |
| CN | 106554410 | A | 4/2017 |
| CN | 107586332 | A | 1/2018 |
| CN | 109350555 | A | 2/2019 |
| CN | 111388404 | A | 7/2020 |
| CN | 111417404 | A | 7/2020 |
| EP | 0036776 | A2 | 9/1981 |
| EP | 0535446 | A1 | 4/1993 |
| EP | 0420937 | B1 | 11/1994 |
| EP | 1323820 | A2 | 7/2003 |
| EP | 2941277 | B1 | 9/2018 |
| EP | 3395860 | A1 | 10/2018 |
| JP | 2003137807 | A | 5/2003 |
| JP | 2003516730 | A | 5/2003 |
| JP | 2003277399 | A | 10/2003 |
| JP | 2006151847 | A | 6/2006 |
| JP | 2013095708 | A | 5/2013 |
| JP | 2016124798 | A | 7/2016 |
| JP | 2017523780 | A | 8/2017 |
| JP | 2020535812 | A | 12/2020 |
| KR | 20020059719 | A | 7/2002 |
| KR | 20160093739 | A | 8/2016 |
| KR | 20180056237 | A | 5/2018 |
| KR | 20190024916 | A | 3/2019 |
| TW | 200517398 | A | 6/2005 |
| WO | WO-9304173 | A1 | 3/1993 |
| WO | WO-9404690 | A1 | 3/1994 |
| WO | WO-9519181 | A1 | 7/1995 |
| WO | WO-9523865 | A1 | 9/1995 |
| WO | WO-9630046 | A1 | 10/1996 |
| WO | WO-9640210 | A1 | 12/1996 |
| WO | WO-9726912 | A2 | 7/1997 |
| WO | WO-9738710 | A1 | 10/1997 |
| WO | WO-9806248 | A2 | 2/1998 |
| WO | WO-9823761 | A1 | 6/1998 |
| WO | WO-9845331 | A2 | 10/1998 |
| WO | WO-9851793 | A1 | 11/1998 |
| WO | WO-9903886 | A1 | 1/1999 |
| WO | WO-0009018 | A1 | 2/2000 |
| WO | WO-0075348 | A1 | 12/2000 |
| WO | WO-0140309 | A2 | 6/2001 |
| WO | WO-2004056312 | A2 | 7/2004 |
| WO | WO-2005021772 | A1 | 3/2005 |
| WO | WO-2005094868 | A1 | 10/2005 |
| WO | WO-2008000445 | A1 | 1/2008 |
| WO | WO-2009134511 | A1 | 11/2009 |
| WO | WO-2010071938 | A1 | 7/2010 |
| WO | WO-2011008904 | A1 | 1/2011 |
| WO | WO-2012063088 | A2 | 5/2012 |
| WO | WO-2015012682 | A2 | 1/2015 |
| WO | WO-2015012683 | A1 | 1/2015 |
| WO | WO-2015020982 | A2 | 2/2015 |
| WO | WO-2016004334 | A1 | 1/2016 |
| WO | WO-2017083398 | A1 | 5/2017 |
| WO | WO-2017125585 | A2 | 7/2017 |
| WO | WO-2017156418 | A1 | 9/2017 |
| WO | WO-2017160636 | A1 | 9/2017 |
| WO | WO-2017125585 | A9 | 10/2017 |
| WO | WO-2017172994 | A1 | 10/2017 |
| WO | WO-2017206326 | A1 | 12/2017 |
| WO | WO-2018014453 | A1 | 1/2018 |
| WO | WO-2018041684 | A1 | 3/2018 |
| WO | WO-2018078276 | A1 | 5/2018 |
| WO | WO-2018119530 | A1 | 7/2018 |
| WO | WO-2018144093 | A2 | 8/2018 |
| WO | WO-2019023555 | A1 | 1/2019 |
| WO | WO-2019046943 | A1 | 3/2019 |
| WO | WO-2019068018 | A2 | 4/2019 |
| WO | WO-2019077312 | A1 | 4/2019 |
| WO | WO-2019099561 | A1 | 5/2019 |
| WO | WO-2019166418 | A1 | 9/2019 |
| WO | WO-2020094728 | A1 | 5/2020 |
| WO | WO-2020205848 | A1 | 10/2020 |
| WO | WO-2020210440 | A1 | 10/2020 |
| WO | WO-2022072696 | A1 | 4/2022 |

OTHER PUBLICATIONS

EP20781827.9 Extended European Search Report dated Jun. 6, 2023.

Homayouni-Tabrizi et al. Cytotoxic and antioxidant capacity of camel milk peptides: Effects of isolated peptide on superoxide dismutase and catalase gene expression. Journal of Food and Drug Analysis 25 (2017) 567-575. Available online Dec. 7, 2016.

Katayama et al. Regulation of extracellular matrix production by chemically synthesized subfragments of type I collagen carboxy propeptide. Biochemistry 1991, 30, 7097-7104.

PCT/US2021/052966 International Search Report and Written Opinion dated Dec. 10, 2021.

U.S. Appl. No. 17/493,598 Office Action dated May 11, 2023.

U.S. Appl. No. 17/532,978 Office Action dated May 25, 2023.

Amino acid sequence of SEQ ID No. 572 in US20130237486A1, pp. 1-2, accessed Jul. 15, 2020 at URL: http://seqdata.uspto.gov/?pageRequest=viewSequence&DocID=US20130237486A1&seqID=572. United States Patent and Trademark Office Publication Site for Issued and Published Sequences (PSIPS).

Anonymous, "CoIF1—Fibrillar collagen—Podocoryna carnera (Hydrozoan)—coIF1 gene & protein" (Jan. 1, 1998), XP055541622, Retrieved from the Internet: URL:https://www.uniportorg/uniport/076966#entry_information [retrieved on Jan. 14, 2019].

Blast search results for SEQ ID No. 76, pp. 1-24 (accessed Jun. 28, 2021).

Bochicchio et al., Investigating the Role of (2S,4r)-4-Hydroxyproline in Elastin Model Peptides. Biomacromolecules 14: 4278-4288 (2013).

Bornert, Olivier et al. "Analysis of the functional consequences of targeted exon deletion in COL7A1 reveals prospects for dystrophic epidermolysis bullosa therapy", Molecular Therapy. Jul. 1, 2016;24(7):1302-11.

(56) References Cited

OTHER PUBLICATIONS

Bornhorst JA, Falke JJ. [16] Purification of proteins using polyhistidine affinity tags. In Methods in enzymology Jan. 1, 2000 (vol. 326, pp. 245-254). Academic Press.
Brown-Augsburger et al., Identification of an Elastin Cross-linking Domain that Joins Three Peptide Chains. Journal of Biological Chemistry 270(30): 17778-17783 (1995).
Cayley, D. Scott, et al., "Biophysical characterization of changes in amounts and activity of *Escherichia coli* cell and compartment water and turgor pressure in response to osmotic stress", Biophysical Journal, (Apr. 2000), 78(4):1748-1764.
Chandrakasan et al. Preparation of intact monomeric collagen from rat tail tendon and skin and the structure of the nonhelical ends in solution. J Biol Chem. Oct. 10, 1976;251(19):6062-7.
Chou, M-Y, et al., "Genomic organization and characterization of the human type XXI collagen (COL21A1) gene", Genomics. Mar. 1, 2002;79(3):395-401.
Chu et al. Multiexon deletion in an osteogenesis imperfecta variant with increased type III collagen mRNA. J Biol Chem. Jan. 25, 1985;260(2):691-4.
Collagen, type XXI, alpha 1, isoform CRA_e [*Homo sapiens*], from https://www.ncbi.nlm.nih.gov/protein/EAX04452.1?report=genbank &log$=protalign&blast_rank=1&RID=GVNGXK5R01 R, p. 1-3, accessed Jul. 14, 2020. Record created Dec. 18, 2006.
Co-pending U.S. Appl. No. 17/532,978, inventors Ouzounov; Nikolay et al., filed Nov. 22, 2021.
Definition of Serum by Merriam-Webster, from https://www.merriam-webster.com/dictionary/serum, pp. 1-12, accessed Apr. 18, 2019.
Dinh et al. Using superfolder green fluorescent protein for periplasmic protein localization studies. J Bacteriol 193(18):4984-4987 (Sep. 2011). Epub Jul. 15, 2011. doi: 10.1128/JB.00315-11.
Drumm et al. Genetic Variation and Clinical Heterogeneity in Cystic Fibrosis. Annu Rev Pathol. 2012; 7: 267-282. Published online Oct. 17, 2011. doi: 10.1146/annurev-pathol-011811-120900.
Dulbecco's Modified Eagle Medium (DMEM). Product Information. Product Code: AT068. HiMedia Laboratories Pvt Ltd., Mumbai, India. 2011. 2 pages.
EP20186437.8 Extended European Search Report dated Jan. 22, 2021.
Fleischmajer et al. Rotary shadowing of collagen monomers, oligomers, and fibrils during tendon fibrillogenesis. J Histochem Cytochem. Jan. 1991;39(1):51-8.
GenBank Accession No. AJ009690. Version No. AJ009690.1. Podocoryne carnea mRNA for fibrillar collagen, partial. Record created Jul. 30, 1988. 2 pages. Retrieved Mar. 26, 2020 at URL: https://www.ncbi.nlm.nih.gov/nucleotide/3355656?report=genbank &log$=nuclalign&blast_rank=1&RID= TSYP7CMV014.
GenBank Accession No. CAA08789. Version No. CAA08789.1. fibrillar collagen, partial [Podocoryna carnea]. Record created Mar. 9, 1999. 2 pages. Retrieved Apr. 28, 2020 at URL: https://www.ncbi.nlm.nih.gov/protein/4379341?report=genbank&log$= protalign&blast_rank=1&RID=T1N9ZEUW014.
GenBank Accession No. XP_016874317. Version No. XP_016874317. 1. collagen alpha-1(II) chain isoform X1 [*Homo sapiens*]. Record created Jun. 6, 2016. 3 pages. Accessed Jun. 18, 2020 at URL: https://www.ncbi.nlm.nih.gov/protein/XP_016874317.1?report= genbank&log$=protalign&blast_rank=11&RID= ER8N7H11014.
Gortz, H.-D. et al., "Changes in Fine Structure and Polypeptide Pattern during Development of Holospora obtuse, a bacterium Infecting the macronucleus of Paramecium caudatum", Journal of Bacteriology, (Oct. 1, 1990), 172(10):5664-5669, XP055373233, Retrieved from the Internet: URL: https://www.ncbi.nlm.nih.gov/pmc/articles/PMC526880/pdf/jbacter00164-0156.pdf, [retrieved May 16, 2017].
Grosso et al. PGAIPG, a Repeated Hexapeptide of Bovine Tropoelastin, Is a Ligand for the 67-kDa Bovine Elastin Receptor. Matrix. Mar. 1993;13(2):157-64. doi: 10.1016/s0934-8832(11)80074-0.
Gumpert et al. Characteristic properties and biological significance of stable protoplast type L-forms. In Protoplasts, Lecture Proceedings of the 6th International Protoplast Symposium: Basel. Experientia 1983, 46(suppl):227-241.
Haworth, R.S. et al., "Uncoupler resistance in *E. coli* Tuv and Cuv is due to the exclusion of uncoupler by the outer membrane", Biochim Biophys Acta., (Aug. 9, 1990), 1019(1):67-72, XP023349580, ISBN: 0005-2728, DOI: 10.1016/0005-2728(90)90125-N [retrieved on Aug. 9, 1990]. Abstract only.
Hoischen et al. Lipid and fatty acid composition of cytoplasmic membranes from Streptomyces hygroscopicus and its stable protoplast-type L form. J Bacteriol 179(11):3430-3436 (Jun. 1997).
Hong et al., Fibrillar Type I Collagen Enhances the Differentiation and Proliferation of Myofibroblasts by Lowering alpha2beta1 Integrin Expression in Cardiac Fibrosis. Biomed Res Int. 2017; 2017: 1790808. Published online Jan. 30, 2017. doi: 10.1155/2017/1790808. 11 pages.
International Preliminary Report on Patentability, dated Oct. 2, 2018, for International Patent Application No. PCT/US2017/024857.
International Search Report and Written Opinion of the Searching Authority for International Patent Application No. PCT/US2017/024857, dated May 31, 2017.
International Search Report and Written Opinion of the Searching Authority for International Patent Application No. PCT/US2018/053601, dated Apr. 10, 2019.
Joly et al. Chapter 20: Practical Applications for Periplasmic Protein Accumulation, in The Periplasm, ed. Ehrmann, M., ASM Press, Washington D.C., pp. 345-360 (2007).
Krapf et al. Deciphering the aggregation mechanism of bacteria (Shewanella oneidensis MR1) in the presence of polyethyleneimine: Effects of the exopolymeric superstructure and polymer molecular weight. Colloids Surf B Biointerfaces. Mar. 1, 2016;139:285-93. doi: 10.1016/j.colsurfb.2015.12.015. Epub Dec. 8, 2015.
Kuzan et al. An Estimation of the Biological Properties of Fish Collagen in an Experimental In Vitro Study. Adv Clin Exp Med. May-Jun. 2015;24(3):385-92. doi: 10.17219/acem/31704.
Lucas et al. A molecular, morphometric and mechanical comparison of the structural elements of byssus from Mytilus edulis and Mytilus galloprovincialis. J Exp Biol. Jun. 2002;205(Pt 12):1807-17.
Luo et al. Collagen-like peptides and peptide-polymer conjugates in the design of assembled materials. Eur Polym J. Oct. 2013; 49(10): 2998-3009. doi: 10.1016/j.eurpolymj.2013.05.013. Available online Jun. 4, 2013.
Paul-Dauphin et al. Bias and precision in visual analogue scales: a randomized controlled trial. Am J Epidemiol. Nov. 15, 1999;150(10):1117-27.
PCT/US2020/025934 International Search Report and Written Opinion dated Jul. 2, 2020.
PCT/US2020/027399 International Search Report and Written Opinion dated Jun. 26, 2020.
Peptidecutter of SEQ ID No. 4 in Chou et al., from https://web.expasy.org/cgi-bin/peptide_cutter/peptidecutter.ol, pp. 1-8, accessed Jan. 29, 2021.
Phosphate buffered saline. Protocols Online (Oct. 3, 2016). Retrieved Aug. 7, 2020 from URL: https://www.protocolsonline.com/recipes/phosphate-buffered-saline-pbs/. 3 pages.
Pilizota, Teuta and J. W. Shaevitz, "Fast, Multiphase vol. Adaptation to Hyperosmotic Shock by *Escherichia coli*", PLoS ONE, (Apr. 2012), 7(4): e35205. https://doi.org/10.1371/journal.pone.0035205.
Protease cleavage of SEQ ID No. 61 in WO 2019/068018A2, from ExPASy-PeptideCutter, SIB Swiss Institute of Bioinformatics, accessed Oct. 15, 2020 at URL: https://web.expasy.org/cgi-bin/peptide_cutter/peptidecutter.p1, pp. 1-2.
Ramshaw, John A. M., et al., "Gly-XY tripeptide frequencies in collagen: a context for host-guest triple-helical peptides", Journal of structural biology. Jan. 1, 1998;122(1-2):86-91.
Rodriguez et al. Collagen: A Review on Its Sources and Potential Cosmetic Applications. J Cosmet Dermatol. Feb. 2018;17(1):20-26. doi: 10.1111/jocd.12450. Epub Nov. 16, 2017.

(56) References Cited

OTHER PUBLICATIONS

Schmid, V. et al., "The extracellular matrix (mesoglea) of hydrozoan jellyfish and its ability to support cell adhesion and spreading", In Hydrobiologia Jun. 1, 1991 (vol. 216, No. 1, pp. 3-10). Kluwer Academic Publishers.
Schrader et al., Elastin is heterogeneously cross-linked. J Biol Chem 293(39): 15107-15119 (2018).
Sewing et al. Jellyfish collagen matrices conserve the chondrogenic phenotype in two- and three-dimensional collagen matrices. J Tissue Eng Regen Med. Mar. 2017;11(3):916-925. doi: 10.1002/term.1993. Epub Jan. 29, 2015.
Shigemura et al. Effect of Prolyl-hydroxyproline (Pro-Hyp), a food-derived collagen peptide in human blood, on growth of fibroblasts from mouse skin. J Agric Food Chem. Jan. 28, 2009;57(2):444-9. doi: 10.1021/jf802785h.
Shin et al. Enhancement of the Tumor Penetration of Monoclonal Antibody by Fusion of a Neuropilin-Targeting Peptide Improves the Antitumor Efficacy. Mol Cancer Ther 13(3):651-661, with supplementary information pp. 1-27 (Mar. 2014).
Teale et al., Ultraviolet fluorescence of the aromatic amino acids. Biochem J. 65(3):476-482 (1957).
Tomaro-Duchesneau et al. Microencapsulation for the Therapeutic Delivery of Drugs, Live Mammalian and Bacterial Cells, and Other Biopharmaceutics: Current Status and Future Directions. J Pharm (Cairo) 2013:103527 (2013). Published online Dec. 4, 2012. doi: 10.1155/2013/103527.
Tris buffer, from http://cshprotocols.cshlp.org/content/2011/2/pdb.rec12394.full, pp. 1-2, accessed Nov. 16, 2020.
Turczynski et al., Targeted Exon Skipping Restores Type VII Collagen Expression and Anchoring Fibril Formation in an In Vivo RDEB Model. Journal of Investigative Dermatology 136: 2387-2395 (2016).
U.S. Appl. No. 16/144,914 Final Office Action dated Feb. 5, 2021.
U.S. Appl. No. 16/839,035 Non-Final Office Action dated Jul. 7, 2021.
U.S. Appl. No. 16/839,035 Non-Final Office Action dated Nov. 27, 2020.
U.S. Appl. No. 16/839,042 Final Office Action dated Dec. 3, 2020.
U.S. Appl. No. 16/839,042 Notice of Allowance dated Apr. 16, 2021.
U.S. Appl. No. 16/839,042 Notice of Allowance dated Feb. 8, 2021.
U.S. Appl. No. 16/839,044 Final Office Action dated Dec. 10, 2020.
U.S. Appl. No. 16/839,047 Notice of Allowance dated Feb. 23, 2021.
U.S. Appl. No. 16/844,226 Final Office Action dated Feb. 4, 2021.
U.S. Appl. No. 16/144,914 Notice of Allowance dated Sep. 1, 2021.
U.S. Appl. No. 16/144,914 Office Action dated Jul. 10, 2020.
U.S. Appl. No. 16/839,035 Notice of Allowance dated Oct. 26, 2021.
U.S. Appl. No. 16/839,035 Office Action dated Jul. 24, 2020.
U.S. Appl. No. 16/839,042 Office Action dated Aug. 24, 2020.
U.S. Appl. No. 16/839,044 Office Action dated Aug. 7, 2020.
U.S. Appl. No. 16/839,047 Office Action dated Oct. 21, 2020.
U.S. Appl. No. 16/844,226 Notice of Allowance dated Sep. 16, 2021.
U.S. Appl. No. 16/844,226 Office Action dated Oct. 29, 2020.
Water, from http://www.biology-online.org/dictionary/Water, accessed Apr. 24, 2014, 3 pages.
What Is Sorbic Acid? From https://www.healthline.com/health/food-nutrition/what-is-sorbic-acid, accessed Sep. 9, 2019, 3 pages.
Willing et al. Heterozygosity for a large deletion in the alpha 2(I) collagen gene has a dramatic effect on type I collagen secretion and produces perinatal lethal osteogenesis imperfecta. J Biol Chem. Jun. 15, 1988;263(17):8398-404.
Woodley et al., Intravenously Injected Recombinant Human Type VII Collagen Homes to Skin Wounds and Restores Skin Integrity of Dystrophic Epidermolysis Bullosa. Journal of Investigative Dermatology 133: 1910-1913 (2013).
Yampolsky et al. The Exchangeability of Amino Acids in Proteins. Genetics. Aug. 2005; 170(4): 1459-1472. doi: 10.1534/genetics.104.039107.
Zhuang et al. Effects of Collagen and Collagen Hydrolysate From Jellyfish (*Rhopilema esculentum*) on Mice Skin Photoaging Induced by UV Irradiation. J Food Sci. Aug. 2009;74(6):H183-8. doi: 10.1111/j.1750-3841.2009.01236.x.
EBI Accession No. USPOP:ABL21271. Database Accession No. ABL21271. EMBL-EBI. Retrieved Feb. 14, 2023 at https://www.ebi.ac.uk/Tools/dbfetch/. One page.
EBI Accession No. USPOP:ABU27708. Database Accession No. ABU27708. EMBL-EBI. Retrieved Feb. 14, 2023 at https://www.ebi.ac.uk/Tools/dbfetch/. 2 pages.
EP20787564.2 Extended European Search Report dated Dec. 23, 2022.
Genbank: "Collagen Alpha-1(XXI) Chain Isoform B Precursor [*Homo sapiens*]," Accession No. NP_001305681, Version No. NP_001305681.1, Record created Jan. 14, 2016, 3 pages, [Retrieved on Mar. 22, 2024] Retrieved from URL: https://www.ncbi.nlm.nih.gov/protein/NP_001305681.1/.
Genbank: "Collagen, Type XXI, Alpha 1, Isoform CRA_d [*Homo sapiens*]," GenBank, Accession No. EAX04451, Version No. EAX04451.1, Record created Dec. 18, 2006, 2 pages, [Retrieved Mar. 22, 2024] Retrieved from URL: https://www.ncbi.nlm.nih.gov/protein/EAX04451.1?report=genbank&log$=protalign&blast_rank=2&RID=WP6DGNX7013.
Genbank: "Fibrillar Collagen, Partial [Podocoryna carnea]," GenBank, Accession No. CAA08789, pp. 1-2, [Retrieved on Jul. 25, 2016] Retrieved from URL: https://www.ncbi.nlm.nih.gov/protein/CAA08789.1?report=genbank&log$=protalign&bla.
Lee J-H., et al., "Development of Screening Method for the Soluble Recombinant Protein Using B-Lactamase as a Fusion Partner," Korean Chemical Engineering Research, Oct. 2009, vol. 47, No. 5, pp. 624-629, with English abstract.
Wikipedia: "Green Fluorescent Protein," Wikipedia, 10 pages, [Retrieved on Mar. 22, 2024] Retrieved from URL: https://en.wikipedia.org/wiki/Green_fluorescent_protein.

* cited by examiner

SKIN COLLAGEN INCREASE

93% of subjects showed improvement.

Viability after urban dust exposure relative to untreated control

UVB induced inflammation
% IL-1a compared to untreated

Lines/Wrinkles (Global)*

0 cm
None 10 cm
Numerous lines/
Wrinkles – Severe,Deep

Firmness (Visual)

0 cm
Firm, Tight
appearance 10 cm
Loose appearance

Elasticity (Tactile)

0 cm
Good stretch and
recoil properties 10 cm
Poor stretch and
recoil properties Brightness 0 cm
Light/Bright
appearance 10 cm
Dark, ashen Texture/Softness (tactile)

0 cm
Smooth, soft
surface feel 10 cm
Rough, coarse
surface feel

Texture/Smoothness (visual)

0 cm
Smooth, even
surface appearance 10 cm
Rough, uneven
surface appearance

* Inclusion Criteria

FIG. 18

TOPICAL FORMULATIONS OF RECOMBINANT COLLAGENS

CROSS-REFERENCE

This application is a continuation application of International Application No. PCT/US2020/025934, filed Mar. 31, 2020, which claims the benefit of U.S. Provisional Application No. 62/827,662, filed Apr. 1, 2019, which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created Sep. 28, 2021, is named 57607_705_301_SL.txt and is 87,683 bytes in size.

BACKGROUND

Collagens and similar proteins are the most abundant proteins in the biosphere. Collagens are structural proteins found in the skin, connective tissue, and bones of animals and other tissues. In humans, the amount of collagen present in the body is approximately one third of the total proteins and accounts for about three fourths of the dry weight of skin.

The structure of natural collagen can be a triple helix in which three polypeptide strands together form a helical coil. The individual polypeptide strands are composed of repeating triplet amino acid sequences designated as GLY-X-Y. X and Y can be any amino acid and the first amino acid is glycine. The amino acids proline and hydroxyproline are found in high concentrations in collagen. The most common triplet is glycine-proline-hydroxyproline (Gly-Pro-Hyp) accounting for approximately 10.5% of the triplets in collagen.

Gelatin is a product obtained by partial hydrolysis of certain (e.g., natural) collagen. Typically, gelatin is produced by acid hydrolysis, alkaline hydrolysis, and enzymatic hydrolysis or by exposing collagen to heat in an aqueous solution (e.g., boiling the bones and skins of animal, boiling fish scales, etc.).

Gelatin is used in many products including cosmetics, foods, pharmaceuticals, medical devices, photographic films, adhesives, binders, and many others. The physical and chemical properties of gelatin are tuned to the particular application. These physical/chemical properties include gel strength, melting point temperature, viscosity, color, turbidity, pH, isoelectric point, and others.

SUMMARY

In certain embodiments here are various polypeptides, compositions comprising such polypeptides, and methods of using such polypeptides and/or compositions thereof. In certain embodiments, such polypeptides comprise non-natural and/or recombinant polypeptides, such as comprising one or more amino acid sequence that is truncated relative to a natural collagen, such as a natural collagen described herein. In certain instances, such polypeptides are described herein as a "truncated collagen". In specific embodiments, the polypeptide comprises one or more (e.g., two or more) truncated amino acid sequences of a natural human collagen. In other specific embodiments, the polypeptide comprises one or more (e.g., two or more) truncated amino acid sequences of a natural jellyfish collagen. In one aspect, a method of providing a benefit to (e.g., increasing the firmness, elasticity, brightness, hydration, tactile texture, or visual texture of) skin (such as skin of an individual, such as a human) is provided. The method in some embodiments comprises topically applying a polypeptide described herein (e.g., a non-naturally occurring truncated collagen, such as described herein) or a formulation (e.g., that comprises a polypeptide, such as a non-naturally occurring truncated collagen) to the skin.

In a specific aspect, a method of decreasing lines or wrinkles present on skin or decreasing erythema of skin is provided. The method in some embodiments comprises topically applying a polypeptide described herein (e.g., a non-naturally occurring truncated collagen, such as described herein), or a formulation thereof, to the skin. In some embodiments, also provided herein is a formulation comprising a polypeptide described herein, such as a non-naturally occurring truncated collagen.

In certain instances, a polypeptide (e.g., a truncated collagen) described herein is useful in or for increasing the firmness, elasticity, brightness, hydration, tactile texture, and/or visual texture of skin. In some instances, a polypeptide (e.g., a truncated collagen) described herein is useful in or for decreasing lines or wrinkles present on skin or decreasing erythema of skin. In specific embodiments, the polypeptide (e.g., truncated collagen) is or comprises a truncated jellyfish collagen (e.g., a truncated amino acid sequence of a naturally occurring jellyfish collagen). In other specific embodiments, the polypeptide (e.g., truncated collagen) is or comprises a truncated human collagen (e.g., a truncated amino acid sequence of a naturally occurring human collagen).

In some embodiments, the polypeptide (e.g., truncated collagen) (e.g., useful in the methods disclosed herein) is or comprises a truncated amino acid sequence relative to a natural (e.g., human or jellyfish (Hydrozoan)) collagen. In some instances, such a polypeptide is referred to herein as a non-naturally occurring collagen. In specific embodiments, the non-naturally occurring collagen is or comprises an amino acid sequence of SEQ ID NO: 2, SEQ ID NO: 4, SEQ ID NO: 5, SEQ ID NO: 7, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 25, SEQ ID NO: 27, and/or SEQ ID NO: 29, or a homolog thereof (e.g., having at least 85%, at least 90%, at least 95%, or at least 98% sequence identity thereto). In more specific embodiments, the non-naturally occurring collagen is an amino acid sequence of SEQ ID NO: 2, SEQ ID NO: 4, SEQ ID NO: 5, SEQ ID NO: 7, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 25, SEQ ID NO: 27, or SEQ ID NO: 29, or a homolog thereof (e.g., having at least 85%, at least 90%, at least 95%, or at least 98% sequence identity thereto).

In certain embodiments, compositions are provided herein. In some embodiments, such a composition comprises any polypeptides (e.g., truncated or non-natural collagen) described herein. In one aspect, provided are compositions that comprise any suitable amount, such as between 0.005% and 30% w/w, of any polypeptide (e.g., truncated or non-naturally occurring collagen) provided herein. The compositions can further comprise at least one additional ingredient comprising an excipient, a topical carrier, or a preservative.

In certain embodiments, a composition provided herein is a topical composition, such as a composition that is formulated and/or suitable for topical administration or use. In one aspect, provided herein is a method, such as of providing a benefit (e.g., as described herein) to the skin of an individual, the method comprising topically administering the topical composition to skin. In specific embodiments, the topical compositions are used in methods for decreasing skin damage, promoting the repair of damaged skin, or stimulating production of collagen by skin cells. In certain embodiments, the topical compositions are used in methods for increasing, promoting, stimulating, or otherwise increasing elastin production in the skin.

One aspect provides methods for applying the collagen or a composition comprising collagen to the skin of a subject.

As discussed herein, in some embodiments, a polypeptide provided herein is or comprises a truncated amino acid sequence relative to a natural (e.g., human or jellyfish (Hydrozoan)) collagen. In specific embodiments, such a polypeptide is a truncated collagen (e.g. comprises one or more truncated amino acid sequence relative to a natural collagen). In some embodiments, the truncated collagen is a jellyfish collagen or a human collagen. In various embodiments, the collagen is truncated at the C-terminal end, the N-terminal end, internally truncated, or truncated at both the C-terminal end and the N-terminal end (e.g., relative to a natural collagen). In one embodiment, the collagen is truncated at both the C-terminal end and the N-terminal end (e.g., relative to a natural collagen). In certain embodiments, a polypeptide provided herein is or comprises a truncated collagen of any suitable truncation, such as comprising a truncation at the C-terminal end, the N-terminal end, and/or one or more internal truncations. In some embodiments, truncation of the collagen is suitable to achieve beneficial results (e.g., an improved result relative to natural collagen and/or an additional benefit relative to natural collagen) and/or to shorten the length of the collagen while retaining one or more beneficial aspect of collagens. In some embodiments, polypeptides provided herein are or comprise a collagen that is truncated in a manner such as to retain one or more topical benefit of collagen.

In some embodiments, a truncated collagen (amino acid sequence thereof) (e.g., of a polypeptide provided herein) is truncated at the C-terminal end by any suitable number of amino acid residues, such as up to 10, 10 to 800, 10 to 700, 10 to 500, 10 to 400, 10 to 300, 50 to 800, 50 to 700, 50 to 600, 50 to 500, 50 to 400, or the like. In certain embodiments, a truncated collagen (amino acid sequence thereof) (e.g., of a polypeptide provided herein) is truncated at the N-terminal end by any suitable number of amino acid residues, such as up to 10, 10 to 900, 10 to 800, 10 to 700, 10 to 500, 10 to 400, 10 to 300, 50 to 800, 50 to 700, 50 to 600, 50 to 500, 50 to 400, or the like. In some embodiments, a truncated collagen (amino acid sequence thereof) (e.g., of a polypeptide provided herein) is internally truncated by any suitable number of amino acid residues, such as up to 10, 10 to 900, 10 to 800, 10 to 700, 10 to 500, 10 to 400, 10 to 300, 50 to 800, 50 to 700, 50 to 600, 50 to 500, 50 to 400, or the like. In specific embodiments, a truncated collagen (amino acid sequence thereof) (e.g., of a polypeptide provided herein) is truncated at the C-terminal end by between 10 and 800 amino acids and/or truncated at the N-terminal end by between 10 and 800 amino acids. In another embodiment, the truncated collagen (amino acid sequence thereof) (e.g., of a polypeptide provided herein) is between 10 and 900 amino acids in length, between 10 and 800 amino acids in length, between 10 and 700 amino acids in length, between 10 and 600 amino acids in length, between 10 and 500 amino acids in length, between 10 and 400 amino acids in length, between 10 and 300 amino acids in length, between 10 and 200 amino acids in length, between 10 and 100 amino acids in length, between 10 and 50 amino acids in length, between 50 and 800 amino acids in length, between 50 and 700 amino acids in length, between 50 and 600 amino acids in length, between 50 and 500 amino acids in length, between 50 and 400 amino acids in length, between 50 and 300 amino acids in length, between 50 and 200 amino acids in length, or between 50 and 100 amino acids in length.

In certain embodiments, provided herein is a polypeptide that is or comprises an amino acid sequence of a human (e.g., human type 21) collagen. In specific embodiments, the truncated human collagen is a truncated human type 21 collagen. In various embodiments, truncation is according to any disclosure provided herein. In a specific embodiment, the truncated human type 21 collagen disclosed is SEQ ID NO: 16 (or a homolog thereof, such as having at least 80% sequence identity, at least 85% sequence identity, at least 90% sequence identity, at least 95% sequence identity, at least 98% sequence identity, or other sequence identity provided herein to an amino acid sequence of SEQ ID NO: 16). In various embodiments, such polypeptides are provided in any composition, formulation, or method provided herein.

In certain embodiments, provided herein is a polypeptide that is or comprises an amino acid sequence of a jellyfish (Hydrozoan) collagen. In various embodiments, the truncation is according to any disclosure provided herein. In a specific embodiment, the truncated jellyfish collagen disclosed is SEQ ID NO: 5 (or a homolog thereof, such as having at least 80% sequence identity, at least 85% sequence identity, at least 90% sequence identity, at least 95% sequence identity, at least 98% sequence identity, or other sequence identity provided herein to an amino acid sequence of SEQ ID NO: 5). In various embodiments, such polypeptides are provided in any composition, formulation, or method provided herein.

In certain embodiments, provided herein is a method comprising administering a polypeptide (e.g., that is or comprises a truncated collagen described herein) to the skin of an individual, such as to provide a benefit to the individual or to the skin thereof. In some instances, the benefit provided to the skin is improved firmness of the skin, improved elasticity of the skin, improved hydration of the skin, improved texture of the skin, improved brightness of the skin, decreased wrinkling of the skin, decreased erythema of the skin, improved collagen production in the skin, improved or increased elastin production in the skin, antioxidant protection to the skin, decreased redness of the skin, or other benefit, or combination of benefits, such as those described herein. In various instances, improvement in skin characteristics, or benefits provided by a method provided herein, is determined in any suitable manner, such as by use of instrumentation or by evaluation by a clinician. In one aspect, a method of increasing the firmness of skin is provided wherein the firmness of the skin is increased by at least 5%, 10%, 15%, 20%, 25%, 30%, 35%, 40%, 45%, 50%, 55%, 60%, 70%, or 75%. In one embodiment the firmness of the skin is measured using a cutometer.

Another aspect provides a method of increasing the elasticity of skin wherein the firmness of the skin is increased by at least 5%, 10%, 15%, 20%, 25%, 30%, 35%, 40%, 45%, 50%, 55%, 60%, 70%, or 75%. In one embodiment the elasticity of the skin is measured using a cutometer.

In another aspect, a method of increasing hydration of skin is provided wherein the hydration of the skin increases by at least 5%, 10%, 15%, 20%, 25%, 30%, 35%, 40%, 45%, 50%, 55%, 60%, 70%, or 75%. In one embodiment, skin hydration is measured on a corneometer.

In one aspect, a method of increasing the firmness of skin is provided wherein the firmness of the skin is increased. In one embodiment, the firmness of the skin is determined by an expert clinical grader.

In one aspect, a method of increasing the elasticity of skin is provided wherein the elasticity of the skin is increased. In one embodiment, the elasticity of the skin is determined by an expert clinical grader.

In one aspect, a method of increasing the brightness of skin is provided wherein the brightness of the skin is increased. In one embodiment, the brightness of the skin is determined by an expert clinical grader.

In another aspect, a method of increasing the tactile texture of skin is provided wherein the tactile texture of the skin is increased. In one embodiment, the tactile texture of the skin is determined by an expert clinical grader.

In one aspect, a method of increasing the visual texture of skin is provided wherein the visual texture of the skin is increased. In one embodiment, the visual texture of the skin is determined by an expert clinical grader.

In one aspect, a method of decreasing the lines or wrinkles present on skin is provided wherein the lines or wrinkles present on the skin is decreased. In one embodiment, the amount of lines or wrinkles present on of the skin is determined by an expert clinical grader.

In one aspect, a method of decreasing the erythema of skin is provided wherein the erythema of the skin is decreased. In one embodiment, the erythema of the skin is determined by an expert clinical grader.

Another aspect provides a method of stimulating collagen production in a skin cell. In one embodiment, the method comprises applying a non-naturally occurring truncated collagen or a formulation that comprises non-naturally occurring truncated collagen to the skin. In one embodiment, truncated jellyfish collagen or truncated human collagen stimulates collagen production. In a specific embodiment, the truncated human collagen is a truncated human type 21 collagen of SEQ ID NO: 16. In another specific embodiment, the truncated jellyfish collage is a truncated jellyfish collagen of SEQ ID NO: 5.

Yet another aspect provides a method of stimulating collagen production in skin cells, wherein the collagen in skin increases by at least 1%, at least 2%, at least 3%, at least 4%, at least 5%, at least 6%, at least 7%, at least 8%, at least 9%, or at least 10%.

A topical formulation comprising a truncated collagen and one or more additional ingredient selected from the group consisting of water, oil, glycereth-8 esters, glycerin, coconut alkanes, hydroxyethyl acrylate/sodium acryloyldimethyl taurate copolymer, pentylene glycol, disodium EDTA, caprylyl glycol, chlorphenesin, and phenoxyethanol is disclosed. In one embodiment, the truncated collagen is a truncated jellyfish collagen or a truncated human collagen. In another embodiment, the truncated collagen is a truncated human type 21 collagen. Yet another embodiment disclosed herein is a topical formulation comprising collagen and further comprising a vegetable oil. In one embodiment, the vegetable oil is olive oil.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 18 shows an exemplary Visual Analog Scale (VAS) used to assess efficacy after treatment with exemplary polypeptides provided herein.

DESCRIPTION

Figure 1:
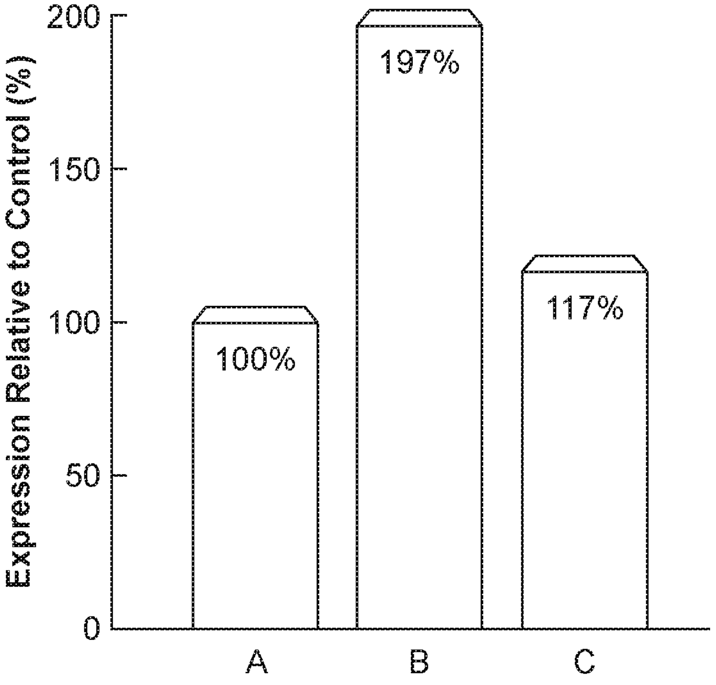
FIG. 1 illustrates an effect of an exemplary polypeptide provided herein (comprising a truncated human collagen amino acid sequence) on collagen type 1 protein secretion in fibroblasts.

In the following description, certain specific details are set forth in order to provide a thorough understanding of various embodiments of the disclosure. However, one skilled in the art will understand that the disclosure may be practiced without these details.

As used herein the term “about” generally refers to +10%.

The term “consisting of” means “including and limited to”. In general, a disclosure of “comprising” include a disclosure of “consisting of.”

The term “consisting essentially of” means that the composition, method, or structure may include additional ingredients, steps, and/or parts, but only if the additional ingredients, steps, and/or parts do not materially alter the basic and novel characteristics of the claimed composition, method, or structure. In general, a disclosure of “comprising” includes a disclosure of “consisting essentially of.”

As used herein, the singular form “a”, “an” and “the” include plural references unless the context clearly dictates otherwise. For example, the term “a compound” or “at least one compound” may include a plurality of compounds, including mixtures thereof.

Throughout this document, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases “ranging/ranges between” a first indicate number and a second indicate number and “ranging/ranges from” a first indicate number “to” a second indicate number are used herein interchangeably and are meant to include the first and second indicated numbers and all the fractional and integral numerals there between.

The term “collagen” or “collagen-like” as used herein refers, in some instances, to a (e.g., monomeric) polypeptide that can associate with one or more collagen or collagen-like polypeptides to form a quaternary structure. Non-limiting examples of a collagen include a human type 21 alpha 1 collagen (e.g., SEQ ID NO: 31), a human type 1, alpha 2 collagen (e.g., SEQ ID NO: 32), and a jellyfish (Hydrozoan) collagen (e.g., SEQ ID NO: 33). In some instances, a collagen can be treated with acid, base, or heat to prepare a gelatin. The quaternary structure of natural collagen is a triple helix, typically composed of three polypeptides, but it should be noted that a “truncated collagen” or a polypeptide comprising a “truncated collagen” provided herein may or may not have such a quaternary structure, and does not necessarily have such a quaternary structure. In certain instances, of the three polypeptides that form natural collagen, two are usually identical and are designated as the alpha chain. The third polypeptide is designated as the beta chain. In certain instances, a typical natural collagen can be designated as AAB, wherein the collagen is composed of two alpha (“A”) strands and one beta (“B”) strand. In certain instances, polypeptides comprising “truncated collagens” provided herein may or may not have such structural elements. The term “collagen” or “collagen-like” may refer to the alpha chain polypeptide, the beta chain polypeptide, or both the alpha and beta chain polypeptides. The term “procollagen” as used herein generally refers to polypeptides produced by cells that can be processed to naturally occurring collagen.

The term “expression vector” or “vector” as used herein generally refers to a nucleic acid assembly which is capable of directing the expression of the exogenous gene. The expression vector may include a promoter which is operably linked to the exogenous gene, restriction endonuclease sites, nucleic acids that encode one or more selection markers, and other nucleic acids useful in the practice of recombinant technologies.

The term “fibroblast” as used herein generally refers to a cell that synthesizes procollagen and other structural proteins. Fibroblasts are widely distributed in the body and found in skin, connective tissue and other tissues.

The term “fluorescent protein” generally refers to a protein that may be used in genetic engineering technologies used as a reporter of expression of an exogenous polynucleotide. The protein when exposed to ultraviolet or blue light fluoresces and emits a bright visible light. Proteins that emit green light include green fluorescent protein (GFP) and proteins that emit red light include red fluorescent protein (RFP).

The term “gelatin” as used herein generally refers to collagen that has been further processed by exposure to acid, base or heat. In some instances, gelatin solutions form reversible gels used in foods, cosmetics, pharmaceuticals, industrial products, medical products, laboratory culture growth media, and many other applications.

The term “gene” as used herein generally refers to a polynucleotide that encodes a specific protein, and which may refer to the coding region alone or may include regulatory sequences preceding (5' non-coding sequences) and following (3' non-coding sequences) the coding sequence.

The term “histidine tag” generally refers to a 2-30 contiguous series of histidine residues on a recombinant polypeptide.

The term “host cell” generally refers to a cell that is engineered to express an introduced exogenous polynucleotide.

The term “keratinocyte” generally refers to a cell that produces keratins found in the epidermal layer of the skin.

The term “lactamase” as used herein generally refers to enzymes that hydrolyze antibiotics that contain a lactam (cyclic amide) moiety. “Beta-lactamase” or “β-lactamase” are enzymes that hydrolyze antibiotics that contain a β-lactam moiety.

The term “non-naturally occurring” as used herein refers to a gene, polypeptide, or protein, for example, a collagen, that is not normally found in nature. The non-naturally occurring collagens may be recombinantly prepared. The non-naturally occurring collagen may be a recombinant collagen. The non-naturally occurring collagen is, in one embodiment, a truncated collagen. Other non-naturally occurring collagen polypeptides include chimeric collagens. A chimeric collagen is a polypeptide wherein one portion of a collagen polypeptide is contiguous with a portion of a second collagen polypeptide. For example, a collagen molecule comprising a portion of a jellyfish collagen contiguous with a portion of a human collagen is a chimeric collagen. In another embodiment, the non-naturally occurring collagen comprises a fusion polypeptide that includes additional amino acids such as a secretion tag, histidine tag, green fluorescent protein, protease cleavage site, GEK repeats, GDK repeats, and/or beta-lactamase.

In general, disclosure of a collagen or truncated collagen provided herein, such as having a specific amino acid sequence, includes polypeptides having or comprising that precise amino acid sequence and homologs thereof. In some instances, homologs of an amino acid sequence provided herein may have a longer or shorter sequence and may have substitution of one or more amino acid residue of such amino acid sequence. Such homologs have a specific sequence identity to the recited sequence, such as in an amount provided herein. Sequence identity, such as for the purpose of assessing percent identity, may be measured by any suitable alignment algorithm, including but not limited to the Needleman-Wunsch algorithm (see, e.g., the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters. In some cases, a non-naturally occurring collagen may have at least 60%, 65%, 70%, 75%, 80%, 85%, 90%, 95%, 97%, 98%, 99%, or 100% sequence identity to a sequence disclosed herein.

The term "protease cleavage site" generally refers to an amino acid sequence that is cleaved by a specific protease.

The term "secretion tag" or "signal peptide" generally refers to an amino acid sequence that recruits the host cell's cellular machinery to transport an expressed protein to a particular location or cellular organelle of the host cell.

The term "truncated collagen" generally refers to a monomeric polypeptide that is smaller than a full-length collagen wherein one or more portions of the full-length collagen is not present. Collagen polypeptides are truncated at the C-terminal end, the N-terminal end, truncated by removal of internal portion(s) of the full-length collagen polypeptide (e.g., an internal truncation), or truncated at both the C-terminal end and the N-terminal end. In a non-limiting embodiment, a truncated human collagen may comprise an amino acid sequence according to SEQ ID NO: 16, or a homolog thereof. In another non-limiting example, a truncated jellyfish collagen may comprise an amino acid sequence according to SEQ ID NO: 5, or a homolog thereof. Generally, a truncated collagen provided herein may have a function and/or provide a benefit (e.g., as provided herein) similar or substantially similar to that of a natural or a full-length collagen. In some cases, a truncated collagen provided herein may have improved or increased function and/or benefit (e.g., as provided herein) as compared to a natural or a full-length collagen.

When used in reference to an amino acid position, a "truncation" is inclusive of said amino acid position. For example, an N-terminal truncation at amino acid position 100 of a full-length protein means a truncation of 100 amino acids from the N-terminus of the full-length protein (i.e., the truncated protein is missing amino acid positions 1 through 100 of the full-length protein). Similarly, a C-terminal truncation at amino acid position 901 of a full-length protein (assuming a 1000 amino acid full-length protein) means a truncation of 100 amino acids from the C-terminus (i.e., the truncated protein is missing amino acid positions 901 through 1000 of the full-length protein). Similarly, an internal truncation at amino acid positions 101 and 200 means a internal truncation of 100 amino acids of the full-length protein (i.e., the truncated protein is missing amino acid positions 101 to 200 of the full-length protein).

In some embodiments, the cell culture may further comprise one or more of: ammonium chloride, ammonium sulfate, calcium chloride, amino acids, iron (II) sulfate, magnesium sulfate, peptone, potassium phosphate, sodium chloride, sodium phosphate, and yeast extract.

The host bacterial cell may be cultured continuously or discontinuously; in a batch process, a fed-batch process or a repeated fed-batch process.

In general, the signal sequence may be a component of the expression vector, or it may be a part of the exogenous gene that is inserted into the vector. The signal sequence selected may be one that is recognized and processed (e.g., cleaved by a signal peptidase) by the host cell. For bacterial host cells that do not recognize and process the native signal sequence of the exogenous gene, the signal sequence may be substituted by any commonly known bacterial signal sequence. In some embodiments, recombinantly produced polypeptides can be targeted to the periplasmic space using the DsbA signal sequence. Dinh and Bernhardt, J Bacteriol, September 2011, 4984-4987.

In one aspect, a non-naturally occurring collagen that is produced by a host cell is provided. The non-naturally occurring collagen can be a jellyfish collagen or human collagen. The non-naturally occurring collagen may be a truncated collagen. The truncation may be an internal truncation (e.g., a truncation of an internal portion), a truncation at the N-terminal portion of the collagen, a truncation at the C-terminal portion of the collagen, or a truncation at both the C-terminal end and the N-terminal end. The collagen may be truncated by a truncation of between 50 amino acids and 1000 amino acids, between, 50 amino acids and 950 amino acids, between 50 amino acids and 900 amino acids, between 50 amino acids and 850 amino acids, between 50 amino acids and 800 amino acids, between 50 amino acids and 850 amino acids, between 50 amino acids and 800 amino acids, between 50 amino acids and 750 amino acids, between 50 amino acids and 700 amino acids, between 50 amino acids and 650 amino acids, between 50 amino acids and 600 amino acids, between 50 amino acids and 650 amino acids, between 50 amino acids and 500 amino acids, between 50 amino acids and 450 amino acids, between 50 amino acids and 400 amino acids, between 50 amino acids and 350 amino acids, between 50 amino acids and 300 amino acids, between 50 amino acids and 250 amino acids, between 50 amino acids and 200 amino acids, between 50 amino acids and 150 amino acids, or between 50 amino acids and 100 amino acids. In another embodiment, the collagen may be truncated by about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, or 1000 amino acids. The non-naturally occurring collagen may be encoded by a portion of a polynucleotide sequence or the entire polynucleotide sequence disclosed herein.

A truncated collagen disclosed herein may comprise a truncation relative to a full-length collagen. In some embodiments, a truncated collagen disclosed herein may comprise a truncation relative to a full-length human type 21 alpha 1 collagen. In some embodiments, a truncated collagen disclosed herein may comprise a truncation relative to a full-length human type 1 alpha 2 collagen. In some embodiments, a truncated collagen disclosed herein comprise a truncation relative to a full-length jellyfish (Hydrozoan) collagen. Non-limiting examples of full-length collagens are provided in Table 1 below.

amino acid positions 1 and 553; between amino acid positions 1 and 558; between amino acid positions 1 and 563; between amino acid positions 1 and 568; or between amino acid positions 1 and 573 of SEQ ID NO: 31. In some cases, a truncated collagen as described herein may comprise a C-terminal truncation at any amino acid position between amino acid positions 726 and 957; between amino acid positions 731 and 957; between amino acid positions 736 and 957; between amino acid positions 741 and 957; between amino acid positions 746 and 957; between amino acid positions 751 and 957; or between amino acid positions 756 and 957 of SEQ ID NO: 31. In some cases, a truncated collagen as described herein may comprise both an N-terminal truncation and a C-terminal truncation. For example,

TABLE 1

Full-length collagen amino acid sequences

| Collagen | Amino Acid Sequence |
|---|---|
| Human type 21 alpha 1 collagen | MAHYITFLCMVLVLLLQNSVLAEDGEVRSSCRTAPTDLVFILDGSYSVGPENFEIVKKWL<br>VNITKNFDIGPKFIQVGVVQYSDYPVLEIPLGSYDSGEHLTAAVESILYLGGNTKTGKAI<br>QFALDYLFAKSSRFLTKIAVVLTDGKSQDDVKDAAQAARDSKITLFAIGVGSETEDAELR<br>AIANKPSSTYVFYVEDYIAISKIREVMKQKLCEESVCPTRIPVAARDERGFDILLGLDVN<br>KKVKKRIQLSPKKIKGYEVTSKVDLSELTSNVFPEGLPPSYVFVSTQRFKVKKIWDLWRI<br>LTIDGRPQIAVTLNGVDKILLFTTTSVINGSQVVTFANPQVKTLFDEGWHQIRLLVTEQD<br>VTLYIDDQQIENKPLHPVLGILINGQTQIGKYSGKEETVQFDVQKLRIYCDPEQNNRETA<br>CEIPGFNGECLNGPSDVGSTPAPCICPPGKPGLQGPKGDPGLPGNPGYPGQPGQDGKPGY<br>QGIAGTPGVPGSPGIQGARGLPGYKGEPGRDGDKGDRGLPGFPGLHGMPGSKGEMGAKGD<br>KGSPGFYGKKGAKGEKGNAGFPGLPGPAGEPGRHGKDGLMGSPGFKGEAGSPGAPGQDGT<br>RGEPGIPGFPGNRGLMGQKGEIGPPGQQGKKGAPGMPGLMGSNGSPGQPGTPGSKGSKGE<br>PGIQGMPGASGLKGEPGATGSPGEPGYMGLPGIQGKKGDKGNQGEKGIQGQKGENGRQGI<br>PGQQGIQGHHGAKGERGEKGEPGVRGAIGSKGESGVDGLMGPAGPKGQPGDPGPQGPPGL<br>DGKPGREFSEQFIRQVCTDVIRAQLPVLLQSGRIRNCDHCLSQHGSPGIPGPPGPIGPEG<br>PRGLPGLPGRDGVPGLVGVPGRPGVRGLKGLPGRNGEKGSQGFGYPGEQGPPGPPGPEGP<br>PGISKEGPPGDPGLPGKDGDHGKPGIQGQPGPPGICDPSLCFSVIARRDPFRKGPNY<br>(SEQ ID NO: 31) |
| Human type 1 alpha 2 collagen | MLSFVDTRTLLLLAVTLCLATCQSLQEETVRKGPAGDRGPRGERGPPGPPGRDGEDGPTG<br>PPGPPGPPGPPGLGGNFAAQYDGKGVGLGPGPMGLMGPRGPPGAAGAPGPQGFQGPAGEP<br>GEPGQTGPAGARGPAGPPGKAGEDGHPGKPGRPGERGVVGPQGARGFPGTPGLPGFKGIR<br>GHNGLDGLKGQPGAPGVKGEPGAPGENGTPGQTGARGLPGERGRVGAPGPAGARGSDGSV<br>GPVGPAGPIGSAGPPGFPGAPGPKGEIGAVGNAGPAGPAGPRGEVGLPGLSGPVGPPGNP<br>GANGLTGAKGAAGLPGVAGAPGLPGPRGIPGPVGAAGATGARGLVGEPGPAGSKGESGNK<br>GEPGSAGPQGPPGPSGEEGKRGPNGEAGSAGPPGPPGLRGSPGSRGLPGADGRAGVMGPP<br>GSRGASGPAGVRGPNGDAGRPGEPGLMGPRGLPGSPGNIGPAGKEGPVGLPGIDGRPGPI<br>GPAGARGEPGNIGFPGPKGPTGDPGKNGDKGHAGLAGARGAPGPDGNNGAQGPPGPQGVQ<br>GGKGEQGPPGPPGFQGLPGPSGPAGEVGKPGERGLHGEFGLPGPAGPRGERGPPGESGAA<br>GPTGPIGSRGPSGPPGPDGNKGEPGVVGAVGTAGPSGPSGLPGERGAAGIPGGKGEKGEP<br>GLRGEIGNPGRDGARGAPGAVGAPGPAGATGDRGEAGAAGPAGPAGPRGSPGERGEVGPA<br>GPNGFAGPAGAAGQPGAKGERGAKGPKGENGVVGPTGPVGAAGPAGPNGPPGPAGSRGDG<br>GPPGMTGFPGAAGRTGPPGPSGISGPPGPPGPAGKEGLRGPRGDQGPVGRTGEVGAVGPP<br>GFAGEKGPSGEAGTAGPPGTPGPQGLLGAPGILGLPGSRGERGLPGVAGAVGEPGPLGIA<br>GPPGARGPPGAVGSPGVNGAPGEAGRDGNPGNDGPPGRDGQPGHKGERGYPGNIGPVGAA<br>GAPGPHGPVGPAGKHGNRGETGPSGPVGPAGAVGPRGPSGPQGIRGDKGEPGEKGPRGLP<br>GLKGHNGLQGLPGIAGHHGDQGAPGSVGPAGPRGPAGPSGPAGKDGRTGHPGTVGPAGIR<br>GPQGHQGPAGPPGPPGPPGPPGVSGGGYDFGYDGDFYRADQPRSAPSLRPKDYEVDATLK<br>SLNNQIETLLTPEGSRKNPARTCRDLRLSHPEWSSGYYWIDPNQGCTMDAIKVYCDFSTG<br>ETCIRAQPENIPAKNWYRSSKDKKHVWLGETINAGSQFEYNVEGVTSKEMATQLAFMRLL<br>ANYASQNITYHCKNSIAYMDEETGNLKKAVILQGSNDVELVAEGNSRFTYTVLVDGCSKK<br>TNEWGKTIIEYKTNKPSRLPFLDIAPLDIGGADQEFFVDIGPVCFK<br>(SEQ ID NO: 32) |
| Jellyfish (Hydrozoan) collagen | GPQGVVGADGKDGTPGEKGEQGRTGAAGKQGSPGADGARGPLGSIGQQGARGEPGDPGSP<br>GLRGDTGLAGVKGVAGPSGRPGQPGANGLPGVNGRGGLRGKPGAKGIAGSDGEAGESGAP<br>GQSGPTGPRGQRGPSGEDGNPGLQGLPGSDGEPGEEGQPGRSGQPGQQGPRGSPGEVGPR<br>GSKGPSGDRGDRGERGVPGQTGSAGNVGEDGEQGGKGVDGASGPSGALGARGPPGSRGDT<br>GAVGPPGPTGRSGLPGNAGQKGPSGEPGSPGKAGSAGEQGPPGKDGSNGEPGSPGKEGER<br>GLAGPPGPDGRRGETGSPGIAGALGKPGLEGPKGYPGLRGRDGTNGKRGEQGETGPDGVR<br>GIPGNDGQSGKPGIDGIDGTNGQPGEAGYQGGRGTRGQLGETGDVGQNGDRGAPGPDGSK<br>GSAGRPGLR<br>(SEQ ID NO: 33) |

In some cases, a truncated collagen as described herein may comprise an N-terminal truncation at any amino acid position between amino acid positions 1 and 548; between a truncated collagen as described herein may comprise an N-terminal truncation at any amino acid position between amino acid positions 1 and 548; between amino acid positions 1 and 553; between amino acid positions 1 and 558; between amino acid positions 1 and 563; between amino acid positions 1 and 568; or between amino acid positions 1 and 573 of SEQ ID NO: 31; and a C-terminal truncation at any amino acid position between amino acid positions 726 and 957; between amino acid positions 731 and 957; between amino acid positions 736 and 957; between amino acid positions 741 and 957; between amino acid positions 746 and 957; between amino acid positions 751 and 957; or between amino acid positions 756 and 957. In a specific embodiment, a truncated collagen disclosed herein may comprise an N-terminal truncation at amino acid position 558 of SEQ ID NO: 31; and a C-terminal truncation at amino acid position 746 of SEQ ID NO: 31.

In some cases, a truncated collagen as described herein may comprise an N-terminal truncation at any amino acid position between amino acid positions 1 and 401; between amino acid positions 1 and 406; between amino acid positions 1 and 411; between amino acid positions 1 and 416; between amino acid positions 1 and 421; between amino acid positions 1 and 426; or between amino acid positions 1 and 431 of SEQ ID NO: 32. In some cases, a truncated collagen as described herein may comprise a C-terminal truncation at any amino acid position between amino acid positions 585 and 1366; between amino acid positions 590 and 1366; between amino acid positions 595 and 1366; between amino acid positions 600 and 1366; between amino acid positions 605 and 1366; between amino acid positions 610 and 1366; between amino acid positions 615 and 1366; or between amino acid positions 620 and 1366 of SEQ ID NO: 32. In some cases, a truncated collagen as described herein may comprise both an N-terminal truncation and a C-terminal truncation. For example, a truncated collagen as described herein may comprise an N-terminal truncation at any amino acid position between amino acid positions 1 and 401; between amino acid positions 1 and 406; between amino acid positions 1 and 411; between amino acid positions 1 and 416; between amino acid positions 1 and 421; between amino acid positions 1 and 426; or between amino acid positions 1 and 431 of SEQ ID NO: 32; and a C-terminal truncation at any amino acid position between amino acid positions 585 and 1366; between amino acid positions 590 and 1366; between amino acid positions 595 and 1366; between amino acid positions 600 and 1366; between amino acid positions 605 and 1366; between amino acid positions 610 and 1366; between amino acid positions 615 and 1366; or between amino acid positions 620 and 1366 of SEQ ID NO: 32. In a specific embodiment, a truncated collagen as provided herein may comprise an N-terminal truncation at amino acid position 416 of SEQ ID NO: 32; and a C-terminal truncation at amino acid position 605 of SEQ ID NO: 32.

In some cases, a truncated collagen as described herein may comprise an N-terminal truncation at any amino acid position between amino acid positions 1 and 101; between amino acid positions 1 and 106; between amino acid positions 1 and 111; between amino acid positions 1 and 116; between amino acid positions 1 and 121; or between amino acid positions 1 and 126 of SEQ ID NO: 32. In some cases, a truncated collagen as described herein may comprise a C-terminal truncation at any amino acid position between amino acid positions 276 and 1366; between amino acid positions 281 and 1366; between amino acid positions 286 and 1366; between amino acid positions 291 and 1366; between amino acid positions 296 and 1366; between amino acid positions 301 and 1366; or between amino acid positions 306 and 1366 of SEQ ID NO: 32. In some cases, a truncated collagen as described herein may comprise both an N-terminal truncation and a C-terminal truncation. For example, a truncated collagen as described herein may comprise an N-terminal truncation at any amino acid position between amino acid positions 1 and 101; between amino acid positions 1 and 106; between amino acid positions 1 and 111; between amino acid positions 1 and 116; between amino acid positions 1 and 121; or between amino acid positions 1 and 126 of SEQ ID NO: 32; and a C-terminal truncation at any amino acid position between amino acid positions 276 and 1366; between amino acid positions 281 and 1366; between amino acid positions 286 and 1366; between amino acid positions 291 and 1366; between amino acid positions 296 and 1366; between amino acid positions 301 and 1366; or between amino acid positions 306 and 1366 of SEQ ID NO: 32. In a specific embodiment, a truncated collagen as provided herein may comprise an N-terminal truncation at amino acid position 111 of SEQ ID NO: 32; and a C-terminal truncation at amino acid position 291 of SEQ ID NO: 32.

In some cases, a truncated collagen as described herein may comprise an internal truncation at any amino acid position between amino acid positions 16 and 240; between amino acid positions 16 and 245; between amino acid positions 16 and 250; between amino acid positions 16 and 255; between amino acid positions 16 and 260; between amino acid positions 16 and 265; between amino acid positions 6 and 255; between amino acid positions 11 and 255; between amino acid positions 21 and 255; between amino acid positions 26 and 255; between amino acid positions 31 and 255; between amino acid positions 21 and 250; between amino acid positions 21 and 245; between amino acid positions 26 and 250; between amino acid positions 26 and 245; between amino acid positions 31 and 250; or between amino acid positions 31 and 245 of SEQ ID NO: 33. In a specific embodiment, a truncated collagen as described herein may comprise an internal truncation at amino acid positions 16 and 255 of SEQ ID NO: 33.

In some cases, a truncated collagen may comprise any amino acid sequence provided in Table 2 below. In some cases, a truncated collagen may consist of any amino acid sequence provided in Table 2 below. In some cases, a truncated collagen may consist essentially of any amino acid sequence provided in Table 2 below. In specific embodiments, the non-naturally occurring collagen is or comprises an amino acid sequence of any one of SEQ ID NO: 2, SEQ ID NO: 4, SEQ ID NO: 5, SEQ ID NO: 7, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 25, SEQ ID NO: 27, and SEQ ID NO: 29. In some embodiments, the truncated collagen comprises an amino acid sequence having at least 85%, at least 90%, at least 95%, or at least 98% sequence identity to any one of SEQ ID NO: 2, SEQ ID NO: 4, SEQ ID NO: 5, SEQ ID NO: 7, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 25, SEQ ID NO: 27, and SEQ ID NO: 29.

TABLE 2

Non-limiting examples of truncated collagens

| SEQ ID NO: | Amino acid sequence |
|---|---|
| SEQ ID | MKKIWLALAGLVLAFSASAAQYEDHHHHHHHHHHSGSSLVPRGSHM GPQGVVGADGKDGTPGEKGEQGRTGAAGKQGSPGADGARGPLGSI |

TABLE 2-continued

Non-limiting examples of truncated collagens

| SEQ ID NO: | Amino acid sequence |
|---|---|
| NO: 2 | GQQGARGEPGDPGSPGLRGDTGLAGVKGVAGPSGRPGQPGANGLPGVNGRGGLERGLAGPPGPDGRRGETGSPGIAGALGKPGLEGPKGYPGLRGRDGTNGKRGEQGETGPDGVRGIPGNDGQSGKPGIDGIDGTNGQPGEAGYQGGRGTRGQLGETGDVGQNGDRGAPGPDGSKGSAGRPGLR |
| SEQ ID NO: 4 | GPQGVVGADGKDGTPGEKGEQGRTGAAGKQGSPGADGARGPLGSIGQQGARGEPGDPGSPGLRGDTGLAGVKGVAGPSGRPGQPGANGLPGVNGRGGLERGLAGPPGPDGRRGETGSPGIAGALGKPGLEGPKGYPGLRGRDGTNGKRGEQGETGPDGVRGIPGNDGQSGKPGIDGIDGTNGQPGEAGYQGGRGTRGQLGETGDVGQNGDRGAPGPDGSKGSAGRPGLR |
| SEQ ID NO: 7 | MKKIWLALAGLVLAFSASAAQYEDGPQGVVGADGKDGTPGNAGQKGPSGEPGSPGKAGSAGEQGPPGKDGSNGEPGSPGKEGERGLAGPPGPDGRRGETGSPGIAGALGKPGLEGPKGYPGLRGRDGTNGKRGEQGETGPDGVRGIPGNDGQSGKPGIDGIDGTNGQPGEAGYQGGRGTRGQLGETGDVGQNGDRGAPGPDGSKGSAGRPGLR |
| SEQ ID NO: 5 | GPQGVVGADGKDGTPGNAGQKGPSGEPGSPGKAGSAGEQGPPGKDGSNGEPGSPGKEGERGLAGPPGPDGRRGETGSPGIAGALGKPGLEGPKGYPGLRGRDGTNGKRGEQGETGPDGVRGIPGNDGQSGKPGIDGIDGTNGQPGEAGYQGGRGTRGQLGETGDVGQNGDRGAPGPDGSKGSAGRPGLR |
| SEQ ID NO: 10 | MKKIWLALAGLVLAFSASAAQYEDHHHHHHHHHSGSSLVPRGSHMSGSSSKGEELFTGVVPILVELDGDVNGHKFSVRGEGEGDATNGKLTLKFICTTGKLPVPWPTLVTTLTYGVQCFSRYPDHMKQHDFFKSAMPEGYVQERTISFKDDGTYKTRAEVKFEGDTLVNRIELKGIDFKEDGNILGHKLEYNFNSHNVYITADKQKNGIKANFKIRHNVEDGSVQLADHYQQNTPIGDGPVLLPDNHYLSTQSKLSKDPNEKRDHMVLLEFVTAAGITHGMDELYKSGAPGGPQGVVGADGKDGTPGNAGQKGPSGEPGSPGKAGSAGEQGPPGKDGSNGEPGSPGKEGERGLAGPPGPDGRRGETGSPGIAGALGKPGLEGPKGYPGLRGRDGTNGKRGEQGETGPDGVRGIPGNDGQSGKPGIDGIDGTNGQPGEAGYQGGRGTRGQLGETGDVGQNGDRGAPGPDGSKGSAGRPGLRHPETLVKVKDAEDQLGARVGYIELDLNSGKILESFRPEERFPMMSTFKVLLCGAVLSRIDAGQEQLGRRIHYSQNDLVEYSPVTEKHLTDGMTVRELCSAAITMSDNTAANLLLTTIGGPKELTAFLHNMGDHVTRLDRWEPELNEAIPNDERDTTMPVAMATTLRKLLTGELLTLASRQQLIDWMEADKVAGPLLRSALPAGWFIADKSGAGERGSRGIIAALGPDGKPSRIVVIYTTGSQATMDERNRQIAEIGASLIKHW |
| SEQ ID NO: 12 | MKKIWLALAGLVLAFSASAAQYEDHHHHHHHHHSGSSLVPRGSHMSGSSSKGEELFTGVVPILVELDGDVNGHKFSVRGEGEGDATNGKLTLKFICTTGKLPVPWPTLVTTLTYGVQCFSRYPDHMKQHDFFKSAMPEGYVQERTISFKDDGTYKTRAEVKFEGDTLVNRIELKGIDFKEDGNILGHKLEYNFNSHNVYITADKQKNGIKANFKIRHNVEDGSVQLADHYQQNTPIGDGPVLLPDNHYLSTQSKLSKDPNEKRDHMVLLEFVTAAGITHGMDELYKSGAPGGPQGVVGADGKDGTPGNAGQKGPSGEPGSPGKAGSAGEQGPPGKDGSNGEPGSPGKEGERGLAGPPGPDGRRGETGSPGIAGALGKPGLEGPKGYPGLRGRDGTNGKRGEQGETGPDGVRGIPGNDGQSGKPGIDGIDGTNGQPGEAGYQGGRGTRGQLGETGDVGQNGDRGAPGPDGSKGSAGRPGLRHPETLVKVKDAEDQLGARVGYIELDLNSGKILESFRPEERFPMMSTFKVLLCGAVLSRIDAGQEQLGRRIHYSQNDLVEYSPVTEKHLTDGMTVRELCSAAITMSDNTAANLLLTTIGGPKELTAFLHNMGDHVTRLDRWEPELNEAIPNDERDTTMPVAMATTLRKLLTGELLTLASRQQLIDWMEADKVAGPLLRSALPAGWFIADKSGAGERGSRGIIAALGPDGKPSRIVVIYTTGSQATMDERNRQIAEIGASLIKHW |
| SEQ ID NO: 14 | MKKIWLALAGLVLAFSASAAQYEDAGFPGLPGPAGEPGRHGKDGLMGSPGFKGEAGSPGAPGQDGTRGEPGIPGFPGNRGLMGQKGEIGPPGQQGKKGAPGMPGLMGSNGSPGQPGTPGSKGSKGEPGIQGMPGASGLKGEPGATGSPGEPGYMGLPGIQGKKGDKGNQGEKGIQGQKGENGRQGIPGQQGIQGHHGAKGERGEKGEPGVR |
| SEQ ID NO: 16 | AGFPGLPGPAGEPGRHGKDGLMGSPGFKGEAGSPGAPGQDGTRGEPGIPGFPGNRGLMGQKGEIGPPGQQGKKGAPGMPGLMGSNGSPGQPGTPGSKGSKGEPGIQGMPGASGLKGEPGATGSPGEPGYMGLPGIQGKKGDKGNQGEKGIQGQKGENGRQGIPGQQGIQGHHGAKGERGEKGEPGVR |
| SEQ ID NO: 18 | MKKIWLALAGLVLAFSASAAQYEDMGPPGSRGASGPAGVRGPNGDAGRPGEPGLMGPRGLPGSPGNIGPAGKEGPVGLPGIDGRPGPIGPAGARGEPGNIGFPGPKGPTGDPGKNGDKGHAGLAGARGAPGPDGNNGAQGPPGPQGVQGGKGEQGPAGPPGFQGLPGPSGPAGEVGKPGERGLHGEFGLPGPAGPRGERGPPGESGAAGPTG |
| SEQ ID NO: 20 | MGPPGSRGASGPAGVRGPNGDAGRPGEPGLMGPRGLPGSPGNIGPAGKEGPVGLPGIDGRPGPIGPAGARGEPGNIGFPGPKGPTGDPGKNGDKGHAGLAGARGAPGPDGNNGAQGPPGPQGVQGGKGEQGPAGPPGFQGLPGPSGPAGEVGKPGERGLHGEFGLPGPAGPRGERGPPGESGAAGPTG |
| SEQ ID NO: 22 | MKKIWLALAGLVLAFSASAAQYEDGFQGPAGEPGEPGQTGPAGARGPAGPPGKAGEDGHPGKPGRPGERGVVGPQGARGFPGTPGLPGFKGIRGHNGLDGLKGQPGAPGVKGEPGAPGENGTPGQTGARGLPGERGRVGAPGPAGARGSDGSVGPVGPAGPIGSAGPPGFPGAPGPKGEIGAVGNAGPAGPAGPRGEVGLPGL |
| SEQ ID NO: 24 | GFQGPAGEPGEPGQTGPAGARGPAGPPGKAGEDGHPGKPGRPGERGVVGPQGARGFPGTPGLPGFKGIRGHNGLDGLKGQPGAPGVKGEPGAPGENGTPGQTGARGLPGERGRVGAPGPAGARGSDGSVGPVGPAGPIGSAGPPGFPGAPGPKGEIGAVGNAGPAGPAGPRGEVGLPGL |
| SEQ ID NO: 25 | MKKIWLALAGLVLAFSASAGDQGPVGRTGEVGAVGPPGFAGEKGPSGEAGTAGPPGTPGPQGLLGAPGILGLPGSRGERGLPGVAGAVGEPGPLGIAGPPGARGPPGAVGSPGVNGAPGEAGRDGNPGNDGPPGRDGQPGHKGERGYPGNIGPVGAAGAPGPHGPVGPAGKHGNRGETGPSGPVGPAGAVGPRGPSGPQGIRGDKGEPGEKGPRGLPGLGDYKDDDDK |
| SEQ ID NO: 27 | MKKIWLALAGLVLAFSASAKGHNGLQGLPGIAGHHGDQGAPGSVGPAGPRGPAGPSGPAGKDGRTGHPGTVGPAGIRGPQGHQGPAGPPGPPGPPGPPGVSGGGYDFGYDGDFYRADQPRSAPSLRPKDYEVDATLKSLNNQIETLLTPEGSRKNPARTCRDLRLSHPEWSSGYYWIDPNQGCTMDAIKVYCDFSTGETCIRAQPENIPAKNWYRSSKDGDYKDDDDK |
| SEQ ID NO: 29 | MKKIWLALAGLVLAFSASAYEVDATLKSLNNQIETLLTPEGSRKNPARTCRDLRLSHPEWSSGYYWIDPNQGCTMDAIKVYCDFSTGETCIRAQPENIPAKNWYRSSKDKKHVWLGETINAGSQFEYNVEGVTSKEMATQLAFMRLLANYASQNITYHCKNSIAYMDEETGNLKKAVILQGSNDVELVAEGNSRFTYTVLVDGCSKKTNEWGKTIIEYKTNKPSRLPFLDIAPLDIGGADQEFFVDIGPVCFKGDYKDDDDK |

In some cases, a truncated collagen may be between 100 and 300 amino acids, between 150 and 250 amino acids, between 160 and 250 amino acids, between 160 and 220 amino acids, between 170 and 200 amino acids, between 180 and 190 amino acids, or between 185 and 190 amino acids in length.

The non-naturally occurring collagen may, in some embodiments, further comprise amino acid sequences including a secretion tag. The secretion tag may direct the collagen to the periplasmic space of the host cell. In particular embodiments, the signal peptide is derived from DsbA, PelB, OmpA, TolB, MalE, Ipp, TorA, Hy1A, DegP, or a hybrid secretion tag that comprises a portion of one secretion tag fused to a portion of a second secretion tag. In one aspect the secretion tag may be attached to the non-naturally occurring collagen. In another aspect the secretion tag may be cleaved from the non-naturally occurring collagen.

In some embodiments, the non-naturally occurring collagen comprises a histidine (or polyhistidine) tag. In specific embodiments, the histidine tag or polyhistidine tag is or comprises a sequence of 2 to 20 histidine residues that are attached to the collagen. In various embodiments, the histidine tag comprises 2 to 20 histidine residues, 5 to 15 histidine residues, 5 to 18 histidine residues, 5 to 16 histidine residues, 5 to 15 histidine residues, 5 to 14 histidine residues, 5 to 13 histidine residues, 5 to 12 histidine residues, 5 to 11 histidine residues, 5 to 10 histidine residues, 6 to 12 histidine residues, 6 to 11 histidine residues, or 7 to 10 histidine residues. The histidine tags may be useful in purification of proteins by chromatographic methods utilizing nickel based chromatographic media. Exemplary fluorescent proteins include green fluorescent protein (GFP) or red fluorescent protein (RFP). Fluorescent proteins are well known in the art. In one embodiment, a non-naturally occurring collagen comprises a GFP and/or RFP. In one embodiment, a superfolder GFP is fused to a non-naturally occurring collagen. The superfolder GFP may be a GFP that folds properly even when fused to a poorly folded polypeptide. In one aspect, a histidine tag may be attached to the non-naturally occurring collagen. In another aspect, a histidine tag may be cleaved from the non-naturally occurring collagen.

In some embodiments, the non-naturally occurring collagen further comprises a protease cleavage site. The protease cleavage site may be useful to cleave the recombinantly produced collagen to remove one or more portions of the polypeptide. The portions of the polypeptide that may be removed include the secretion tag, the histidine tag, the fluorescent protein tag, and/or the Beta-lactamase. The proteases may comprise endoproteases, exoproteases, serine proteases, cysteine proteases, threonine proteases, aspartic proteases, glutamic proteases, and metalloproteases. Exemplary protease cleavage sites include amino acids that are cleaved by Thrombin, TEV protease, Factor Xa, Enteropeptidase, and Rhinovirus 3C Protease. In one aspect, the cleavage tag is attached to the non-naturally occurring collagen. In another aspect, the cleavage tag is removed by an appropriate protease from the non-naturally occurring collagen.

In some embodiments, the non-naturally occurring collagen further comprises an enzyme that is a Beta-lactamase. The beta-lactamase may be useful as a selection marker. In one aspect, the beta-lactamase is attached to the non-naturally occurring collagen. In another aspect, the beta-lactamase is cleaved from the non-naturally occurring collagen.

Provided in certain embodiments herein are (e.g., topical) compositions or formulations comprising one or more polypeptide provided herein. In some embodiments, the composition provides any suitable amount of polypeptide provided herein, such as in any suitable amount (e.g., an amount suitable to provide a benefit when given or administered to an individual or cell). In some specific embodiments, the composition comprises an amount suitable to provide a beneficial effect to the skin of an individual when (e.g., topically) administered to the skin of the individual. In specific embodiments, the composition comprises between 0.001% and 30% w/w of a polypeptide (or non-naturally occurring collagen) such as provided herein. In more specific embodiments, the composition comprises between 0.001% and 20% w/w of a polypeptide (or non-naturally occurring collagen) such as provided herein, between 0.001% and 10% w/w of a polypeptide (or non-naturally occurring collagen) such as provided herein, between 0.001% and 5% w/w of a polypeptide (or non-naturally occurring collagen) such as provided herein, between 0.001% and 2% w/w of a polypeptide (or non-naturally occurring collagen) such as provided herein, between 0.001% and 1% w/w of a polypeptide (or non-naturally occurring collagen) such as provided herein, between 0.001% and 0.5% w/w of a polypeptide (or non-naturally occurring collagen) such as provided herein, and between 0.001% and 0.2% w/w of a polypeptide (or non-naturally occurring collagen) such as provided herein.

In one aspect, the compositions that comprise non-naturally occurring collagen may be personal care products (e.g., a cosmetic). In some embodiments, the compositions are formulated for topical administration. The compositions can contain other cosmetic ingredients suitable for human use. The personal care products may be useful for preventing or treating ultraviolet radiation damage to human skin or hair. The personal care products may be useful for increasing the firmness, elasticity, brightness, hydration, tactile texture or visual texture of skin and/or stimulate collagen production. The personal care products may be useful for reducing redness of the skin. The personal care products may be applied to skin or hair. The compositions include, for example, masks, skin cleaners such as soap, cleansing creams, cleansing lotions, facial cleansers, cleansing milks, cleansing pads, facial washes, facial and body creams and moisturizers, facial serums, facial and body masks, facial toners and mists, eye creams and eye treatments, exfoliator formulas, lip balms and lipsticks, hair shampoo, hair conditioner and body shampoos, hair and scalp serums, hair mists and sprays, eye shadow, concealer, mascara and other color cosmetics.

The compositions that comprise the non-naturally occurring collagen can further comprise at least one additional ingredient comprising a topical carrier or a preservative. The topical carrier may comprise a topical carrier selected from the group consisting of liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, cyclopentasiloxane and water. The preservative may comprise a preservative selected from the group consisting of tocopherol, diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, phenoxyethanol, butylene glycol, 1,2 Hexanediol, methyl paraben, sorbic acid, Germaben II, rosemary extract, and EDTA Also provided in certain embodiments herein, are methods of decreasing skin damage, promoting the repair of damaged skin, protecting skin against UV damage, and/or protecting skin cells against the effects of exposure to urban dust. In another embodiment, methods of increasing the firmness, elasticity, brightness, hydration, tactile texture, or visual texture of skin and/or stimulating collagen production are provided. The methods may comprise a step of applying a composition comprising a non-naturally occurring collagen to the skin of a subject. Without being bound to a particular theory or mechanism, the collagen in the composition may decrease skin damage by protecting against UV damage. In some cases, the collagen in the composition may promote the repair of damaged skin by increasing the viability of cells. In some cases, the collagen in the composition may decrease skin damage and/or promote repair of cells by increasing procollagen synthesis when applied to skin, and/or promoting the viability of skin cells. In some cases, the collagens decrease the formation of thymine-thymine (TT) dimer formation.

The methods provided herein encompass the use of a composition for treatment indicated in the method, such as by the steps provided herein. In embodiments, the disclosure provides the use of a composition provided herein (e.g., a truncated collagen or a formulation comprising a truncated collagen) in a method for decreasing skin damage, promoting the repair of damaged skin, protecting skin against UV damage, and/or protecting skin cells against the effects of exposure to urban dust (e.g., such as by administering to the skin of a subject a composition provided herein). In embodiments, the disclosure provides the use of a composition provided herein (e.g., a truncated collagen or a formulation comprising a truncated collagen) in a method for increasing the firmness, elasticity, brightness, hydration, tactile texture, or visual texture of skin and/or stimulating collagen production.

In some embodiments, a truncated collagen as provided herein may stimulate fibroblast and/or keratinocyte production of collagen type I (see, e.g., Example 4 and Example 6). In some cases, the levels of pro-collagen type I C-peptide (a read-out for collagen production) may be measured. In some cases, an in vitro MatTek full thickness human skin tissue model may be used (see, e.g., Example 6) to assess pro-collagen type I C-peptide levels. In some cases, collagen type I levels may be measured or determined by an enzyme-linked immunosorbent assay (ELISA). In some cases, a truncated collagen as provided herein may stimulate production of collagen type I at a higher level than untreated cells, cells treated with retinol, and/or cells treated with Vitamin B3.

In some embodiments, a truncated collagen as provided herein may stimulate fibroblast overexpression of extracellular matrix genes (see, e.g., Example 4). In some cases, the levels of extracellular matrix genes may be measured by RNA sequencing. In some cases, a truncated collagen as provided herein may stimulate fibroblast overexpression of one or more of the collagen type I gene (COL1A), the elastin gene (ELN), and the fibronectin gene (FN1). In some cases, the levels of extracellular matrix genes produced by fibroblasts treated with a truncated collagen provided herein may be higher than untreated fibroblasts, or fibroblasts treated with retinol. In some cases, the levels of extracellular matrix genes produced by fibroblasts treated with a truncated collagen provided herein may be similar to, or higher than, fibroblasts treated with Vitamin C.

In some embodiments, a truncated collagen as provided herein may reduce inflammation of keratinocytes irradiated with UVB light (see, e.g., Example 4 and Example 6). In some cases, keratinocytes may be irradiated with UVB light, and then treated with a truncated collagen as provided herein. In some cases, inflammation may be measured by measuring the levels of IL-1α produced by UVB-irradiated keratinocytes (e.g., by ELISA). In some cases, UVB-irradiated keratinocytes may produce lower levels of IL-1α when treated with a truncated collagen provided herein than untreated keratinocytes.

In some embodiments, a truncated collagen as provided herein may increase viability of keratinocytes irradiated with UVB light (see, e.g., Example 4). In some cases, keratinocytes may be pre-treated (prior to UVB irradiation) and post-treated (after UVB irradiation) with a truncated collagen provided herein. In some cases, cell viability may be measured using an MTT metabolic colorimetric assay. In some cases, keratinocytes treated with a truncated collagen provided herein may exhibit greater cell viability after UVB irradiation than untreated keratinocytes.

In some embodiments, a truncated collagen as provided herein may reduce DNA damage in keratinocytes after exposure to UVB light (see, e.g., Example 6). In some cases, DNA damage may be assessed by measuring the levels of thymine dimers (TT-dimers). In a non-limiting example, the OxiSelect UV-induced DNA damage ELISA kit may be used to measure TT-dimer levels. In some cases, UVB-irradiated keratinocytes treated with a truncated collagen provided herein may show lower levels of TT-dimers than untreated keratinocytes.

In some embodiments, a truncated collagen as provided herein may have anti-oxidative capacity (see, e.g., Example 4 and Example 6). In some cases, an oxygen radical absorbance capacity (ORAC) assay may be used to measure oxidative capacity of the truncated collagen. In a non-limiting example, a truncated collagen in the form of a 0.1% solution may have anti-oxidative properties of at least 10 μM Trolox (Vitamin E) equivalents (TEs), at least 50 μM TEs, at least 100 μM TEs, at least 150 μM TEs, at least 160 μM TEs, at least 170 μM TEs, at least 180 μM TEs, at least 190 μM TEs, or at least 200 μM TEs.

In some embodiments, a truncated collagen as provided herein may increase cell viability of keratinocytes exposed to urban dust pollution as compared to untreated cells (see, e.g., Example 6). In some cases, cell viability may be measured by an MTT metabolic colorimetric assay.

In some embodiments, topical administration of a truncated collagen provided herein to the face of a subject may result in increased facial skin elasticity, as compared to baseline, at 1 week, 2 weeks, 4 weeks, 8 weeks, or longer, post-treatment (see, e.g., Example 5 and Example 7). In some cases, facial skin elasticity may be measured by a cutometer.

In some embodiments, topical administration of a truncated collagen provided herein to the face of a subject may result in an increase in facial skin collagen content, as compared to baseline, at 1 week, at 2 weeks, at 4 weeks, at 8 weeks, or longer, post-treatment (see, e.g., Example 5). In some cases, facial skin collagen content may be measured by a SIAscope.

In some embodiments, topical administration of a truncated collagen provided herein may result in a reduction in facial skin redness (erythema), as compared to baseline, at 1 week, at 2 weeks, at 4 weeks, at 8 weeks, or longer, post-treatment (see, e.g., Example 5). In some cases, facial skin redness (erythema) may be scored by a blinded clinical grader (e.g., using a 5-point ordinal scale as provided in Table 4).

In some embodiments, topical administration of a truncated collagen provided herein may result in a reduction in facial wrinkles, as compared to baseline, at 1 week, at 2 weeks, at 4 weeks, at 8 weeks, or longer, post-treatment (see, e.g., Example 5). In some cases, facial wrinkles may be scored by a blinded clinical grader.

In some embodiments, topical administration of a truncated collagen provided herein may result in increased facial skin moisture, as compared to baseline, at 1 week, at 2 weeks, at 4 weeks, at 8 weeks, or longer, post-treatment (see, e.g., Example 7). In some cases, topical administration of a truncated collagen provided herein may result in increased facial skin moisture as compared to topical administration of a marine collagen. In some cases, skin hydration may be measured by a corneometer.

One aspect of this disclosure provides polynucleotides that encode a non-naturally occurring collagen. The polynucleotides may encode collagen from jellyfish or human. The polynucleotides may encode for a collagen that is full length or truncated. In various embodiments, the polynucleotide may comprise a polynucleotide according to any one of SEQ ID NO: 1, SEQ ID NO: 3, SEQ ID NO: 6, SEQ ID NO: 8, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 26, SEQ ID NO: 28, or SEQ ID NO: 30, or a homolog thereof (e.g., having at least 85%, at least 90%, at least 95%, or at least 98% sequence identity thereto). In some cases, the polynucleotide may be codon optimized (e.g., for expression in a host cell).

In another aspect the present disclosure provides polynucleotides that encode collagen fusion proteins. The collagen fusion proteins may comprise a secretion tag, a histidine tag, a fluorescent protein tag, a protease cleavage site, a Beta-lactamase along and/or GEK amino acid trimer repeats and/or GDK amino acid trimer repeats together with collagen.

In an aspect, vectors comprising the collagen encoding polynucleotides may be used to transform host cells and express the polynucleotides. The polynucleotides may further comprise nucleic acids that encode enzymes that permit the host organism to grow in the presence of a selection agent. The selection agents may include certain sugars including galactose containing sugars or antibiotics including ampicillin, hygromycin, G418, and others. Enzymes that can be used to confer resistance to the selection agent include β-galactosidase or a β-lactamase.

In one aspect, host cells that express the polynucleotides of the invention are provided. Host cells can be any host cell including gram negative bacterial cells, gram positive bacterial cells, yeast cells, insect cells, mammalian cells, plant cells, or any other cells used to express exogenous polynucleotides. An exemplary gram-negative host cell is *E. coli.*

Any desirable or necessary supplements besides carbon, nitrogen, and inorganic phosphate sources may also be included at appropriate concentrations introduced alone or as a mixture with another supplement or medium such as a complex nitrogen source. In certain embodiments, the medium further comprises one or more ingredients selected from: ammonium chloride, ammonium sulfate, calcium chloride, casamino acids, iron (II) sulfate, magnesium sulfate, peptone, potassium phosphate, sodium chloride, sodium phosphate, and yeast extract.

Beta-lactamases are enzymes that confer resistance to lactam antibiotics in prokaryotic cells. Typically when Beta-lactamases are expressed in bacterial host cells, the expressed Beta-lactamase proteins also include targeting sequences (secretion tag) that direct the Beta-lactamase proteins to the periplasmic space. Beta-lactamases are not functional unless they are transported to the periplasmic space. Beta-lactamases targeted to the periplasmic space without the use of an independent secretion tag that targets the enzyme to the periplasmic space are provided. By creating a fusion protein in which a periplasmic secretion tag is added to the N-terminus of a protein such as GFP, collagen, or GFP/collagen chimeras, the functionality of the Beta-lactamase lacking a native secretion tag can be used to select for full translation and secretion of the N-terminal fusion proteins. Using this approach, a DsbA-GFP-Collagen-Beta-lactamase fusion may be used to select for truncation products in the target collagens that favor translation and secretion.

Another embodiment provides methods of producing a polypeptide (or non-naturally occurring collagen), such as provided herein. In some embodiments, the method comprises the steps of inoculating a culture medium with a recombinant host cell comprising polynucleotides that encode the polypeptide or "collagen," cultivating the host cell, and isolating the polypeptide (or non-naturally occurring collagen) from the host cell.

A process for fermentative preparation of a polypeptide (or protein) is provided. The process comprises the steps of:

(a) culturing a recombinant Gram-negative bacterial cell in a medium comprising a magnesium salt, wherein the concentration of magnesium ions in the medium is at least about 6 mM, and wherein the bacterial cell comprises an exogenous gene encoding the protein; and (b) harvesting the protein from the medium.

The bacteria may be cultured in any suitable manner, such as continuously—as described, for example, in WO 05/021772—or discontinuously in a batch process (batch cultivation) or in a fed-batch or repeated fed-batch process for the purpose of producing the target protein. In some embodiments, protein production is conducted on a large-scale. Various large-scale fermentation procedures are available for production of recombinant proteins. Large-scale fermentations have at least 1,000 liters of capacity, preferably about 1,000 to 100,000 liters of capacity. In some instances, fermenters use agitator impellers to distribute oxygen and nutrients, especially glucose (the preferred carbon/energy source). Small-scale fermentation refers generally to fermentation in a fermenter that is no more than approximately 20 liters in volumetric capacity.

For accumulation of the target protein, the host cell may be cultured under conditions sufficient for accumulation of the target protein. Such conditions include, e.g., temperature, nutrient, and cell-density conditions that permit protein expression and accumulation by the cell. Moreover, such conditions may be those under which the cell can perform basic cellular functions of transcription, translation, and passage of proteins from one cellular compartment to another for the secreted proteins, as are known to those skilled in the art.

Any suitable bacterial cell is optionally utilized in a method provided herein. The bacterial cells may be cultured at any suitable temperature. In specific embodiments, the bacterial cells are *E. coli* cells. For *E. coli* growth, for example, the typical temperature ranges from about 20° C. to about 39° C. In one embodiment, the temperature is from about 20° C. to about 37° C. In another embodiment, the temperature is at about 30° C. In one embodiment, the host cells, in the non-switched state or switched state may be cultivated at one temperature and switched to a different temperature to induce protein production. The host cells may be cultivated first at one temperature to propagate the cells, then to induce protein production the cells may be cultivated at a lower temperature. The first temperature may be about 23°, 24°, 25°, 26°, 27°, 28°, 29°, 30°, 31°, 32°, 33°, 34°, 35°, 36°, or 37° C. The second temperature may be about 20°, 21°, 22°, 23°, 24°, 25°, 26°, 27°, 28°, 29°, 30°, 31°, 32°, 33°, 34°, 35° or 36° C. The cultivation at the second temperature may be conducted between 1 hour and 100 hours, between 5 hours and 90 hours, between 5 hours and 80 hours, between 5 hours and 80 hours, between 5 hours and 70 hours, between 10 hours and 70 hours, between 15 hours and 70 hours, between 15 hours and 65 hours, between 15 hours and 60 hours, between 20 hours and 60 hours, between 20 hours and 55 hours, between 20 hours and 50 hours, between 24 hours and 50 hours, between 24 hours and 48 hours, between 30 hours and 50 hours, between 30 hours and 45 hours, or between 30 hours and 40 hours.

The pH of the culture medium may be any pH from about 5-9, depending mainly on the host organism. For *E. coli*, the pH may be from about 6.0 to about 7.4, about 6.2 to about 7.2, about 6.2 to about 7.0, about 6.2 to about 6.8, about 6.2 to about 6.6, about 6.4 or about 6.5.

For induction of gene expression, typically the cells may be cultured until a certain optical density is achieved, e.g., an OD600 of about 1.1, at which point induction is initiated (e.g., by addition of an inducer, by depletion of a repressor, suppressor, or medium component, etc.) to induce expression of the exogenous gene encoding the target protein. In some embodiments, expression of the exogenous gene may be inducible by an inducer selected from, e.g., isopropyl-β-d-1-thiogalactopyranoside, lactose, arabinose, maltose, tetracycline, anhydrotetracycline, vavlycin, xylose, copper, zinc, and the like. The induction of gene expression can also be accomplished by decreasing the dissolved oxygen levels during fermentation. The dissolved oxygen levels of the fermentation during cell propagation may be between 10% and 30%. To induce gene expression the dissolved oxygen level may be reduced to below 10%, 9%, 8%, 7%, 6%, 5%, 4%, 3%, 2%, 1%, or 0%. In host cells, in either the physiological state or the switched state, protein production can be induced by lowering the temperature of the fermentation as disclosed herein.

EXAMPLES

Example 1. Production of Truncated Collagen

A codon optimized DNA sequence, optimized for expression in *E. coli*, encoding a jellyfish collagen with a truncation of 240 internal amino acids (relative to full-length jellyfish collagen (SEQ ID NO: 33)) was synthesized and expressed. The DNA sequence is shown below in SEQ ID NO: 1. In SEQ ID NO: 1, the DsbA secretion tag is encoded by nucleotides 1-72 and encodes amino acids 1-24 of SEQ ID NO: 2. The histidine tag comprising 9 histidine residues is encoded by nucleotides 73-99 of SEQ ID NO: 1 and encodes amino acids 25-33 of SEQ ID NO: 2. The linker is encoded by nucleotides 100-111 of SEQ ID NO: 1 and encodes amino acids 34-37 of SEQ ID NO: 2. The thrombin cleavage site is encoded by nucleotides 112-135 of SEQ ID NO: 1 and encodes amino acids 38-45 of SEQ ID NO: 2. The truncated collagen is encoded by nucleotides 136-822 of SEQ ID NO: 1 and encodes amino acids 46-274 of SEQ ID NO: 2.

(SEQ ID NO: 1)

```
ATGAAAAAGATTTGGCTGGCGCTGGCTGGTTTAGTTTTAGCGTTTAGCGC

ATCGGCGGCGCAGTATGAAGATCACCATCACCACCACCACCATCACCACT

CTGGCTCGAGCCTGGTGCCGCGCGGCAGCCATATGGGTCCGCAGGGTGTT

GTTGGTGCAGATGGTAAAGACGGTACCCCGGGTGAAAAAGGAGAACAGGG

ACGTACAGGTGCAGCAGGTAAACAGGGCAGCCCGGGTGCCGATGGTGCCC

GTGGCCCGCTGGGTAGCATTGGTCAGCAGGGTGCAAGAGGCGAACCGGGC

GATCCGGGTAGTCCGGGCCTGCGTGGTGATACGGGTCTGGCCGGTGTTAA

AGGCGTTGCAGGTCCTTCAGGTCGTCCAGGTCAACCGGGTGCAAATGGTC

TGCCGGGTGTTAATGGTCGTGGCGGTCTGGAACGTGGTCTGGCAGGACCG

CCGGGTCCTGATGGTCGCCGCGGTGAAACGGGTTCACCGGGTATTGCCGG

TGCCCTGGGTAAACCAGGTCTGGAAGGTCCGAAAGGTTATCCTGGTCTGC

GCGGTCGTGATGGTACCAATGGCAAACGTGGCGAACAGGGCGAAACCGGT

CCAGATGGTGTTCGTGGTATTCCGGGTAACGATGGTCAGAGCGGTAAACC
```

-continued

```
GGGCATTGATGGTATTGATGGCACCAATGGTCAGCCTGGCGAAGCAGGTT

ATCAGGGTGGTCGCGGTACCCGTGGTCAGCTGGGTGAAACAGGTGATGTT

GGTCAGAATGGTGATCGCGGCGCACCGGGTCCGGATGGTAGCAAAGGTAG

CGCCGGTCGTCCGGGTTTACGTTAA
```

The truncated collagen is approximately 54% of the full length jellyfish collagen (SEQ ID NO: 33) and is disclosed below in SEQ ID NO: 2.

(SEQ ID NO: 2)

```
MKKIWLALAGLVLAFSASAAQYEDHHHHHHHHHSGSSLVPRGSHMGPQGV

VGADGKDGTPGEKGEQGRTGAAGKQGSPGADGARGPLGSIGQQGARGEPG

DPGSPGLRGDTGLAGVKGVAGPSGRPGQPGANGLPGVNGRGGLERGLAGP

PGPDGRRGETGSPGIAGALGKPGLEGPKGYPGLRGRDGTNGKRGEQGETG

PDGVRGIPGNDGQSGKPGIDGIDGTNGQPGEAGYQGGRGTRGQLGETGDV

GQNGDRGAPGPDGSKGSAGRPGLR
```

The polynucleotide encoding the truncated jellyfish collagen without the DsbA secretion tag, the histidine tag, linker and thrombin cleavage site is disclosed in SEQ ID NO: 3.

(SEQ ID NO: 3)

```
GTCCGCAGGGTGTTGTTGGTGCAGATGGTAAAGACGGTACCCCGGGTGAA

AAAGGAGAACAGGGACGTACAGGTGCAGCAGGTAAACAGGGCAGCCCGGG

TGCCGATGGTGCCCGTGGCCCGCTGGGTAGCATTGGTCAGCAGGGTGCAA

GAGGCGAACCGGGCGATCCGGGTAGTCCGGGCCTGCGTGGTGATACGGGT

CTGGCCGGTGTTAAAGGCGTTGCAGGTCCTTCAGGTCGTCCAGGTCAACC

GGGTGCAAATGGTCTGCCGGGTGTTAATGGTCGTGGCGGTCTGGAACGTG

GTCTGGCAGGACCGCCGGGTCCTGATGGTCGCCGCGGTGAAACGGGTTCA

CCGGGTATTGCCGGTGCCCTGGGTAAACCAGGTCTGGAAGGTCCGAAAGG

TTATCCTGGTCTGCGCGGTCGTGATGGTACCAATGGCAAACGTGGCGAAC

AGGGCGAAACCGGTCCAGATGGTGTTCGTGGTATTCCGGGTAACGATGGT

CAGAGCGGTAAACCGGGCATTGATGGTATTGATGGCACCAATGGTCAGCC

TGGCGAAGCAGGTTATCAGGGTGGTCGCGGTACCCGTGGTCAGCTGGGTG

AAACAGGTGATGTTGGTCAGAATGGTGATCGCGGCGCACCGGGTCCGGAT

GGTAGCAAAGGTAGCGCCGGTCGTCCGGGTTTACGTTAA
```

The truncated jellyfish collagen amino acid sequence without the DsbA secretion tag, the histidine tag, linker and thrombin cleavage site is disclosed in SEQ ID NO: 4.

(SEQ ID NO: 4)

```
GPQGVVGADGKDGTPGEKGEQGRTGAAGKQGSPGADGARGPLGSIGQQGA

RGEPGDPGSPGLRGDTGLAGVKGVAGPSGRPGQPGANGLPGVNGRGGLER

GLAGPPGPDGRRGETGSPGIAGALGKPGLEGPKGYPGLRGRDGTNGKRGE

QGETGPDGVRGIPGNDGQSGKPGIDGIDGTNGQPGEAGYQGGRGTRGQLG

ETGDVGQNGDRGAPGPDGSKGSAGRPGLR
```

The polynucleotides of SEQ ID NO: 1 were codon optimized and synthesized by Gen9 DNA (now Ginkgo Bioworks) internal synthesis. Overlaps between the pET28 vector and SEQ ID NO: 1 were designed to be between 30 and 40 bp long and were added using PCR with the enzyme PrimeSTAR® GXL polymerase (www.clontech.com/US/Products/PCR/GC_Rich/PrimeSTAR_GXL_DNA_Polymerase?sitex=10020:22372:US). The opened pET28a vector and insert DNA (SEQ ID NO: 1) was then assembled together into the final plasmid using SGI Gibson Assembly® (us.vwr.com/store/product/17613857/gibson-assembly-hifi-1-step-kit-synthetic-genomics-inc). The plasmid sequence was then verified through Sanger sequencing through Eurofins Genomics (www.eurofinsgenomics.com).

The transformed cells were cultivated in minimal media and frozen in 1.5 ml aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH 7 with Dissolved Oxygen maintained at 20% saturation using a cascade containing agitation, air, and oxygen. pH was controlled using 28% w/w ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25° C. High density culture was induced for protein production using 1 mM IPTG. Fermentation was continued for another 20-24 hours and cells were harvested using a bench top centrifuge at 9000 rcf, 15° C. for 60 minutes. The cell pellet recovered from centrifugation was resuspended in a buffer containing 0.5 M NaCl and 0.1 M KH2PO4 at pH 8 in a weight by weight ratio of 2× buffer to 1× cells.

The harvested cells were disrupted in a homogenizer at 14,000 psi pressure in 2 passes. The resulting slurry contained the collagen protein along with other proteins.

The fermentations were performed at various temperature ranging from 25° to 28° C. For some fermentations, the temperature of the fermentation was maintained at a constant temperature and immediately upon completion of fermentation (OD600 of 5-10) the collagen was purified. For other fermentations, the temperature of the fermentations was maintained for a desired period of time and when cell densities of OD600 of 5-10 were reached, the temperature was reduced to induce protein production. Typically, the temperature was reduced from 28° C. to 25° C. After the fermentation at 25° C. was continued for 40-60 hours, the collagen was isolated.

The collagen was purified by acid treatment of homogenized cell broth. Additionally, acid treatment was also performed on non-homogenized whole cells recovered from the bioreactor after centrifugation and resuspension in the buffer described above. The pH of either the homogenized slurry or the resuspended whole cells was decreased to pH 3 using 6 M hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 $m^2$ each. Total area of filtration was 0.2 $m^2$ using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified truncated collagen obtained from homogenized cell broth or non-homogenized cells were analyzed on an SDS-PAGE gel and a thick and clear band was observed at the expected size of 27 kilodaltons. The purified collagen was also analyzed by mass spectrometry and it was confirmed that the 27 kilodalton protein was jellyfish collagen.

An alternative purification method of the full length and truncated collagens is provided below.

The fermentation broth was mixed with 0.3-0.5% w/v of Poly Ethyl Imine (PEI). After 15 minutes of incubation with PEI, the fermentation broth was centrifuged at 9000 ref for 15 minutes to recover the supernatant, which contained the collagen protein. The pellet containing the cells was discarded and the PEI-treated collagen containing supernatant was mixed with Sodium Bentonite (0.2% final w/v) (Wyopure®, Wyoming Bentonite) and centrifuged. The bentonite containing pellet was discarded and the supernatant was recovered.

The Bentonite treated supernatant was concentrated between 3-6 fold on a tangential flow filtration system (TFF) (EMD Millipore) using a 5 kDa cassette. The collagen was retained with almost no losses in the permeate stream. To remove salts, the retentate from the concentration step was diafiltered using the same TFF set-up. Final conductivity of the protein solution was <10 milliSiemens. The typical conductivity was between 400 microsiemens and 1.5 millisiemens. Highly concentrated collagen solutions had higher conductivities approaching 4 milliSiemens. A skilled artisan will understand that conductivities higher than 10 milliSiemens may be observed depending on the concentration of the collagen. Next, the desalted and concentrated protein was subjected to treatment with activated carbon using the W-L 9000 10×40 granulated resin (Carbon Activated Corporation). 5% w/v of the carbon resin was mixed with collagen containing protein feed and mixed at 45-50° C. with mild agitation. The carbon-treated slurry was filtered using a Buchner funnel lined with an Ertel Filter Press Pad M-953 (Ertel Alsop) in presence or absence of a filtration aid such as Diatomaceous Earth (Sigma Aldrich). Post-filtration, the collagen solution was filtered through a 0.2 micron filter followed by one to several hours of treatment with Sodium Bentonite (0.2% w/v final) (Wyopure®, Wyoming Bentonite) and centrifuged at 9000 rcf, 15-30 minutes to obtain a highly pure, clear and particulate free collagen solution. When removal of endotoxin proteins was desired, the protein was passed through a chromatographic filter like Sartobind-Q (Sartorius-Stedim) to specifically remove endotoxin proteins.

The purified collagen was analyzed on an SDS-PAGE gel and a thick and clear band was observed at 30 kilodaltons. The upshift in size is due to the structure of the collagen molecule and the high glycine/proline amino acid content. The purified collagen was also analyzed by mass spectrometry and it was confirmed that the 30 kilodalton protein was the truncated collagen.

The truncated collagens were further analyzed by HPLC using an Agilent 1100 series HPLC. The column was the 50 mm Agilent PLRP-S reverse phase column with an inner diameter of 4.6 mm, μM particle size and 1000 Angstrom pore size.

The sample was prepared by diluting 1:1 in a 0.04% sodium azide solution in HPLC-grade water. After dilution, the resulting mixture was filtered through a 0.45 μm filter to remove any large particles that can clog the HPLC column. For analysis, the samples are diluted appropriately with a 20 mM ammonium acetate buffer in HPLC-grade water at a pH of about 4.5. After mixing the sample, it was transferred to a 300 μL microvial that was then placed in the autosampler. Using ChemStation, the software that operates the HPLC, the analysis parameters such as sample flowrate, column temperature, mobile phase flowrate, mobile phase composition, etc. can be altered. In one exemplary, but non-limiting analysis the parameters were: sample flow rate of 1 mL/min, column temperature of 80° C., column pressure of 60-70 bar, mobile phase composition of 97.9% water/1.9% acetonitrile with 0.2% trifluoroacetic acid; UV wavelength for analysis of 214.4 nm, injection volume of 10 μL, and sample run time of 10 minutes.

Under these conditions, the truncated jellyfish collation of SEQ ID NO: 5 has an elution time of about 5.4 minutes. ChemStation quantifies the peak area of the elution peak and calculates the protein concentration using a calibration curve that directly relates peak area to protein concentration. The calibration curve is generated using a known collagen solution that is serially diluted to contain collagen concentration ranges of 0.06 mg/mL to 1.00 mg/mL.

Truncated Collagen Without His Tag-Linker-Thrombin Cleavage Site

A truncated jellyfish collagen without a His tag, linker, and thrombin cleavage site is disclosed below. The codon-optimized nucleotide sequence encoding this collagen is provided in SEQ ID NO: 6. The amino acid sequence is disclosed in SEQ ID NO: 7. The DsbA secretion tag is encoded by nucleotides 1-72 of SEQ ID NO: 6 and encodes amino acids 1-24 of SEQ ID NO: 7. The truncated collagen sequence is encoded by nucleotides 73-639 of SEQ ID NO: 6 and encodes amino acids 25-213 of SEQ ID NO: 7.

```
                                             (SEQ ID NO: 6)
ATGAAAAAGATTTGGCTGGCGCTGGCTGGTTTAGTTTTAGCGTTTAGCGC

ATCGGCGGCGCAGTATGAAGATGGTCCGCAGGGTGTTGTTGGTGCAGATG

GTAAAGACGGTACCCCGGGTAATGCAGGTCAGAAAGGTCCGTCAGGTGAA

CCTGGCAGCCCTGGTAAAGCAGGTAGTGCCGGTGAGCAGGGTCCGCCGGG

CAAAGATGGTAGTAATGGTGAGCCGGGTAGCCCTGGCAAAGAAGGTGAAC

GTGGTCTGGCAGGACCGCCGGGTCCTGATGGTCGCCGCGGTGAAACGGGT

TCACCGGGTATTGCCGGTGCCCTGGGTAAACCAGGTCTGGAAGGTCCGAA

AGGTTATCCTGGTCTGCGCGGTCGTGATGGTACCAATGGCAAACGTGGCG

AACAGGGCGAAACCGGTCCAGATGGTGTTCGTGGTATTCCGGGTAACGAT

GGTCAGAGCGGTAAACCGGGCATTGATGGTATTGATGGCACCAATGGTCA

GCCTGGCGAAGCAGGTTATCAGGGTGGTCGCGGTACCCGTGGTCAGCTGG

GTGAAACAGGTGATGTTGGTCAGAATGGTGATCGCGGCGCACCGGGTCCG

GATGGTAGCAAAGGTAGCGCCGGTCGTCCGGGTTTACGTTAA

                                             (SEQ ID NO: 7)
MKKIWLALAGLVLAFSASAAQYEDGPQGVVGADGKDGTPGNAGQKGPSGE

PGSPGKAGSAGEQGPPGKDGSNGEPGSPGKEGERGLAGPPGPDGRRGETG

SPGIAGALGKPGLEGPKGYPGLRGRDGTNGKRGEQGETGPDGVRGIPGND
```

-continued

```
GQSGKPGIDGIDGTNGQPGEAGYQGGRGTRGQLGETGDVGQNGDRGAPGP

DGSKGSAGRPGLR
```

A polynucleotide encoding a truncated jellyfish collagen without a His tag, linker and thrombin cleavage site is disclosed in SEQ ID NO: 8.

```
                                             (SEQ ID NO: 8)
GGTCCGCAGGGTGTTGTTGGTGCAGATGGTAAAGACGGTACCCCGGGTAA

TGCAGGTCAGAAAGGTCCGTCAGGTGAACCTGGCAGCCCTGGTAAAGCAG

GTAGTGCCGGTGAGCAGGGTCCGCCGGGCAAAGATGGTAGTAATGGTGAG

CCGGGTAGCCCTGGCAAAGAAGGTGAACGTGGTCTGGCAGGACCGCCGGG

TCCTGATGGTCGCCGCGGTGAAACGGGTTCACCGGGTATTGCCGGTGCCC

TGGGTAAACCAGGTCTGGAAGGTCCGAAAGGTTATCCTGGTCTGCGCGGT

CGTGATGGTACCAATGGCAAACGTGGCGAACAGGGCGAAACCGGTCCAGA

TGGTGTTCGTGGTATTCCGGGTAACGATGGTCAGAGCGGTAAACCGGGCA

TTGATGGTATTGATGGCACCAATGGTCAGCCTGGCGAAGCAGGTTATCAG

GGTGGTCGCGGTACCCGTGGTCAGCTGGGTGAAACAGGTGATGTTGGTCA

GAATGGTGATCGCGGCGCACCGGGTCCGGATGGTAGCAAAGGTAGCGCCG

GTCGTCCGGGTTTACGTTAA
```

A truncated jellyfish collagen without a His tag, linker, and thrombin cleavage site is disclosed in SEQ ID NO: 5.

```
                                             (SEQ ID NO: 5)
GPQGVVGADGKDGTPGNAGQKGPSGEPGSPGKAGSAGEQGPPGKDGSNGE

PGSPGKEGERGLAGPPGPDGRRGETGSPGIAGALGKPGLEGPKGYPGLRG

RDGTNGKRGEQGETGPDGVRGIPGNDGQSGKPGIDGIDGTNGQPGEAGYQ

GGRGTRGQLGETGDVGQNGDRGAPGPDGSKGSAGRPGLR
```

Truncated Collagen with DsbA Secretion Tag-His Tag-Linker-Thrombin Cleavage Site and GFP Beta-Lactamase Fusion (Version 1):

A jellyfish collagen with DsbA secretion tag-His tag-Linker-Thrombin cleavage site and GFP Beta-lactamase fusion is disclosed below. The codon-optimized nucleotide sequence encoding this collagen is provided in SEQ ID NO: 9. The amino acid sequence is disclosed in SEQ ID NO: 10. The DsbA secretion tag is encoded by nucleotides 1-72 of SEQ ID NO: 9 and encodes amino acids 1-24 of SEQ ID NO: 10. The His tag is encoded by nucleotides 73-99 of SEQ ID NO: 9 and encodes a 9 histidine tag of amino acids 25-33 of SEQ ID NO: 10. The linker is encoded by nucleotides 100-111 of SEQ ID NO: 9 and encodes amino acids 34-37 of SEQ ID NO: 10. The thrombin cleavage side is encoded by nucleotides 112-135 of SEQ ID NO: 9 and encodes amino acids 38-45 of SEQ ID NO: 10. The green fluorescent protein (GFP) with linker is encoded by nucleotides 136-873 of SEQ ID NO: 9 and encodes amino acids 46-291 of SEQ ID NO: 10. The truncated collagen sequence is encoded by nucleotides 874-1440 of SEQ ID NO: 9 and encodes amino acids 292-480 of SEQ ID NO: 10. The Beta-lactamase with linker is encoded by nucleotides 1441-2232 of SEQ ID NO: 9 and encodes amino acids 481-744 of SEQ ID NO: 10. The Beta-lactamase was properly targeted to the periplasmic space even though the polypeptide did not have an independent secretion tag. The DsbA secretion tag directed the entire transcript (Truncated Collagen with DsbA secretion tag-His tag-Linker-Thrombin cleavage site and GFP Beta-lactamase fusion protein) to the periplasmic space and the Beta-lactamase functioned properly.

(SEQ ID NO: 9)

```
ATGAAAAAGATTTGGCTGGCGCTGGCTGGTTTAGTTTTAGCGTTTAGCGC
ATCGGCGGCGCAGTATGAAGATCACCATCACCACCACCACCATCACCACT
CTGGCTCGAGCCTGGTGCCGCGCGGCAGCCATATGTCTGGCTCGAGCAGT
AAAGGTGAAGAACTGTTCACCGGTGTTGTTCCGATCCTGGTTGAACTGGA
TGGTGATGTTAACGGCCACAAATTCTCTGTTCGTGGTGAAGGTGAAGGTG
ATGCAACCAACGGTAAACTGACCCTGAAATTCATCTGCACTACCGGTAAA
CTGCCGGTTCCATGGCCGACTCTGGTGACTACCCTGACCTATGGTGTTCA
GTGTTTTTCTCGTTACCCGGATCACATGAAGCAGCATGATTTCTTCAAAT
CTGCAATGCCGGAAGGTTATGTACAGGAGCGCACCATTTCTTTCAAAGAC
GATGGCACCTACAAAACCCGTGCAGAGGTTAAATTTGAAGGTGATACTCT
GGTGAACCGTATTGAACTGAAAGGCATTGATTTCAAAGAGGACGGCAACA
TCCTGGGCCACAAACTGGAATATAACTTCAACTCCCATAACGTTTACATC
ACCGCAGACAAACAGAAGAACGGTATCAAAGCTAACTTCAAAATTCGCCA
TAACGTTGAAGACGGTAGCGTACAGCTGGCGGACCACTACCAGCAGAACA
CTCCGATCGGTGATGGTCCGGTTCTGCTGCCGGATAACCACTACCTGTCC
ACCCAGTCTAAACTGTCCAAAGACCCGAACGAAAAGCGCGACCACATGGT
GCTGCTGGAGTTCGTTACTGCAGCAGGTATCACGCACGGCATGGATGAAC
TCTACAAATCTGGCGCGCCGGGCGGTCCGCAGGGTGTTGTTGGTGCAGAT
GGTAAAGACGGTACCCCGGGTAATGCAGGTCAGAAAGGTCCGTCAGGTGA
ACCTGGCAGCCCTGGTAAAGCAGGTAGTGCCGGTGAGCAGGGTCCGCCGG
GCAAAGATGGTAGTAATGGTGAGCCGGGTAGCCCTGGCAAAGAAGGTGAA
CGTGGTCTGGCAGGACCGCCGGGTCCTGATGGTCGCCGCGGTGAAACGGG
TTCACCGGGTATTGCCGGTGCCCTGGGTAAACCAGGTCTGGAAGGTCCGA
AAGGTTATCCTGGTCTGCGCGGTCGTGATGGTACCAATGGCAAACGTGGC
GAACAGGGCGAAACCGGTCCAGATGGTGTTCGTGGTATTCCGGGTAACGA
TGGTCAGAGCGGTAAACCGGGCATTGATGGTATTGATGGCACCAATGGTC
AGCCTGGCGAAGCAGGTTATCAGGGTGGTCGCGGTACCCGTGGTCAGCTG
GGTGAAACAGGTGATGTTGGTCAGAATGGTGATCGCGGCGCACCGGGTCC
GGATGGTAGCAAAGGTAGCGCCGGTCGTCCGGGTTTACGTCACCCAGAAA
CGCTGGTGAAAGTAAAAGATGCTGAAGATCAGTTGGGTGCACGAGTGGGT
TACATCGAACTGGATCTCAACAGCGGTAAGATCCTTGAGAGTTTTCGCCC
CGAAGAACGTTTTCCAATGATGAGCACTTTTAAAGTTCTGCTATGTGGCG
CGGTATTATCCCGTATTGACGCCGGGCAAGAGCAACTCGGTCGCCGCATA
CACTATTCTCAGAATGACTTGGTTGAGTACTCACCAGTCACAGAAAAGCA
TCTTACGGATGGCATGACAGTAAGAGAATTATGCAGTGCTGCCATAACCA
TGAGTGATAACACTGCGGCCAACTTACTTCTGACAACGATCGGAGGACCG
AAGGAGCTAACCGCTTTTTTGCACAACATGGGGGATCATGTAACTCGCCT
```

-continued

```
TGATCGTTGGGAACCGGAGCTGAATGAAGCCATACCAAACGACGAGCGTG
ACACCACGATGCCTGTAGCAATGGCAACAACGTTGCGCAAACTATTAACT
GGCGAACTACTTACTCTAGCTTCCCGGCAACAATTAATAGACTGGATGGA
GGCGGATAAAGTTGCAGGACCACTTCTGCGCTCGGCCCTTCCGGCTGGCT
GGTTTATTGCTGATAAATCTGGAGCCGGTGAGCGTGGGTCTCGCGGTATC
ATTGCAGCACTGGGGCCAGATGGTAAGCCCTCCCGTATCGTAGTTATCTA
CACGACGGGGAGTCAGGCAACTATGGATGAACGAAATAGACAGATCGCTG
AGATAGGTGCCTCACTGATTAAGCATTGGTAA
```

(SEQ ID NO: 10)

```
MKKIWLALAGLVLAFSASAAQYEDHHHHHHHHHSGSSLVPRGSHMSGSSS
KGEELFTGVVPILVELDGDVNGHKFSVRGEGEGDATNGKLTLKFICTTGK
LPVPWPTLVTTLTYGVQCFSRYPDHMKQHDFFKSAMPEGYVQERTISFKD
DGTYKTRAEVKFEGDTLVNRIELKGIDFKEDGNILGHKLEYNFNSHNVYI
TADKQKNGIKANFKIRHNVEDGSVQLADHYQQNTPIGDGPVLLPDNHYLS
TQSKLSKDPNEKRDHMVLLEFVTAAGITHGMDELYKSGAPGGPQGVVGAD
GKDGTPGNAGQKGPSGEPGSPGKAGSAGEQGPPGKDGSNGEPGSPGKEGE
RGLAGPPGPDGRRGETGSPGIAGALGKPGLEGPKGYPGLRGRDGTNGKRG
EQGETGPDGVRGIPGNDGQSGKPGIDGIDGTNGQPGEAGYQGGRGTRGQL
GETGDVGQNGDRGAPGPDGSKGSAGRPGLRHPETLVKVKDAEDQLGARVG
YIELDLNSGKILESFRPEERFPMMSTFKVLLCGAVLSRIDAGQEQLGRRI
HYSQNDLVEYSPVTEKHLTDGMTVRELCSAAITMSDNTAANLLLTTIGGP
KELTAFLHNMGDHVTRLDRWEPELNEAIPNDERDTTMPVAMATTLRKLLT
GELLTLASRQQLIDWMEADKVAGPLLRSALPAGWFIADKSGAGERGSRGI
IAALGPDGKPSRIVVIYTTGSQATMDERNRQIAEIGASLIKHW
```

The polynucleotide of SEQ ID NO: 9 was constructed by assembling several DNA fragments. The collagen containing sequence was codon optimized and synthesized by Gen9 DNA (now Ginkgo Bioworks) internal synthesis. The GFP was also synthesized by Gen9. The Beta-lactamase was cloned out of the plasmid pKD46 (cgsc2.biology.yale.edu/Strain.php?ID=68099) using PCR with the enzyme PrimeSTAR® GXL polymerase (www.clontech.com/US/Products/PCR/GC_Rich/PrimeSTAR_GXL_DNA_Polymerase?sitex=1002 0:22372:US). Overlaps between the pET28 vector, GFP, Collagen, and Beta-lactamase was designed to be between 30 and 40 bp long and added using PCR with the enzyme PrimeSTAR® GXL polymerase. The opened pET28a vector and inserts were then assembled together into the final plasmid using SGI Gibson Assembly® (us.vwr.com/store/product/17613857/gibson-assembly-hifi-1-step-kit-synthetic-genomics-inc). The plasmid sequence was then verified through Sanger sequencing through Eurofins Genomics (www.eurofinsgenomics.com).

The transformed cells were cultivated in minimal media and frozen in 1.5 ml aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH 7 with Dissolved Oxygen maintained at 20% saturation using a cascade containing agitation, air, and oxygen. pH was controlled using 28% w/w ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25° C. High density culture was induced for protein production using 1 mM IPTG. Fermentation was continued for another 20-24 hours and cells were harvested using a bench top centrifuge at 9000 rcf, 15° C. for 60 minutes. Cell pellet recovered from centrifugation was resuspended in a buffer containing 0.5 M NaCl and 0.1 M KH2PO4 at pH 8 in a weight by weight ratio of 2× buffer to 1× cells.

The harvested cells were disrupted in a homogenizer at 14,000 psi pressure in 2 passes. The resulting slurry contained the collagen protein along with other proteins.

The collagen was purified by acid treatment of non-homogenized whole cells recovered from the bioreactor after centrifugation and resuspension in the buffer described above. The pH of the resuspended suspension was decreased to 3 using 6 M Hydrochloric acid. Acidified cell slurry was incubated overnight at 4° C. with mixing, followed by centrifugation. The pH was then raised to 9 using 10 N NaOH and the supernatant of the slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 $m^2$ each. Total area of filtration was 0.2 $m^2$ using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen-GFP-Beta-lactamase fusion protein was analyzed on an SDS-PAGE gel and was observed to run at an apparent molecular weight of 90 kilodaltons. The expected size of the fusion protein is 85 kDa. The 90 kDa band was confirmed by mass spectrometry to be the correct collagen fusion protein.

Truncated Collagen with DsbA Secretion Tag-His Tag-Linker-Thrombin Cleavage Site and GFP Beta-Lactamase Fusion (Version 2):

A jellyfish collagen with DsbA secretion tag-His tag-Linker-Thrombin cleavage site and GFP Beta-lactamase fusion is disclosed below. The codon-optimized nucleotide sequence encoding this collagen is provided in SEQ ID NO: 11. The amino acid sequence is disclosed in SEQ ID NO: 12. The DsbA secretion tag is encoded by nucleotides 1-72 of SEQ ID NO: 11 and encodes amino acids 1-24 of SEQ ID NO: 12. The His tag is encoded by nucleotides 73-99 of SEQ ID NO: 11 and encodes a 9 histidine tag of amino acids 25-33 of SEQ ID NO: 12. The linker is encoded by nucleotides 100-111 of SEQ ID NO: 11 and encodes amino acids 34-37 of SEQ ID NO: 12. The thrombin cleavage site is encoded by nucleotides 112-135 of SEQ ID NO: 11 and encodes amino acids 38-45 of SEQ ID NO: 12. The green fluorescent protein (GFP) with linker is encoded by nucleotides 136-873 of SEQ ID NO: 11 and encodes amino acids 46-291 of SEQ ID NO: 12. The truncated collagen sequence is encoded by nucleotides 874-1440 of SEQ ID NO: 11 and encodes amino acids 292-480 of SEQ ID NO: 12. The Beta-lactamase with linker is encoded by nucleotides 1441-2232 of SEQ ID NO: 11 and encodes amino acids 481-744 of SEQ ID NO: 12.

(SEQ ID NO: 11)

```
ATGAAAAAGATTTGGCTGGCGCTGGCTGGTTTAGTTTTAGCGTTTAGCGC

ATCGGCGGCGCAGTATGAAGATCACCATCACCACCACCACCATCACCACT

CTGGCTCGAGCCTGGTGCCGCGCGGCAGCCATATGTCTGGCTCGAGCAGT

AAAGGTGAAGAACTGTTCACCGGTGTTGTTCCGATCCTGGTTGAACTGGA

TGGTGATGTTAACGGCCACAAATTCTCTGTTCGTGGTGAAGGTGAAGGTG

ATGCAACCAACGGTAAACTGACCCTGAAATTCATCTGCACTACCGGTAAA

CTGCCGGTTCCATGGCCGACTCTGGTGACTACCCTGACCTATGGTGTTCA

GTGTTTTTCTCGTTACCCGGATCACATGAAGCAGCATGATTTCTTCAAAT

CTGCAATGCCGGAAGGTTATGTACAGGAGCGCACCATTTCTTTCAAAGAC

GATGGCACCTACAAAACCCGTGCAGAGGTTAAATTTGAAGGTGATACTCT

GGTGAACCGTATTGAACTGAAAGGCATTGATTTCAAAGAGGACGGCAACA

TCCTGGGCCACAAACTGGAATATAACTTCAACTCCCATAACGTTTACATC

ACCGCAGACAAACAGAAGAACGGTATCAAAGCTAACTTCAAAATTCGCCA

TAACGTTGAAGACGGTAGCGTACAGCTGGCGGACCACTACCAGCAGAACA

CTCCGATCGGTGATGGTCCGGTTCTGCTGCCGGATAACCACTACCTGTCC

ACCCAGTCTaaaCTGTCCAAAGACCCGAACGAAAAGCGCGACCACATGGT

GCTGCTGGAGTTCGTTACTGCAGCAGGTATCACGCACGGCATGGATGAAC

TCTACAAATCTGGCGCGCCGGGCGGTCCGCAGGGTGTTGTTGGTGCAGAT

GGTAAAGACGGTACCCCGGGTAATGCAGGTCAGAAAGGTCCGTCAGGTGA

ACCTGGCAGCCCTGGTAAAGCAGGTAGTGCCGGTGAGCAGGGTCCGCCGG

GCAAAGATGGTAGTAATGGTGAGCCGGGTAGCCCTGGCAAAGAAGGTGAA

CGTGGTCTGGCAGGACCGCCGGGTCCTGATGGTCGCCGCGGTGAAACGGG

TTCACCGGGTATTGCCGGTGCCCTGGGTAAACCAGGTCTGGAAGGTCCGA

AAGGTTATCCTGGTCTGCGCGGTCGTGATGGTACCAATGGCAAACGTGGC

GAACAGGGCGAAACCGGTCCAGATGGTGTTCGTGGTATTCCGGGTAACGA

TGGTCAGAGCGGTAAACCGGGCATTGATGGTATTGATGGCACCAATGGTC

AGCCTGGCGAAGCAGGTTATCAGGGTGGTCGCGGTACCCGTGGTCAGCTG

GGTGAAACAGGTGATGTTGGTCAGAATGGTGATCGCGGCGCACCGGGTCC

GGATGGTAGCAAAGGTAGCGCCGGTCGTCCGGGTTTACGTCACCCAGAAA

CGCTGGTGAAAGTAAAAGATGCTGAAGATCAGTTGGGTGCACGAGTGGGT

TACATCGAACTGGATCTCAACAGCGGTAAGATCCTTGAGAGTTTTCGCCC

CGAAGAACGTTTTCCAATGATGAGCACTTTTAAAGTTCTGCTATGTGGCG

CGGTATTATCCCGTATTGACGCCGGGCAAGAGCAACTCGGTCGCCGCATA

CACTATTCTCAGAATGACTTGGTTGAGTACTCACCAGTCACAGAAAAGCA

TCTTACGGATGGCATGACAGTAAGAGAATTATGCAGTGCTGCCATAACCA

TGAGTGATAACACTGCGGCCAACTTACTTCTGACAACGATCGGAGGACCG

AAGGAGCTAACCGCTTTTTTGCACAACATGGGGGATCATGTAACTCGCCT
```

-continued

TGATCGTTGGGAACCGGAGCTGAATGAAGCCATACCAAACGACGAGCGTG
ACACCACGATGCCTGTAGCAATGGCAACAACGTTGCGCAAACTATTAACT
GGCGAACTACTTACTCTAGCTTCCCGGCAACAATTAATAGACTGGATGGA
GGCGGATAAAGTTGCAGGACCACTTCTGCGCTCGGCCCTTCCGGCTGGCT
GGTTTATTGCTGATAAATCTGGAGCCGGTGAGCGTGGGTCTCGCGGTATC
ATTGCAGCACTGGGGCCAGATGGTAAGCCCTCCCGTATCGTAGTTATCTA
CACGACGGGGAGTCAGGCAACTATGGATGAACGAAATAGACAGATCGCTG
AGATAGGTGCCTCACTGATTAAGCATTGGTAA (SEQ ID NO: 12)
MKKIWLALAGLVLAFSASAAQYEDHHHHHHHHHHSGSSLVPRGSHMSGSSS
KGEELFTGVVPILVELDGDVNGHKFSVRGEGEGDATNGKLTLKFICTTGK
LPVPWPTLVTTLTYGVQCFSRYPDHMKQHDFFKSAMPEGYVQERTISFKD
DGTYKTRAEVKFEGDTLVNRIELKGIDFKEDGNILGHKLEYNFNSHNVYI
TADKQKNGIKANFKIRHNVEDGSVQLADHYQQNTPIGDGPVLLPDNHYLS
TQSKLSKDPNEKRDHMVLLEFVTAAGITHGMDELYKSGAPGGPQGVVGAD
GKDGTPGNAGQKGPSGEPGSPGKAGSAGEQGPPGKDGSNGEPGSPGKEGE
RGLAGPPGPDGRRGETGSPGIAGALGKPGLEGPKGYPGLRGRDGTNGKRG
EQGETGPDGVRGIPGNDGQSGKPGIDGIDGTNGQPGEAGYQGGRGTRGQL
GETGDVGQNGDRGAPGPDGSKGSAGRPGLRHPETLVKVKDAEDQLGARVG
YIELDLNSGKILESFRPEERFPMMSTFKVLLCGAVLSRIDAGQEQLGRRI
HYSQNDLVEYSPVTEKHLTDGMTVRELCSAAITMSDNTAANLLLTTIGGP
KELTAFLHNMGDHVTRLDRWEPELNEAIPNDERDTTMPVAMATTLRKLLT
GELLTLASRQQLIDWMEADKVAGPLLRSALPAGWFIADKSGAGERGSRGI
IAALGPDGKPSRIVVIYTTGSQATMDERNRQIAEIGASLIKHW

Example 2. Human Collagens

Truncated Human Collagen Type 21 Alpha 1

A truncated human collagen type 21 alpha 1 (truncated relative to full-length human type 21 alpha 1 collagen (SEQ ID NO: 31)) without a His tag, linker, and thrombin cleavage site is disclosed below. The codon-optimized nucleotide sequence encoding this collagen and the amino acid sequence are disclosed below. The DsbA secretion tag is encoded by nucleotides 1-72 of SEQ ID NO: 13 and encodes amino acids 1-24 of SEQ ID NO: 14. The truncated collagen sequence is encoded by nucleotides 73-633 of SEQ ID NO: 13 and encodes amino acids 25-211 of SEQ ID NO: 14.

The codon-optimized nucleotide sequence encoding this collagen is provided in SEQ ID NO: 13.

(SEQ ID NO: 13)
ATGAAAAAGATTTGGCTGGCGCTGGCTGGTTTAGTTTTAGCGTTTAGCGC
ATCGGCGGCGCAGTATGAAGATGCAGGTTTTCCGGGTCTGCCTGGTCCGG
CAGGCGAACCGGGTCGTCATGGTAAAGATGGTCTGATGGGTAGTCCGGGT
TTTAAAGGTGAAGCAGGTTCACCGGGTGCACCTGGTCAGGATGGCACCCG
TGGTGAACCGGGTATTCCGGGATTTCCGGGTAATCGTGGCCTGATGGGTC
AGAAAGGTGAAATTGGTCCGCCTGGTCAGCAGGGTAAAAAAGGCGCACCG

-continued

GGTATGCCAGGACTGATGGGTTCAAATGGCAGTCCGGGTCAGCCAGGCAC
ACCGGGTTCAAAAGGTAGCAAAGGCGAACCTGGTATTCAGGGTATGCCTG
GTGCAAGCGGTCTGAAAGGCGAGCCAGGTGCCACCGGTTCTCCGGGTGAA
CCAGGTTATATGGGTCTGCCAGGTATCCAAGGCAAAAAAGGTGATAAAGG
TAATCAGGGCGAAAAAGGCATTCAGGGCCAGAAAGGCGAAAATGGCCGTC
AGGGTATTCCAGGCCAGCAGGGCATCCAGGGTCATCATGGTGCAAAAGGT
GAACGTGGTGAAAAGGGCGAACCAGGTGTTCGTTTA

The amino acid sequence is disclosed in SEQ ID NO: 14.

(SEQ ID NO: 14)
MKKIWLALAGLVLAFSASAAQYEDAGFPGLPGPAGEPGRHGKDGLMGSPG
FKGEAGSPGAPGQDGTRGEPGIPGFPGNRGLMGQKGEIGPPGQQGKKGAP
GMPGLMGSNGSPGQPGTPGSKGSKGEPGIQGMPGASGLKGEPGATGSPGE
PGYMGLPGIQGKKGDKGNQGEKGIQGQKGENGRQGIPGQQGIQGHHGAKG
ERGEKGEPGVR

The codon-optimized nucleotide sequence encoding the truncated human collagen type 21 alpha 1 without the DsbA secretion tag collagen is provided in SEQ ID NO: 15.

(SEQ ID NO: 15)
TGCAGGTTTTCCGGGTCTGCCTGGTCCGGCAGGCGAACCGGGTCGTCATG
GTAAAGATGGTCTGATGGGTAGTCCGGGTTTTAAAGGTGAAGCAGGTTCA
CCGGGTGCACCTGGTCAGGATGGCACCCGTGGTGAACCGGGTATTCCGGG
ATTTCCGGGTAATCGTGGCCTGATGGGTCAGAAAGGTGAAATTGGTCCGC
CTGGTCAGCAGGGTAAAAAAGGCGCACCGGGTATGCCAGGACTGATGGGT
TCAAATGGCAGTCCGGGTCAGCCAGGCACACCGGGTTCAAAAGGTAGCAA
AGGCGAACCTGGTATTCAGGGTATGCCTGGTGCAAGCGGTCTGAAAGGCG
AGCCAGGTGCCACCGGTTCTCCGGGTGAACCAGGTTATATGGGTCTGCCA
GGTATCCAAGGCAAAAAAGGTGATAAAGGTAATCAGGGCGAAAAAGGCAT
TCAGGGCCAGAAAGGCGAAAATGGCCGTCAGGGTATTCCAGGCCAGCAGG
GCATCCAGGGTCATCATGGTGCAAAAGGTGAACGTGGTGAAAAGGGCGAA
CCAGGTGTTCGTtaa The amino acid sequence of truncated human collagen type 21 alpha 1 without the DsbA secretion tag is disclosed in SEQ ID NO: 16.

(SEQ ID NO: 16)
AGFPGLPGPAGEPGRHGKDGLMGSPGFKGEAGSPGAPGQDGTRGEPGIPG
FPGNRGLMGQKGEIGPPGQQGKKGAPGMPGLMGSNGSPGQPGTPGSKGSK
GEPGIQGMPGASGLKGEPGATGSPGEPGYMGLPGIQGKKGDKGNQGEKGI
QGQKGENGRQGIPGQQGIQGHHGAKGERGEKGEPGVR

The polynucleotides of SEQ ID NO: 13 were synthesized by Twist Bioscience. Overlaps between the pET28 vector and SEQ ID NO: 15 and SEQ ID NO: 16 were designed to be between 20 and 30 bp long and added using PCR with the enzyme PrimeSTAR® GXL polymerase (www.takarabio-.com/products/pcr/gc-rich-pcr/primestar-gxl-dna-polymerase). The opened pET28a vector and insert DNA (SEQ ID NO: 13) was then assembled together into the final plasmid using In-Fusion Cloning (www.takarabio.com/products/cloning/in-fusion-cloning). The plasmid sequence was then verified through Sanger sequencing through Genewiz (www.genewiz.com/en).

The transformed cells were cultivated in minimal media and frozen in 1.5 ml aliquots with vegetable glycerin at a ratio of 50:50 of cells to glycerin. One vial of this frozen culture was revived in 50 ml of minimal media overnight at 37° C., 200 rpm. Cells were transferred into 300 ml of minimal media and grown for 6-9 hours to reach an OD600 of 5-10.

Minimal media used in this example and throughout this application is prepared as follows:

1) Autoclave 5 L of 550 g/kg Glucose syrup at concentration in DI water. (VWR, product #97061-170). 2) Autoclave in 3946 mL of DI water:

20 g $(NH_4)_2HPO_4$. (VWR, product #97061-932);

66.5 g $KH_2PO_4$. (VWR, product #97062-348);

22.5 g $H_3C_6H_5O_7$. (VWR, product #BDH9228-2.5 KG);

8.85 g $MgSO_4{\cdot}7H_2O$. (VWR, product #97062-134);

10 mL of 1000× Trace metals formulation (Table 3).

After autoclaving, add 118 g of (1) to (2);

5 mL of 25 mg/mL Kanamycin Sulfate (VWR-V0408);

Use 28% $NH_4OH$ (VWR, product #BDH3022) to adjust pH to 6.1.

TABLE 3

| Trace metals formulation |
|---|
| Ferrous Sulfate Heptahydrate, 27.8 g/L (Spectrum, 7782-63-0) |
| Zinc Sulfate heptahydrate, 2.88 g/L (Spectrum, 7446-20-0) |
| Calcium chloride dihydrate, 2.94 g/L (Spectrum, 2971347) |
| Sodium molybdate dihydrate, 0.48 g/L (Spectrum, 10102-40-6) |
| Manganese chloride tetrahydrate, 1.26 g/L (Spectrum, 13446-34-9) |
| Sodium selenite, 0.35 g/L (Spectrum, 10102-18-8) |
| Boric acid, 0.12 g/L (Spectrum, 10043-35-3 |

The fermentations were performed at various temperature ranging from 25° to 28° C. For some fermentations, the temperature of the fermentation was maintained at a constant temperature and immediately upon completion of fermentation the collagen was purified. For other fermentations, the temperature of the fermentations was maintained for a desired period of time and when cell densities of OD600 of 10-20 were reached, the temperature was reduced to induce protein production. Typically, the temperature was reduced from 28° C. to 25° C. After the fermentation at 25° C. was continued for 40-60 hours.

The collagen was purified as follows: The pH of the fermentation broth was decreased to between 3-3.5 using 5-50% Sulfuric Acid. The cells were then separated using centrifugation. Supernatant of the acidified broth was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 $m^2$ each. Total area of filtration was 0.2 $m^2$ using 2 cassettes in parallel. A volume reduction of 5× and a salt reduction of 19× was achieved in the TFF stage. Final collagen slurry was run on an SDS-PAGE gel to confirm presence of the collagen.

The purified collagen was analyzed on an SDS-PAGE gel and a thick and clear band was observed at the expected size of 25 kilodaltons. Quantification of collagen titers and purity were conducted using reverse phase and size exclusion HPLC chromatography. Titers are usually between 3 to 8 grams per liter. The purified collagen was also further analyzed by mass spectrometry and it was confirmed to match the published sequence of human type 21 collagen.

Truncated Human Collagen Type 1 Alpha 2 (1)

A truncated human collagen type 1 alpha 2 (truncated relative to full-length human collagen type 1 alpha 2 (SEQ ID NO: 32)) without a His tag, linker, and thrombin cleavage site is disclosed below. The codon-optimized nucleotide sequence and the amino acid sequences are disclosed below. The DsbA secretion tag is encoded by nucleotides 1-72 of SEQ ID NO: 17 and encodes amino acids 1-24 of SEQ ID NO: 18. The truncated collagen sequence is encoded by nucleotides 73-636 of SEQ ID NO: 17 and encodes amino acids 25-212 of SEQ ID NO: 18.

The codon-optimized nucleotide sequence encoding this collagen is provided in SEQ ID NO: 17.

(SEQ ID NO: 17)

```
ATGAAAAAGATTTGGCTGGCGCTGGCTGGTTTAGTTTTAGCGTTTAGCGC
ATCGGCGGCGCAGTATGAAGATATGGGTCCGCCTGGTAGCCGTGGTGCAA
GTGGTCCGGCAGGCGTTCGTGGTCCGAATGGTGATGCAGGTCGTCCGGGT
GAACCGGGTCTGATGGGTCCTCGTGGTCTGCCTGGTTCACCGGGTAATAT
TGGTCCTGCAGGTAAAGAAGGTCCGGTTGGTCTGCCAGGTATTGATGGCC
GTCCGGGTCCGATTGGTCCAGCCGGTGCACGTGGTGAACCTGGCAATATT
GGTTTTCCGGGTCCTAAAGGTCCGACCGGTGATCCGGGTAAAAATGGTGA
TAAAGGTCATGCAGGTCTGGCAGGCGCACGCGGTGCACCTGGTCCGGATG
GTAATAATGGTGCACAGGGTCCACCGGGTCCGCAGGGTGTTCAAGGTGGT
AAAGGCGAACAGGGTCCTGCCGGTCCTCCGGGTTTTCAGGGACTGCCTGG
TCCGAGCGGTCCTGCGGGTGAAGTTGGTAAACCTGGTGAACGCGGTCTGC
ATGGTGAATTTGGCCTGCCTGGGCCTGCAGGTCCGCGTGGCGAACGTGGT
CCGCCAGGTGAAAGCGGTGCAGCAGGTCCGACAGGTTAA
```

The amino acid sequence is disclosed in SEQ ID NO: 18.

(SEQ ID NO: 18)

```
MKKIWLALAGLVLAFSASAAQYEDMGPPGSRGASGPAGVRGPNGDAGRPG
EPGLMGPRGLPGSPGNIGPAGKEGPVGLPGIDGRPGPIGPAGARGEPGNI
GFPGPKGPTGDPGKNGDKGHAGLAGARGAPGPDGNNGAQGPPGPQGVQGG
KGEQGPAGPPGFQGLPGPSGPAGEVGKPGERGLHGEFGLPGPAGPRGERG
PPGESGAAGPTG
```

The nucleic acid sequence of truncated human collagen type 1 alpha 2 (1) without the DsbA secretion tag is disclosed in SEQ ID NO: 19.

(SEQ ID NO: 19)

```
ATGGGTCCGCCTGGTAGCCGTGGTGCAAGTGGTCCGGCAGGCGTTCGTGG
TCCGAATGGTGATGCAGGTCGTCCGGGTGAACCGGGTCTGATGGGTCCTC
GTGGTCTGCCTGGTTCACCGGGTAATATTGGTCCTGCAGGTAAAGAAGGT
```

-continued

```
CCGGTTGGTCTGCCAGGTATTGATGGCCGTCCGGGTCCGATTGGTCCAGC

CGGTGCACGTGGTGAACCTGGCAATATTGGTTTTCCGGGTCCTAAAGGTC

CGACCGGTGATCCGGGTAAAAATGGTGATAAAGGTCATGCAGGTCTGGCA

GGCGCACGCGGTGCACCTGGTCCGGATGGTAATAATGGTGCACAGGGTCC

ACCGGGTCCGCAGGGTGTTCAAGGTGGTAAAGGCGAACAGGGTCCTGCCG

GTCCTCCGGGTTTTCAGGGACTGCCTGGTCCGAGCGGTCCTGCGGGTGAA

GTTGGTAAACCTGGTGAACGCGGTCTGCATGGTGAATTTGGCCTGCCTGG

GCCTGCAGGTCCGCGTGGCGAACGTGGTCCGCCAGGTGAAAGCGGTGCAG

CAGGTCCGACAGGTTAA
```

The amino acid sequence of truncated human collagen type 1 alpha 2 (1) without the DsbA secretion tag is disclosed in SEQ ID NO: 20.

```
                                          (SEQ ID NO: 20)
MGPPGSRGASGPAGVRGPNGDAGRPGEPGLMGPRGLPGSPGNIGPAGKEG

PVGLPGIDGRPGPIGPAGARGEPGNIGFPGPKGPTGDPGKNGDKGHAGLA

GARGAPGPDGNNGAQGPPGPQGVQGGKGEQGPAGPPGFQGLPGPSGPAGE

VGKPGERGLHGEFGLPGPAGPRGERGPPGESGAAGPTG
```

Truncated Human Collagen Type 1 Alpha 2 (2)

A truncated human collagen type 1 alpha 2 (truncated relative to full-length human collagen type 1 alpha 2 (SEQ ID NO: 32)) without a His tag, linker, and thrombin cleavage site is disclosed below. The codon-optimized nucleotide sequence and the amino acid sequences are disclosed below. The DsbA secretion tag is encoded by nucleotides 1-72 of SEQ ID NO: 21 and encodes amino acids 1-24 of SEQ ID NO: 22. The truncated collagen sequence is encoded by nucleotides 73-609 of SEQ ID NO: 21 and encodes amino acids 25-203 of SEQ ID NO: 22.

The codon-optimized nucleotide sequence encoding this collagen is provided in SEQ ID NO: 21.

```
                                          (SEQ ID NO: 21)
ATGAAAAAGATTTGGCTGGCGCTGGCTGGTTTAGTTTTAGCGTTTAGCGC

ATCGGCGGCGCAGTATGAAGATGGTTTTCAGGGTCCTGCCGGTGAACCGG

GTGAACCTGGTCAGACAGGTCCGGCAGGCGCACGTGGTCCTGCAGGTCCT

CCTGGTAAAGCCGGTGAAGATGGTCATCCGGGTAAACCGGGTCGTCCTGG

TGAACGTGGTGTTGTTGGTCCGCAGGGTGCCCGTGGTTTTCCGGGTACTC

CGGGTCTGCCAGGTTTTAAAGGTATTCGTGGTCATAATGGTCTGGATGGT

CTGAAAGGTCAGCCTGGTGCACCGGGTGTTAAAGGTGAACCAGGTGCTCC

GGGTGAAAATGGCACACCGGGTCAGACCGGTGCGCGTGGTCTGCCTGGCG

AACGCGGTCGTGTTGGTGCACCTGGTCCAGCCGGTGCACGCGGTAGTGAT

GGTAGCGTTGGTCCGGTTGGTCCAGCGGGTCCGATTGGTAGCGCAGGTCC

ACCGGGTTTTCCAGGCGCACCGGGTCCGAAAGGTGAAATTGGTGCAGTTG

GTAATGCAGGCCCTGCCGGTCCAGCAGGACCGCGTGGTGAAGTTGGCCTG

CCTGGTCTGTAA
```

The amino acid sequence is disclosed in SEQ ID NO: 22.

```
                                          (SEQ ID NO: 22)
MKKIWLALAGLVLAFSASAAQYEDGFQGPAGEPGEPGQTGPAGARGPAGP

PGKAGEDGHPGKPGRPGERGVVGPQGARGFPGTPGLPGFKGIRGHNGLDG

LKGQPGAPGVKGEPGAPGENGTPGQTGARGLPGERGRVGAPGPAGARGSD

GSVGPVGPAGPIGSAGPPGFPGAPGPKGEIGAVGNAGPAGPAGPRGEVGL

PGL
```

The nucleic acid sequence of truncated human collagen type 1 alpha 2 (2) without the DsbA secretion tag is disclosed in SEQ ID NO: 23.

```
                                          (SEQ ID NO: 23)
GGTTTTCAGGGTCCTGCCGGTGAACCGGGTGAACCTGGTCAGACAGGTCC

GGCAGGCGCACGTGGTCCTGCAGGTCCTCCTGGTAAAGCCGGTGAAGATG

GTCATCCGGGTAAACCGGGTCGTCCTGGTGAACGTGGTGTTGTTGGTCCG

CAGGGTGCCCGTGGTTTTCCGGGTACTCCGGGTCTGCCAGGTTTTAAAGG

TATTCGTGGTCATAATGGTCTGGATGGTCTGAAAGGTCAGCCTGGTGCAC

CGGGTGTTAAAGGTGAACCAGGTGCTCCGGGTGAAAATGGCACACCGGGT

CAGACCGGTGCGCGTGGTCTGCCTGGCGAACGCGGTCGTGTTGGTGCACC

TGGTCCAGCCGGTGCACGCGGTAGTGATGGTAGCGTTGGTCCGGTTGGTC

CAGCGGGTCCGATTGGTAGCGCAGGTCCACCGGGTTTTCCAGGCGCACCG

GGTCCGAAAGGTGAAATTGGTGCAGTTGGTAATGCAGGCCCTGCCGGTCC

AGCAGGACCGCGTGGTGAAGTTGGCCTGCCTGGTCTGTAA
```

The amino acid sequence of truncated human collagen type 1 alpha 2 (2) without the DsbA secretion tag is disclosed in SEQ ID NO: 24.

```
                                          (SEQ ID NO: 24)
GFQGPAGEPGEPGQTGPAGARGPAGPPGKAGEDGHPGKPGRPGERGVVGP

QGARGFPGTPGLPGFKGIRGHNGLDGLKGQPGAPGVKGEPGAPGENGTPG

QTGARGLPGERGRVGAPGPAGARGSDGSVGPVGPAGPIGSAGPPGFPGAP

GPKGEIGAVGNAGPAGPAGPRGEVGLPGL
```

The polynucleotides of SEQ ID NO: 13, 17, or 21 were subcloned in vector pET28a as described herein to prepare a transformation vector. Host cells were transformed with the vector the polynucleotides were expressed as described in Example 1.

After the fermentation was completed, the truncated human collagen was purified from the fermentation broth using the procedures disclosed in Example 2. The purified truncated human collagens were analyzed using SDS-PAGE and HPLC as disclosed in Example 2.

All three truncated human collagens ran at the expected molecular weights in the SDS-PAGE analysis. In analyzing the truncated human collagens using HPLC, a standard curve using the jellyfish collagen of Example 1 was utilized. The retention times of the human collagens were slightly different than the jellyfish collagen. The retention time of SEQ ID NO: 16 was 5.645 minutes, the retention time of SEQ ID NO: 20 was 5.631 minutes, and SEQ ID NO: 24 ran at two peaks and the retention times were 5.531 and 5.7 minutes.

Truncated Human Collagen Type 1 Alpha 2 Truncation 5 with DsbA Secretion and FLAG Tag The amino acid sequence of truncated human collagen type 1 alpha 2 truncation 5 with DsbA secretion and FLAG tag is disclosed in SEQ ID NO: 25. The DsbA secretion tag is encoded by nucleotides 1-57 of SEQ ID NO: 26 and the amino acid sequences are amino acids 1-19 of SEQ ID NO: 25. The collagen nucleotide sequences are nucleotides 58-657 of SEQ ID NO: 26 and the amino acid sequences are amino acids 20-219 of SEQ ID NO: 25. The FLAG nucleotide sequences are nucleotides 658-684 of SEQ ID NO: 26 and the amino acid sequences are amino acids 220-228 of SEQ ID NO: 25.

(SEQ ID NO: 25)

```
MKKIWLALAGLVLAFSASAGDQGPVGRTGEVGAVGPPGFAGEKGPSGEAG

TAGPPGTPGPQGLLGAPGILGLPGSRGERGLPGVAGAVGEPGPLGIAGPP

GARGPPGAVGSPGVNGAPGEAGRDGNPGNDGPPGRDGQPGHKGERGYPGN

IGPVGAAGAPGPHGPVGPAGKHGNRGETGPSGPVGPAGAVGPRGPSGPQG

IRGDKGEPGEKGPRGLPGLGDYKDDDDK
```

The nucleic acid sequence of truncated human collagen type 1 alpha 2 truncation 5 with DsbA secretion and FLAG tag is disclosed in SEQ ID NO: 26.

(SEQ ID NO: 26)

```
ATGAAAAAGATTTGGCTGGCGCTGGCTGGTTTAGTTTTAGCGTTTAGCGC

ATCGGCGGGTGATCAGGGTCCGGTTGGTCGTACCGGTGAAGTTGGTGCAG

TCGGGCCGCCGGGTTTTGCGGGTGAAAAAGGCCCGTCAGGTGAAGCAGGC

ACCGCTGGCCCTCCTGGCACGCCTGGCCCACAGGGTTTACTGGGCGCACC

TGGAATTCTGGGACTGCCGGGCAGCCGTGGAGAACGCGGTTTACCAGGTG

TTGCCGGTGCCGTTGGTGAACCTGGTCCACTGGGCATTGCAGGGCCGCCT

GGCGCACGGGGACCGCCTGGTGCTGTTGGTAGTCCGGGTGTGAATGGTGC

TCCGGGTGAAGCCGGTCGTGACGGTAATCCGGGAAATGACGGCCCGCCAG

GCCGCGATGGTCAGCCGGGTCATAAAGGTGAGCGTGGTTACCCAGGTAAT

ATTGGTCCAGTCGGTGCCGCCGGTGCGCCGGGTCCTCATGGCCCTGTCGG

TCCAGCCGGTAAACATGGTAATCGCGGTGAGACAGGTCCGTCAGGACCAG

TGGGCCCTGCTGGCGCAGTCGGTCCGCGCGGGCCGAGTGGCCCTCAGGGT

ATTCGTGGCGATAAAGGGGAACCGGGCGAAAAAGGGCCGCGGGGTCTGCC

AGGCCTGGGTGACTACAAAGACGACGACGACAAATAA
```

The polynucleotide of SEQ ID NO: 26 was subcloned into vector pET28a, expressed in host *E. coli* cells and the truncated collagen was purified as described herein. The purified collagen produced a clear band on SDS-PAGE and an anti-FLAG western was observed at around 100 kilodaltons. There were no existing bands that appear at that location on the gel in the absence of expression of this protein.

Truncated Human Collagen Type 1 Alpha 2 Truncation 6 with DsbA Secretion and FLAG Tag The amino acid sequence of truncated human collagen type 1 alpha 2 truncation 6 with DsbA secretion and FLAG tag is disclosed in SEQ ID NO: 27. The DsbA secretion tag is encoded by nucleotides 1-57 of SEQ ID NO: 28 and the amino acid sequences are amino acids 1-19 of SEQ ID NO: 27. The collagen nucleotide sequences are nucleotides 58-657 of SEQ ID NO: 28 and the amino acid sequences are amino acids 20-219 of SEQ ID NO: 27. The FLAG nucleotide sequences are nucleotides 658-684 of SEQ ID NO: 28 and the amino acid sequences are amino acids 220-228 of SEQ ID NO: 27.

(SEQ ID NO: 27)

```
MKKIWLALAGLVLAFSASAKGHNGLQGLPGIAGHHGDQGAPGSVGPAGPR

GPAGPSGPAGKDGRTGHPGTVGPAGIRGPQGHQGPAGPPGPPGPPGPPGV

SGGGYDFGYDGDFYRADQPRSAPSLRPKDYEVDATLKSLNNQIETLLTPE

GSRKNPARTCRDLRLSHPEWSSGYYWIDPNQGCTMDAIKVYCDFSTGETC

IRAQPENIPAKNWYRSSKDGDYKDDDDK
```

The nucleic acid sequence of truncated human collagen type 1 alpha 2 truncation 6 with DsbA secretion and FLAG tag is disclosed in SEQ ID NO: 28.

(SEQ ID NO: 28)

```
ATGAAAAAGATTTGGCTGGCGCTGGCTGGTTTAGTTTTAGCGTTTAGCGC

ATCGGCGAAAGGTCACAATGGACTGCAAGGCCTGCCAGGTATTGCAGGTC

ATCATGGTGATCAAGGTGCCCCGGGAAGCGTTGGTCCGGCGGGGCCGAGA

GGCCCTGCGGGACCTTCAGGTCCGGCAGGCAAAGATGGTCGGACAGGCCA

TCCGGGCACCGTTGGCCCTGCAGGAATTCGTGGACCGCAGGGTCATCAGG

GACCTGCTGGTCCGCCAGGTCCCCCGGGCCCTCCGGGACCACCGGGTGTT

AGTGGTGGTGGTTATGATTTTGGCTATGATGGTGATTTTTATCGTGCAGA

TCAGCCGCGTAGCGCACCGAGCCTGCGTCCTAAAGATTATGAAGTTGATG

CAACCCTGAAAAGCCTGAATAATCAGATTGAAACACTGCTGACACCGGAA

GGTAGCCGTAAAAATCCGGCCCGTACCTGTCGTGATCTGCGTCTGAGCCA

CCCGGAATGGAGCAGCGGTTATTATTGGATTGATCCGAATCAAGGTTGTA

CCATGGATGCAATTAAAGTTTATTGTGATTTTAGCACAGGTGAAACATGT

ATCCGTGCACAGCCGGAAAATATTCCGGCCAAAAATTGGTATCGTAGTAG

CAAAGATGGTGACTACAAAGACGACGACGACAAATAA
```

The polynucleotide of SEQ ID NO: 28 was subcloned into vector pET28a, expressed in host *E. coli* cells and the truncated collagen was purified as described herein. The purified collagen produced a clear band on SDS-PAGE and an anti-FLAG western was observed at around 25 kilodaltons. There were no existing bands that appear at that location on the gel in the absence of expression of this protein.

Truncated Human Collagen Type 1 Alpha 2 Truncation 7 with DsbA Secretion and FLAG Tag The amino acid sequence of truncated human collagen type 1 alpha 2 truncation 7 with DsbA secretion and FLAG tag is disclosed in SEQ ID NO: 29. The DsbA secretion tag is encoded by nucleotides 1-57 of SEQ ID NO: 30 and the amino acid sequences are amino acids 1-19 of SEQ ID NO: 29. The collagen nucleotide sequences are nucleotides 58-759 of SEQ ID NO: 30 and the amino acid sequences are amino acids 20-253 of SEQ ID NO: 29. The FLAG nucleotide sequences are nucleotides 760-786 of SEQ ID NO: 30 and the amino acid sequences are amino acids 254-262 of SEQ ID NO: 29.

(SEQ ID NO: 29)
MKKIWLALAGLVLAFSASAYEVDATLKSLNNQIETLLTPEGSRKNPARTC

RDLRLSHPEWSSGYYWIDPNQGCTMDAIKVYCDFSTGETCIRAQPENIPA

KNWYRSSKDKKHVWLGETINAGSQFEYNVEGVTSKEMATQLAFMRLLANY

ASQNITYHCKNSIAYMDEETGNLKKAVILQGSNDVELVAEGNSRFTYTVL

VDGCSKKTNEWGKTIIEYKTNKPSRLPFLDIAPLDIGGADQEFFVDIGPV

CFKGDYKDDDDK

The nucleic acid sequence of truncated human collagen type 1 alpha 2 truncation 7 with DsbA secretion and FLAG tag is disclosed in SEQ ID NO: 30.

(SEQ ID NO: 30)
TGAAAAAGATTTGGCTGGCGCTGGCTGGTTTAGTTTTAGCGTTTAGCGCA

TCGGCGTATGAAGTTGATGCAACCCTGAAAAGCCTGAATAATCAGATTGA

AACACTGCTGACACCGGAAGGTAGCCGTAAAAATCCGGCCCGTACCTGTC

GTGATCTGCGTCTGAGCCACCCGGAATGGAGCAGCGGTTATTATTGGATT

GATCCGAATCAAGGTTGTACCATGGATGCAATTAAAGTTTATTGTGATTT

TAGCACAGGTGAAACATGTATCCGTGCACAGCCGGAAAATATTCCGGCCA

AAAATTGGTATCGTAGTAGCAAAGATAAAAAACATGTGTGGCTGGGTGAA

ACCATTAATGCAGGTAGCCAGTTTGAATACAATGTTGAAGGTGTTACCAG

CAAAGAAATGGCAACACAGCTGGCATTTATGCGTCTGCTGGCAAATTATG

CAAGCCAGAATATTACATATCATTGTAAAAATAGCATTGCATATATGGAT

GAAGAAACCGGTAATCTGAAAAAAGCAGTTATTCTGCAGGGTAGCAATGA

TGTTGAACTGGTTGCCGAAGGTAATAGCCGTTTTACATATACCGTTCTGG

TTGATGGTTGTAGCAAAAAAACCAATGAATGGGGTAAAACCATCATTGAA

TATAAAACCAACAAACCGAGCCGTCTGCCGTTTCTGGATATCGCTCCGCT

GGATATTGGTGGTGCCGATCAGGAATTTTTTGTCGATATCGGTCCTGTGT

GTTTTAAAGGTGACTACAAAGACGACGACGACAAATAA

The polynucleotide of SEQ ID NO: 30 was subcloned into vector pET28a, expressed in host *E. coli* cells and the truncated collagen was purified as described herein. The purified collagen produced a clear band on SDS-PAGE and an anti-FLAG western was observed at around 30 kilodaltons. There were no existing bands that appear at that location on the gel in the absence of expression of this protein.

Example 3. Human Clinical Study of Truncated Human Type 21 Collagen

A clinical study using human subjects to determine the effects of a topical skincare product containing truncated human type 21 collagen (SEQ ID NO: 16) is performed. The research is performed according to U.S. and International standards of Good Clinical Practice (FDA and ICH guidelines) and applicable government regulations.

A base formulation (control formulation) made of water, olive oil glycereth-8 esters, glycerin, coconut alkanes, hydroxyethyl acrylate/sodium acryloyldimethyl taurate copolymer, pentylene glycol, disodium EDTA, caprylyl glycol, chlorphenesin, phenoxyethanol is prepared. A formulation containing the truncated human type 21 collagen is prepared by adding sufficient collagen to prepare a topical formulation containing 0.1% w/w collagen.

Expert Grading Assessments for Qualification and Efficacy

Visual Analog Scales (VAS) are commonly used in clinical research to measure intensity or frequency of various symptoms, subjective characteristics or attitudes that cannot be directly measured. VAS are a reliable scale and more sensitive to small changes than simple ordinal scales. (A. Paul-Dauphin, F. Guillemin, J. Virion and S. Briancon, "Bias and precision in visual analog scales: A randomized controlled trial," American Journal of Epidemiology, vol. 150, no. 10, pp. 1117-27, 1999). When responding to a VAS item, the expert grader specifies their level of agreement to a statement by indicating a position along a line (10 cm) between two end-points or anchor responses. Simple VAS is used to evaluate efficacy parameters in which the ends of a 10 cm horizontal line is defined as extreme limits orientated from the left (best) to the right (worst). Signs of photo-aging can be classified as follows: Mild=1-3.9 cm, Moderate=4-6.9 cm, Severe=7-10 cm.

The VAS shown in FIG. 18 was used.

Ordinal scales allow a number to be directly and objectively attached to the quality of a given attribute. When responding to an ordinal scale item, the expert grader specifies their level of agreement to a statement by choosing a set grade, or level.

The appearance of each subject's facial skin redness (erythema) is assessed by an expert grader using the following five-point ordinal scale for qualification at Baseline (Table 4). If qualified, each subject will undergo further erythema assessments at week 2, week 4, week 6 and week 8.

TABLE 4

Five-point ordinal scale for erythema assessment
Erythema

| Grade | Description |
|---|---|
| 0 | No erythema |
| 1 | Very slight erythema (barely perceptible) |
| 2 | Well-defined erythema |
| 3 | Moderate to severe erythema |
| 4 | Severe erythema (beet redness) to slight eschar formation (injuries in depth) |

The corneometer CM 820 (Courage+Khazaka, Germany) measures the relative degree of hydration of the skin surface by applying an alternating current to the skin with a closely spaced pair of electrodes and measuring the capacitance. Changes in water content of the skin change the conductance of the capacitive circuit.

The corneometer is able to detect slight changes in the hydration level reproducibly with a measurement time of only about one second. The measurement depth is small (approximately 10-20 μm of stratum corneum) which ensures assessment is not influenced by deeper skin layers.

All subjects undergo corneometer measurements of their face at baseline, immediately post-initial-application, and at weeks 2, 4, and 8. Measurements will be taken in triplicate and averaged for each time point. Measurement location is recorded on a face map for assessment consistency at each time point.

The Cutometer MPA 580 (Courage+Khazaka, Germany) measures the viscoelastic properties of the skin by applying suction to the skin surface, drawing the skin into the aperture of the probe and determining the penetration depth using an optical measuring system.

The resistance of the skin to be sucked up by the negative pressure (firmness) and its ability to return to its original position (elasticity) are calculated and displayed as curves. The Cutometer outputs include many parameters of different portions of the measurement curve including of R0 (Uf, firmness), R2 (Ua/Uf, gross elasticity), R5 (Ur/Ue, net elasticity), R7 (Ur/Uf, elastic portion) and R9 (R3 [last max amp]−R0 [Uf], fatigue).

All subjects have Cutometer measurements taken on the left or right cheek (following a prepared randomization code) at baseline, immediately post-initial-application, and at weeks 2, 4, and 8. Skin elasticity is reported using the R5 (Ur/Ue) and R2 (Ua/Uf) parameter. As the skin becomes more elastic, this value will increase. Skin Firmness is reported using the R0 (Uf) parameter. As the skin becomes firmer, this value will decrease. Assessment location is recorded on a face map for each subject for consistency of measurements between visits.

The COSMETRICS™ SIAScope (Astron Clinica, Toft, UK) is a non-invasive optical skin imaging instrument using Spectrophotometric Intracutaneous Analysis (SIA), or chromophore mapping. The technique is based on a unique combination of dermatoscopy and contact remittance spectrophotometry. The hardware consists of a hand-held imaging probe attached to a laptop computer. The unit is placed in contact with the skin surface and high-intensity LED's illuminate the skin as discreet wavelengths of 400 to 1000 nm, spanning the visible spectrum and a small range of the near infrared spectrum. A digital image is captured for each wavelength. Three parametric chromophore maps are retrieved up to 2 mm in depth and 11 mm in circumference, one for each of the following parameters: epidermal melanin, dermal hemoglobin and dermal collagen.

For the purposes of this study, dermal collagen will be measured on the left or right cheek, per a prepared randomization code, at baseline and at weeks 2, 4; and 8. Assessment location will be recorded on a face map for each subject for consistency of measurements between visits.

The DermaScan C USB (Cortex Technology ApS, Hadsund, Denmark) is a compact high resolution ultrasound scanner. The 20 MHz, high definition 60×150 μm, 13 mm penetration probe is used which provides linear scanning, high precision operation and true position detection for image clarity and definition The instrument is provided by cyberDERM, Inc. (Broomall, PA, USA). All subjects have ultrasound assessments taken on the face at baseline and at weeks 2, 4, and 8. The location of assessments is the same at each visit and will be recorded on a face map. Upon acquisition of the ultrasound scans, they are sent to cyberDERM, Inc., for analysis of dermal thickness (density).

All clinical photography is performed in accordance with IRSI's SOP to ensure reproducibility of high quality images throughout the duration of the study. Imaging is conducted in a designated photography suite with a matte black wall and all natural light is blocked out. To prepare subjects for clinical photography, subjects are asked to remove all jewelry, including earrings, necklaces, and any facial jewelry. A trained technician inspects the subjects under a lighted magnification loop to ensure no residual color cosmetics or skincare products are visible on the face, eyes, or lips. Subjects are provided with a black cape and black headband and are instructed on placement to ensure all hair is pulled back neatly and covered.

The Clarity™ 2D Research System Ti (Clarity) (BrighTex Bio-Photonics (BTBP), San Jose CA, USA) captures high quality full face frontal, left, and right lateral images. Three cameras within the system allow for 18 megapixel SLR image capture in 16-bit simultaneously using a live feed display and automated facial alignment checks against baseline images for reproducibility.

Multi-spectral lighting (diffuse white light, cross-polarized, blue and parallel polarized) reveals skin conditions on and beneath the skin's surface layer. The system uses skin feature recognition to apply automated skin segmentation and zone mapping to allow for subsequent skin analysis. Images are analyzed for attributes associated with pigmentation, subsurface pigmentation, radiance, skin color, redness, wrinkles, skin texture, pores, acne, and/or lips.

All subjects have front, left, and right view facial images captured in standard light and parallel polarized light at baseline and at weeks 2, 4, and 8.

Subjective questionnaires allow the Sponsor to gauge the subjects' opinions of their skin, the test product, and its effects. Questions will ask for subjects' agreement to a statement with a five-point scale as well as open-ended response.

Fourteen female subjects are enrolled. The inclusion criteria are Caucasian female subjects with Fitzpatrick skin type III in good general health, and between ages of 35 and 65 years old, inclusive at enrollment. Inclusion criteria also include signs of aging on face as determined by an expert grader at a baseline of: a) Score of ≥2 cm≤6 on 10 cm scale for lines/wrinkles; and b) Score of ≥1≤3 on 5-point ordinal scale for facial redness (erythema). Table 5 discloses the demographics of the study participants.

TABLE 5

| Demographics | | | | |
|---|---|---|---|---|
| Variable | n | Mean ± SD | Min | Max |
| Age (years) | 14 | 57.64 ± 6.03 | 45 | 65 |
| Height (inches) | 14 | 63.35 ± 2.37 | 60 | 68 |
| Weight (pounds) | 14 | 160.14 ± 38.26 | 110 | 250 |
| | | | n | Percent |
| Ethnicity | 14 | Not Hispanic or Latino | 14 | 100% |
| Race | 14 | White | 14 | 100% |
| Fitzpatrick Skin Type | 14 | Skin Type III | 14 | 100% |
| Facial Skin Type | 14 | Combination | 8 | 57.1% |
| | | Normal | 6 | 42.9% |

The results of the expert clinical grader evaluation on lines/wrinkles, firmness (visual), elasticity (tactile), brightness, texture/softness (tactile), texture/smoothness (visual) and erythema after two weeks treatment are shown in Table 6. All of the tested characteristics were improved. The scores for brightness, texture/softness (tactile), texture/smoothness (visual) and erythema improved with statistical significance.

TABLE 6

| Expert Clinical Grader Evaluation - Monadic, Comparison to Baseline | | | | | | |
|---|---|---|---|---|---|---|
| Assessment | Time Point | n | Mean ± SD | Mean Percent Improvement From BL mean | Percent of Subjects Showing Improvement From BL | P-Value TX vs. BL |
| Lines/ | Baseline | 14 | 5.22 ± 0.75 | | | |
| Wrinkles | Week 2 | 14 | 5.17 ± 0.75 | 0.92% | 57.1% | 0.336 |
| (Global) | | | | | | |
| Firmness | Baseline | 14 | 5.07 ± 0.77 | | | |
| (Visual) | Week 2 | 14 | 5.01 ± 0.75 | 1.08% | 64.3% | 0.120 |
| Elasticity | Baseline | 14 | 4.91 ± 0.53 | | | |
| (Tactile) | Week 2 | 14 | 4.90 ± 0.52 | 0.25% | 35.7% | 0.547 |
| Brightness | Baseline | 14 | 5.51 ± 0.54 | | | |
| | Week 2 | 14 | 5.37 ± 0.62 | 2.57% | 78.6% | 0.010* |
| Texture/ | Baseline | 14 | 4.82 ± 0.82 | | | |
| Softness | Week 2 | 14 | 4.51 ± 0.89 | 6.43% | 71.4% | 0.008* |
| (Tactile) | | | | | | |
| Texture/ | Baseline | 14 | 5.46 ± 0.70 | | | |
| Smoothness | Week 2 | 14 | 5.25 ± 0.68 | 3.63% | 64.3% | 0.009* |
| (Visual) | | | | | | |
| Erythema | Baseline | 14 | 1.60 ± 0.73 | | | |
| | Week 2 | 14 | 1.21 ± 0.80 | 23.81% | 35.7% | 0.021* |

*Indicates a statistically significant improvement compared to baseline, p ≤ 0.05

Instrumental evaluation hydration, firmness elasticity using a corneometer and cutometer are shown in Table 7. Improvements in skin hydration, firmness, and elasticity were statistically significant. In addition, Table 7 shows the stimulation of collagen production by skin cells as demonstrated by Spectrophotometric Intracutaneous Analysis (SIA).

TABLE 7

| Instrumental Evaluation - Monadic, Comparison to Baseline | | | | | | | |
|---|---|---|---|---|---|---|---|
| Assessment | | Time Point | n | Mean ± SD | Mean Percent Improvement From BL mean | Percent of Subjects Showing Improvement From BL | p-Value TX vs. BL |
| Corneometer | | Baseline | 14 | 42.45 ± 10.06 | | | |
| | | Immediate | 14 | 57.22 ± 12.47 | 36.69% | 100% | <0.001* |
| | | Week 2 | 14 | 35.71 ± 10.77 | NI | 14.3% | 0.001** |
| Cutometer | Firmness | Baseline | 14 | 0.35 ± 0.06 | | | |
| | (R0 Uf) | Immediate | 14 | 0.24 ± 0.05 | 30.38% | 100% | <0.001* |
| | | Week 2 | 14 | 0.31 ± 0.07 | 11.27% | 78.6% | 0.028* |
| | Elasticity | Baseline | 14 | 0.64 ± 0.09 | | | |
| | (R2 Ua/Uf) | Immediate | 14 | 0.93 ± 0.13 | 45.85% | 100% | <0.001* |
| | | Week 2 | 14 | 0.80 ± 0.09 | 26.93% | 100% | <0.001* |
| | Elasticity | Baseline | 14 | 0.28 ± 0.06 | | | |
| | (R5 Ur/Ue) | Immediate | 14 | 0.40 ± 0.09 | 44.57% | 92.9% | <0.001* |
| | | Week 2 | 14 | 0.37 ± 0.08 | 33.36% | 92.9% | <0.001* |
| SIAscope | Collagen | Baseline | 14 | 238.95 ± 11.60 | | | |
| | | Week 2 | 14 | 254.89 ± 19.35 | 6.72% | 78.6% | 0.004* |

NI = No Improvement
*Indicates a statistically significant improvement compared to baseline, p ≤ 0.05
**Indicates a statistically significant worsening compared to baseline, p ≤ 0.05

The results demonstrate that truncated human type 21 collagen shows statistically significant improvements in elasticity, brightness, hydration, tactile texture, or visual texture of skin. In addition, the results show that truncated human type 21 collagen shows statistically significant decreases in visible lines or wrinkles as well as significant decreases in erythema.

Example 4. In Vitro Study of Truncated Human Type 21 Collagen on Skin Cells

Truncated Human Type 21 Alpha 1 Collagen Stimulates Fibroblast Production of Collagen Type I A series of in vitro experiments were conducted to assess the effects of a truncated human type 21 collagen on human skin fibroblasts and keratinocytes. In a first experiment, human primary fibroblasts were evaluated for collagen type I protein secretion. Fibroblasts were cultured with 0.03% of a polypeptide according to SEQ ID NO: 16 for 48 hours. Culture supernatants were analyzed by Enzyme Linked Immunosorbent Assay (ELISA) for pro-collagen type I C-peptide, which is a readout for total secreted collagen type I protein. As shown in FIG. 1, cells treated with a polypeptide of SEQ ID NO: 16 secreted higher levels of collagen type I (FIG. 1; "B") than untreated cells (FIG. 1; "A") or cells treated with retinol (FIG. 1; "C").

Figure 2A:
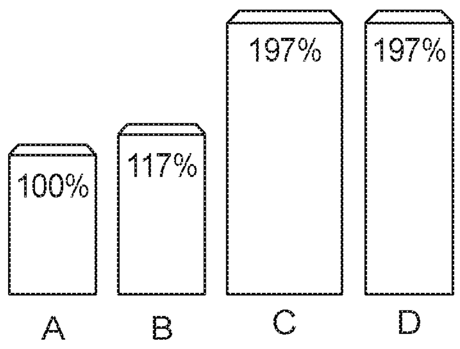
FIG. 2A illustrates expression of collagen type 1 mRNA in fibroblasts treated with an exemplary polypeptide provided herein (comprising a truncated human collagen amino acid sequence).
Figure 2B:
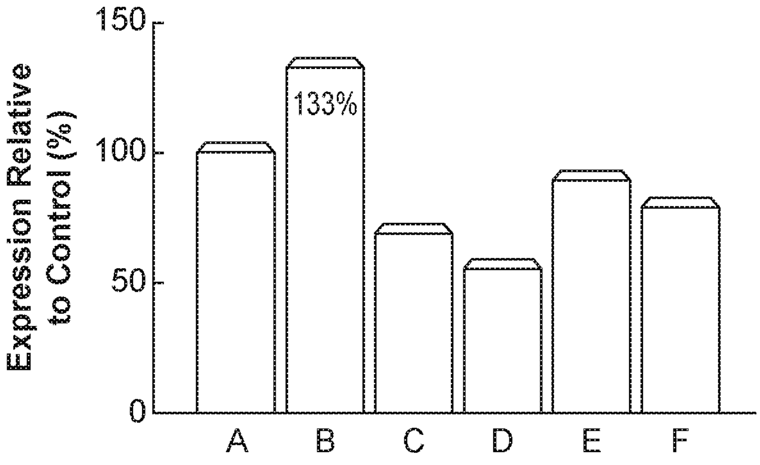
FIG. 2B illustrates expression of elastin mRNA in fibroblasts treated with an exemplary polypeptide provided herein (comprising a truncated human collagen amino acid sequence).
Figure 2C:
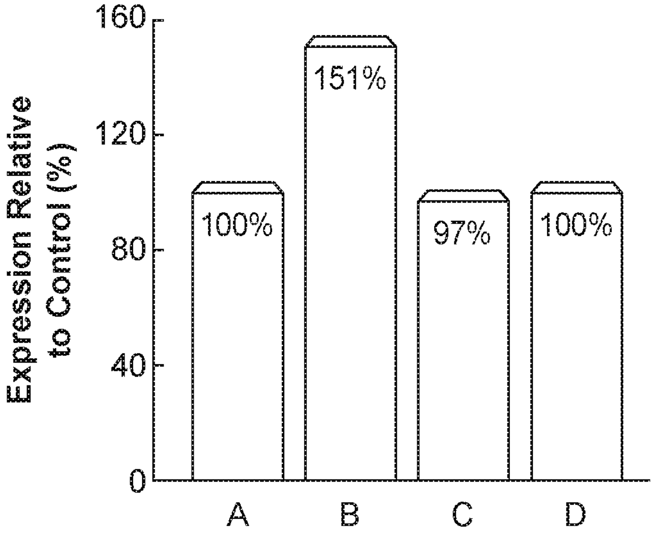
FIG. 2C illustrates expression of fibronectin mRNA in fibroblasts treated with an exemplary polypeptide provided herein (comprising a truncated human collagen amino acid sequence).

Truncated Human Type 21 Alpha 1 Collagen Stimulates Fibroblast Production of Genes for Extracellular Matrix Proteins RNA sequencing was performed to analyze global gene expression. After 48 hours of exposure, fibroblasts were incubated with 0.03% of a polypeptide according to SEQ ID NO: 16. These fibroblasts expressed higher levels of several extracellular matrix genes than cells incubated in media alone. As shown in FIG. 2A, fibroblasts treated with a polypeptide of SEQ ID NO: 16 (FIG. 2A; "C") upregulated the collagen type I gene (COL1A) relative to untreated cells (FIG. 2A; "A") or fibroblasts treated with retinol (FIG. 2A; "B"). This response was similar to fibroblasts treated with Vitamin C (FIG. 2A; "D"). As shown in FIG. 2B, fibroblasts treated with a polypeptide of SEQ ID NO: 16 (FIG. 2B; "B") upregulated the elastin gene (ELN) relative to untreated cells (FIG. 2B; "A"), and various marine collagens (FIG. 2B; "C", "D", "E", and "F"). As shown in FIG. 2C, fibroblasts treated with a polypeptide of SEQ ID NO: 16 (FIG. 2C; "B") upregulated the fibronectin gene (FN1) relative to untreated cells (FIG. 2C; "A"), retinol (FIG. 2C; "C"), and Vitamin C (FIG. 2C; "D").

Truncated Human Type 21 Alpha 1 Collagen Reduces Inflammation of Keratinocytes Irradiated With UVB Light.

Figure 3:
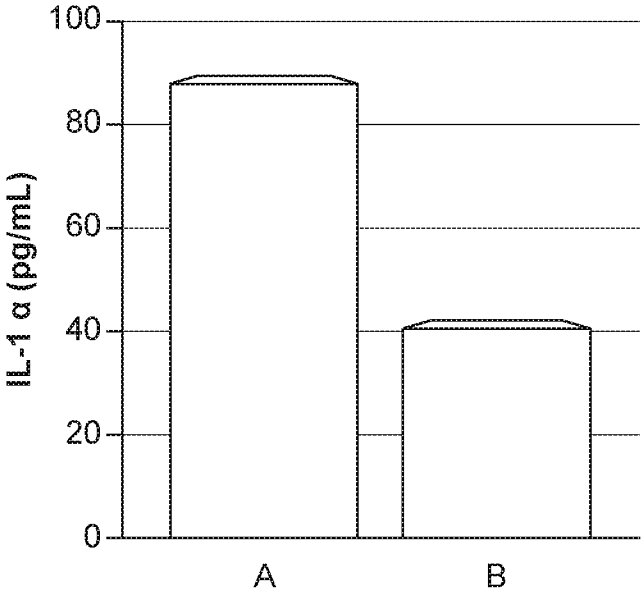
FIG. 3 illustrates expression of IL-1a in human primary keratinocytes treated with an exemplary polypeptide provided herein (comprising a truncated human collagen amino acid sequence).

Human primary keratinocytes were irradiated with 40 mJ/cm$^2$ UVB light, and then treated with 0.1% of a polypeptide of SEQ ID NO: 16 for 24 hours. Levels of the pro-inflammatory cytokines IL-1a were determined by ELISA. As shown in FIG. 3, UVB-irradiated keratinocytes treated with a polypeptide of SEQ ID NO: 16 (FIG. 3; "B") expressed lower levels of IL-1$\alpha$ compared to untreated UVB-irradiated keratinocytes (FIG. 3; "A").

Truncated Human Type 21 Alpha 1 Collagen has Anti-Oxidative Capacity.

Figure 4:
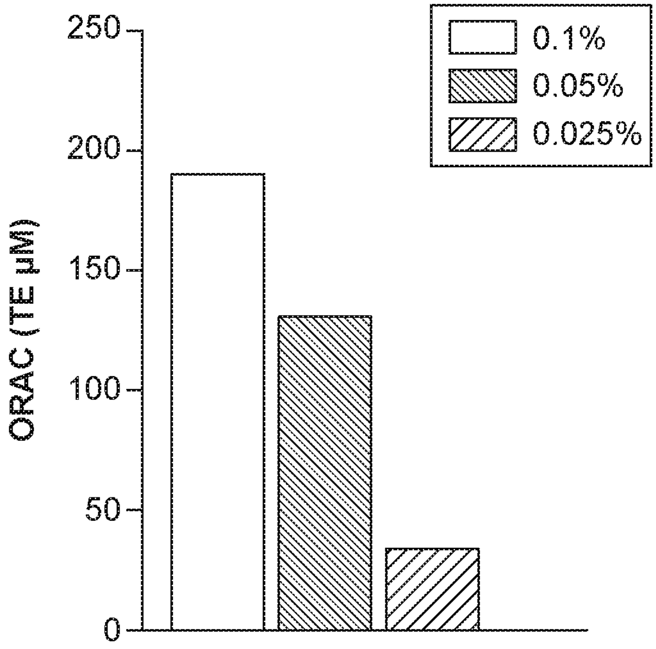
FIG. 4 illustrates antioxidant capacity of an exemplary polypeptide provided herein (comprising a truncated human collagen amino acid sequence).

The antioxidant potential of a polypeptide of SEQ ID NO: 16 was assessed using the oxygen free radical absorbance capacity (ORAC) assay. The ORAC assay is a cell-free assay that uses a fluorescent readout to measure a product's antioxidant capacity. Data is reported in Trolox (Vitamin E) equivalents. As shown in FIG. 4, a 0.1% solution of a polypeptide of SEQ ID NO: 16 had antioxidant properties equivalent to 190 μM Trolox.

Truncated Human Type 21 Alpha 1 Collagen Increases Cell Viability of Keratinocytes Irradiated With UVB Light.

Figure 5:
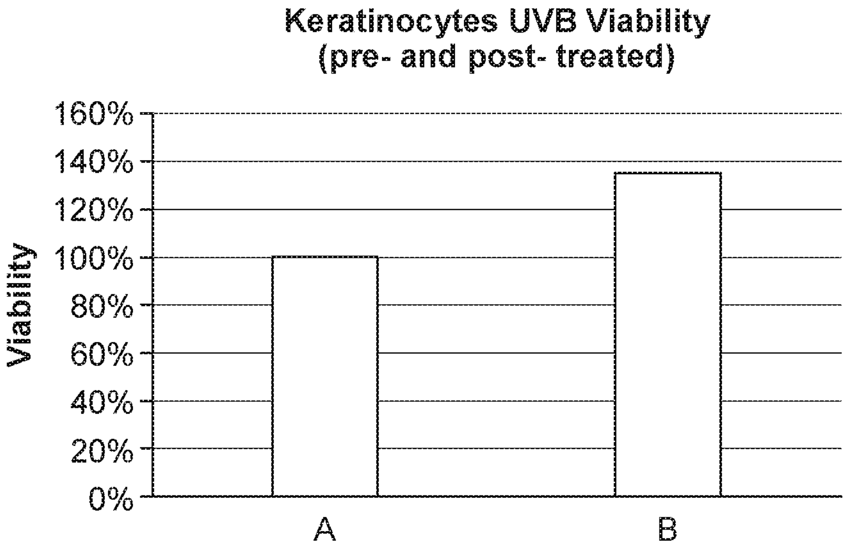
FIG. 5 illustrates viability of UVB-irradiated keratinocytes treated with an exemplary polypeptide provided herein (comprising a truncated human collagen amino acid sequence).

To further assess the effects of treatment with a polypeptide of SEQ ID NO: 16 on UVB-irradiated keratinocytes, an experiment was performed with pre- and post-irradiation treatment. Human primary keratinocytes were pre-treated with 0.1% of a polypeptide of SEQ ID NO: 16 for 24 hours, irradiated with 40 mJ/cm$^2$ UVB light, and then treated again with 0.1% of a polypeptide of SEQ ID NO: 16 for an additional 24 hours. Cell viability was evaluated using the MTT metabolic colorimetric assay. As shown in FIG. 5, UVB-irradiated keratinocytes treated with a polypeptide of SEQ ID NO: 16 (FIG. 5; "B") showed higher cell viability than UVB-irradiated keratinocytes without such treatment (FIG. 5; "A").

Example 5. Human Clinical Study of Truncated Human Type 21 Collagen

Figure 6:
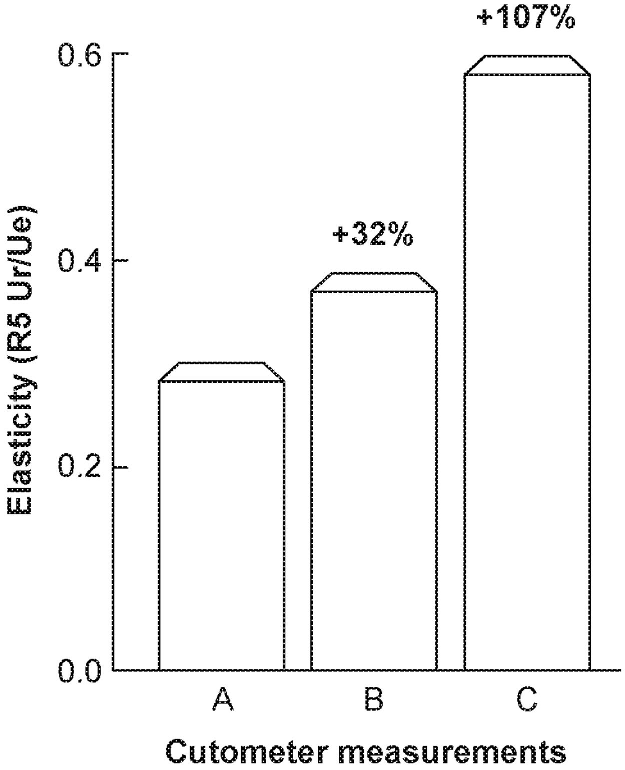
FIG. 6 illustrates skin elasticity after treatment with an exemplary polypeptide provided herein (comprising a truncated human collagen amino acid sequence).

Topical Application of Truncated Human Type 21 Alpha 1 Collagen is Associated with Facial Skin Elasticity Increase In a clinical study (n=15 subjects), subjects used a topical facial serum containing 0.1% of a polypeptide of SEQ ID NO: 16 for 8 weeks, after using a protein-free base facial serum for a 1-week washout period. Topical application of a polypeptide of SEQ ID NO: 16 was associated with increased skin elasticity, measured using a cutometer. As shown in FIG. 6, 100% of subjects showed improvement with an increase in skin elasticity at 2 weeks (FIG. 6; "B") and 4 weeks (FIG. 6; "C") as compared to baseline (FIG. 6; "A").

Figure 7:
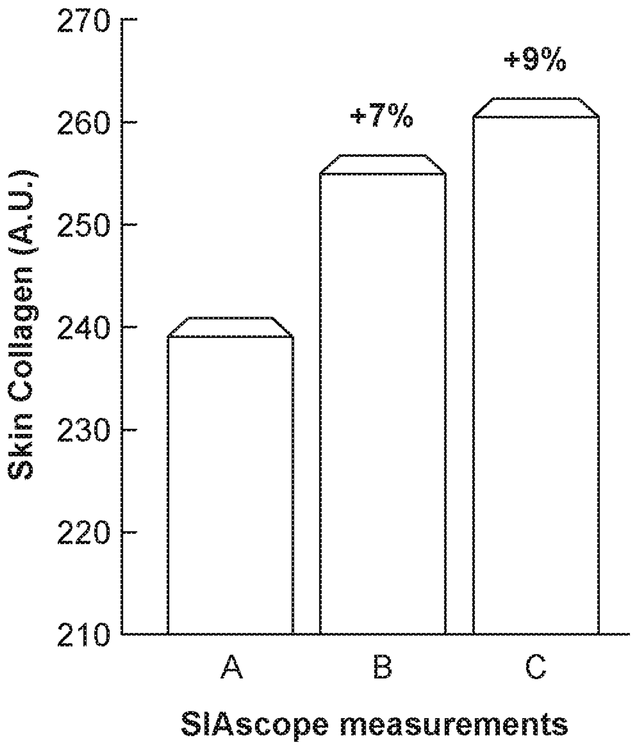
FIG. 7 illustrates skin collagen content after treatment with an exemplary polypeptide provided herein (comprising a truncated human collagen amino acid sequence).

Topical Application of Human Type 21 Alpha 1 Collagen is Associated with Facial Skin Collagen Content Increase In a clinical study (n=15 subjects), subjects used a topical facial serum containing 0.1% of a polypeptide of SEQ ID NO: 16 for 8 weeks, after using a protein-free base facial serum for a 1-week washout period. Topical application of a polypeptide of SEQ ID NO: 16 was associated with increased skin collagen content, as measured by a SIAscope. As shown in FIG. 7, skin collagen content increased at 2 weeks (FIG. 7; "B") and at 8 weeks (FIG. 7; "C") as compared to baseline (FIG. 7; "A").

Figure 8:
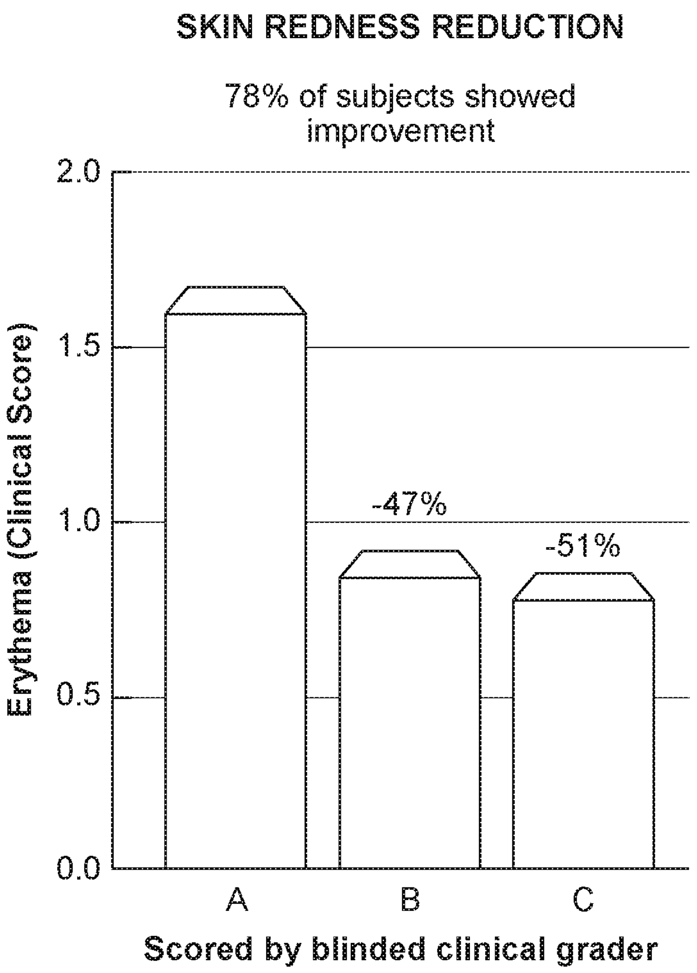
FIG. 8 illustrates quantification of skin redness after treatment with an exemplary polypeptide provided herein (comprising a truncated human collagen amino acid sequence).

Topical Application of Human Type 21 Alpha Collagen is Associated with a Reduction in Facial Skin Redness In a clinical study (n=15 subjects), subjects used a topical facial serum containing 0.1% of a polypeptide of SEQ ID NO: 16 for 8 weeks, after using a protein-free base facial serum for a 1-week washout period. As shown in FIG. 8, topical application of a polypeptide of SEQ ID NO: 16 was associated with a decrease in skin redness at 4 weeks (FIG. 8; "B") and at 8 weeks (FIG. 8; "C") as compared to baseline (FIG. 8; "A").

Figure 9:
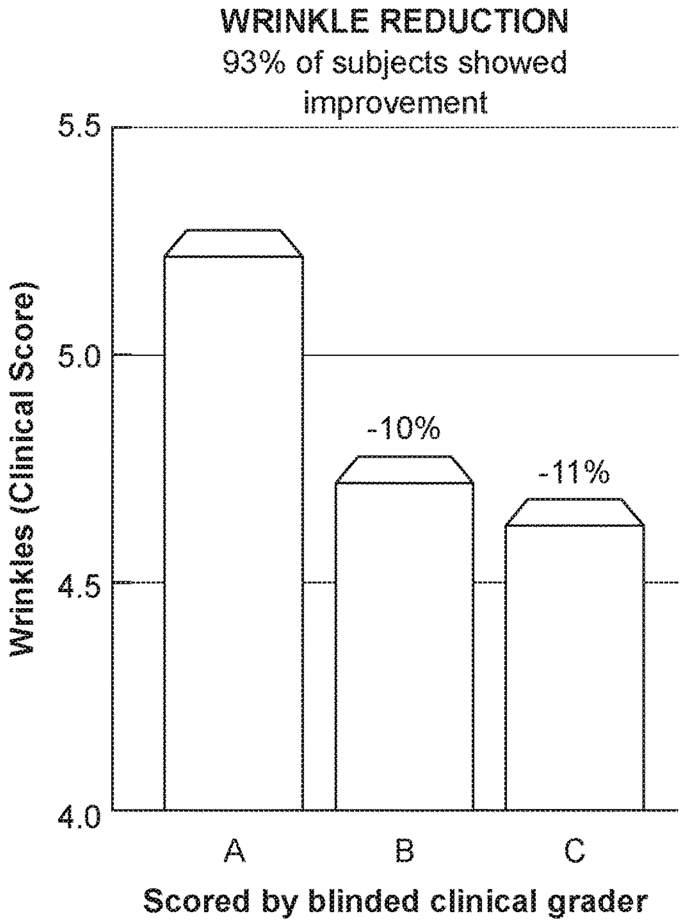
FIG. 9 illustrates quantification of skin wrinkles after treatment with an exemplary polypeptide provided herein (comprising a truncated human collagen amino acid sequence).

Topical Application of Human Type 21 Alpha 1 Collagen is Associated with a Reduction in Facial Wrinkles In a clinical study (n=15 subjects), subjects used a topical facial serum containing 0.1% of a polypeptide of SEQ ID NO: 16 for 8 weeks, after using a protein-free base facial serum for a 1-week washout period. As shown in FIG. 9, topical application of a polypeptide of SEQ ID NO: 16 was associated with a reduction in facial wrinkles at 4 weeks (FIG. 9; "B") and at 8 weeks (FIG. 9; "C") as compared to baseline (FIG. 9; "A").

Example 6. In Vitro Study of Truncated Jellyfish Collagen on Skin Cells

Figure 10:
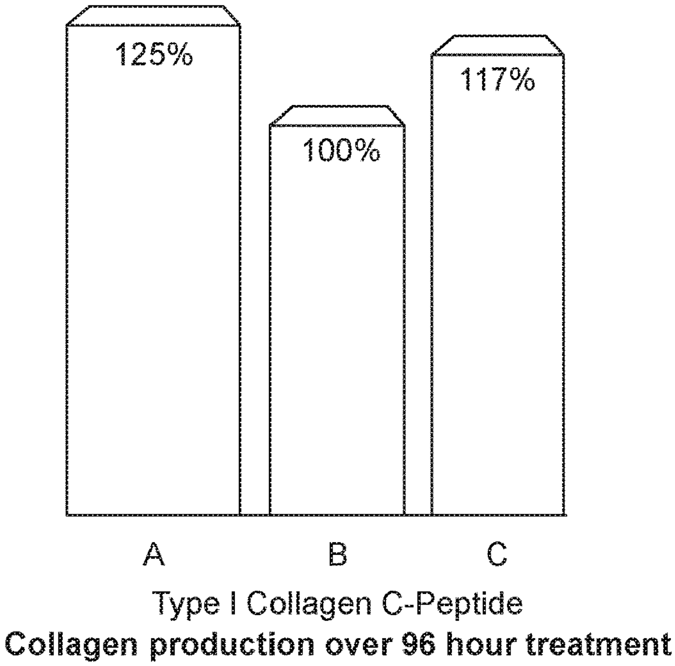
FIG. 10 illustrates collagen type 1 protein secretion by a human skin tissue model treated with an exemplary polypeptide provided herein (comprising a truncated jellyfish collagen amino acid sequence).

Truncated Jellyfish Collagen Stimulates Skin Cell Production of Collagen Type I Protein A series of in vitro experiments were conducted to assess the effects of a truncated jellyfish collagen on human skin fibroblasts and keratinocytes. An in vitro full thickness human skin tissue model (MatTek) which contains fibroblasts and keratinocytes was evaluated for collagen type I secretion after treatment with a polypeptide of SEQ ID NO: 5 for 48 hours. The tissue models were then rinsed and incubated with fresh media for another 48 hours (96 hour timepoint). The culture supernatants were analyzed by ELISA for pro-collagen type I C-peptide (a readout for total secreted collagen type I protein). As shown in FIG. 10, the tissue models treated with a polypeptide of SEQ ID NO: 5 (FIG. 10; "A") secreted higher levels of collagen type I than untreated tissue models (FIG. 10; "B") or tissue models treated with the positive control, Vitamin B3 (FIG. 10; "C").

Figure 11:
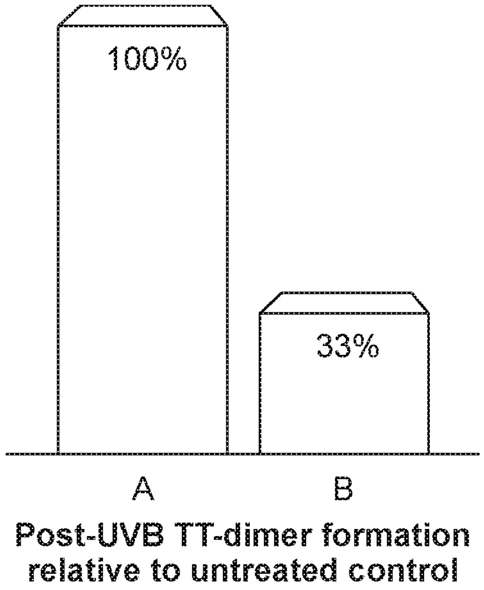
FIG. 11 illustrates UVB-induced TT dimers in keratinocytes with treatment with an exemplary polypeptide provided herein (comprising a truncated jellyfish collagen amino acid sequence).

Truncated Jellyfish Collagen Reduces DNA Damage in Keratinocytes after Exposure to UVB Light In a further study, human primary keratinocytes were irradiated with 25 mJ/cm$^2$ UVB light, then incubated overnight in media with 0.03% of a polypeptide of SEQ ID NO:

5. DNA was extracted from the cells and analyzed for levels of thymine dimers (an indicator of DNA damage) using an OxiSelect UV-Induced DNA Damage ELISA kit. As shown in FIG. 11, cells treated with a polypeptide of SEQ ID NO: 5 (FIG. 11; "B") showed a lower level of thymine dimers, and thus less DNA damage, than untreated cells (FIG. 11; "A").

Figure 12:
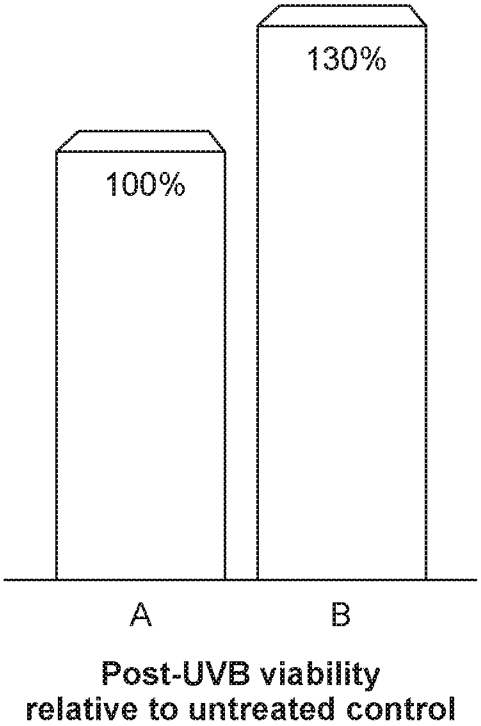
FIG. 12 illustrates keratinocyte viability after UVB irradiation with treatment with an exemplary polypeptide provided herein (comprising a truncated jellyfish collagen amino acid sequence).

Truncated Jellyfish Collagen Increases Cell Viability of Keratinocytes Irradiated with UVB Light Human primary keratinocytes were irradiated with 40 mJ/cm$^2$ UVB light, then incubated for 48 hours in media with 0.03% of a polypeptide of SEQ ID NO: 5. Cell viability was evaluated using the MTT metabolic colorimetric assay. As shown in FIG. 12, UVB-irradiated keratinocytes treated with a polypeptide of SEQ ID NO: 5 (FIG. 12; "B") showed higher cell viability than untreated UVB-irradiated keratinocytes (FIG. 12; "A").

Figure 13:
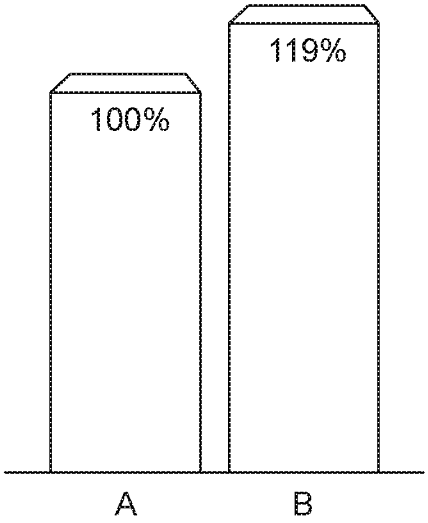
FIG. 13 illustrates cell viability when treated with urban dust and an exemplary polypeptide provided herein (comprising a truncated jellyfish collagen amino acid sequence).

Truncated Jellyfish Collagen Increases Cell Viability of Keratinocytes Exposed to Urban Dust Pollution To test for protection from urban dust, human primary keratinocytes were pre-treated with 0.03% of a polypeptide of SEQ ID NO: 5 for 24 hours, and then exposed to 2 mg/ml urban dust (NIST 1649B) for 24 hours. Cell viability was evaluated using the MTT metabolic colorimetric assay. As shown in FIG. 13, keratinocytes pre-treated with a polypeptide of SEQ ID NO: 5 (FIG. 13; "B") showed higher cell viability after urban dust exposure than untreated keratinocytes exposed to urban dust (FIG. 13; "A").

Figure 14:
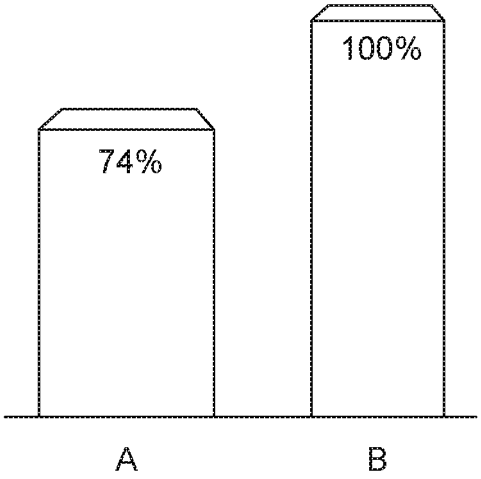
FIG. 14 illustrates relative expression of IL-1a induced by UVB after treatment with an exemplary polypeptide provided herein (comprising a truncated jellyfish collagen amino acid sequence).

Truncated Jellyfish Collagen Reduces Inflammation of Keratinocytes Irradiated with UVB Light In a further study with the in vitro full thickness human skin tissue model (MatTek), the MatTek tissue models were irradiated with 300 mJ/cm$^2$ UVB light, then treated with 0.01% of a polypeptide of SEQ ID NO: 5 for 24 hours. Levels of pro-inflammatory cytokine IL-1$\alpha$ was determined by ELISA. As seen in FIG. 14, the tissue model treated with a polypeptide of SEQ ID NO: 5 (FIG. 14; "A") showed lower levels of IL-1$\alpha$ compared to the untreated UVB-irradiated (FIG. 14; "B") control tissue model.

Truncated Jellyfish Collagen has Anti-Oxidative Capacity

Figure 15:
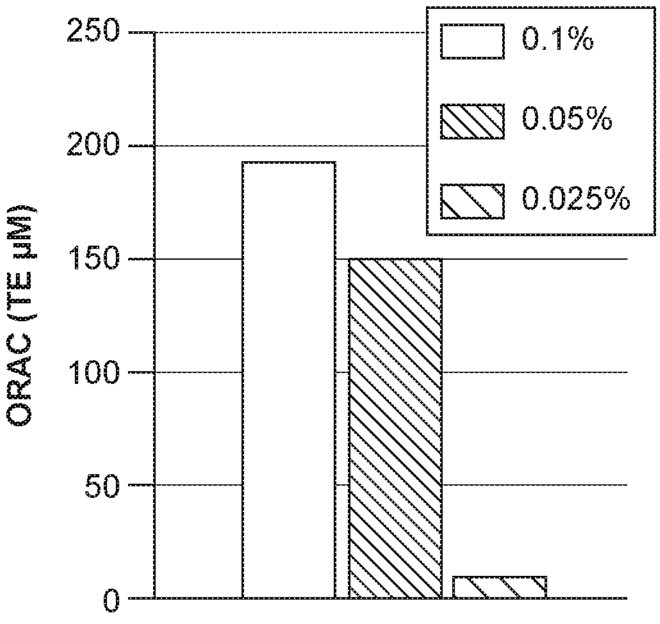
FIG. 15 illustrates antioxidant capacity of an exemplary polypeptide provided herein (comprising a truncated jellyfish collagen amino acid sequence).

A polypeptide of SEQ ID NO: 5 was also evaluated in the ORAC assay. As shown in FIG. 15, a 0.1% solution of a polypeptide of SEQ ID NO: 5 had anti-oxidative properties equivalent to 193 μM Trolox.

Example 7. Human Clinical Study of Truncated Jellyfish Collagen

Figure 16:
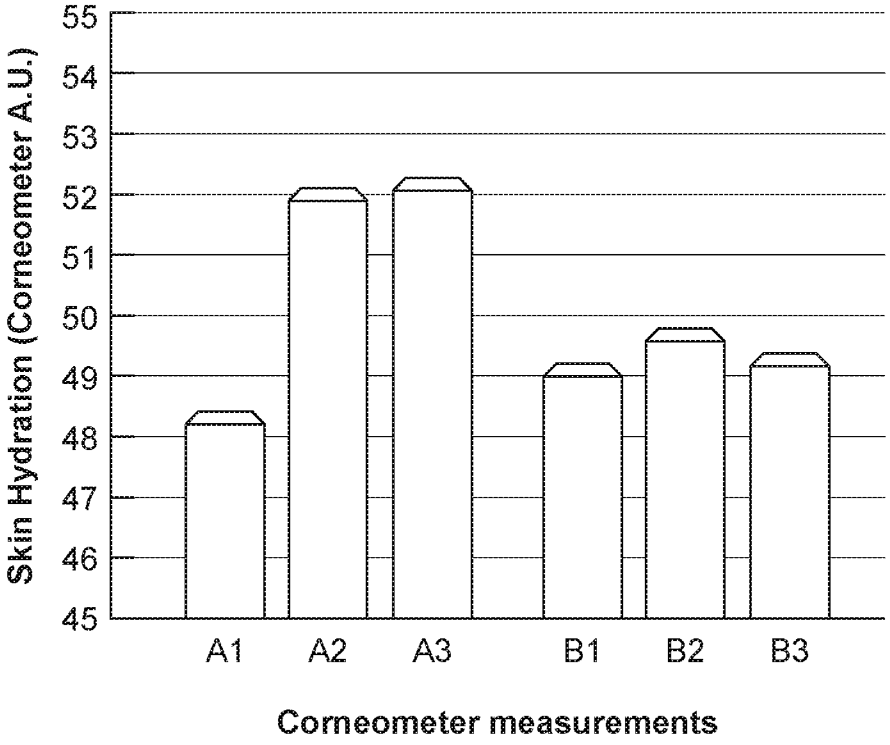
FIG. 16 illustrates skin hydration after treatment with an exemplary polypeptide provided herein (comprising a truncated jellyfish collagen amino acid sequence).

Topical Application of a Truncated Jellyfish Collagen is Associated with an Increase in Facial Skin Moisture In a clinical study (n=18 subjects), subjects used a topical facial cream containing 0.05% of a polypeptide of SEQ ID NO: 5 for 2 weeks. As shown in FIG. 16, topical application of a polypeptide of SEQ ID NO: 5 was associated with increased skin hydration at 1 week (FIG. 16; "A2") and at 2 weeks (FIG. 16; "A3") as compared to baseline (FIG. 16; "A1"). Topical application of a polypeptide of SEQ ID NO: 5 also demonstrated increased skin hydration relative to topical application of marine collagen at baseline (FIG. 16; "B1"), at 1 week (FIG. 16; "B2"), and at 2 weeks (FIG. 16; "B3").

Figure 17:
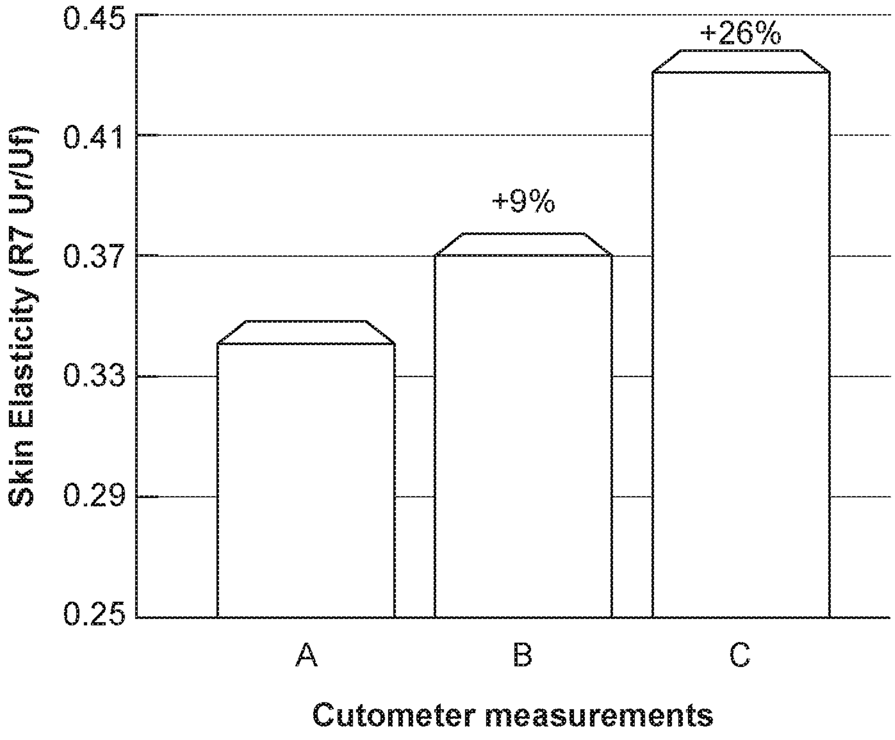
FIG. 17 illustrates skin elasticity after treatment with an exemplary polypeptide provided herein (comprising a truncated jellyfish collagen amino acid sequence).

Topical Application of Truncated Jellyfish Collagen is Associated with an Increase in Facial Skin Elasticity In a clinical study (n=18 subjects), subjects used a topical facial cream containing 0.05% of a polypeptide of SEQ ID NO: 5 for 2 weeks. As shown in FIG. 17, topical application of a polypeptide of SEQ ID NO: 5 was associated with increased skin elasticity, measured using a cutometer, at 1 week (FIG. 17; "B") and at 2 weeks (FIG. 17; "C"), as compared to baseline (FIG. 17; "A").

The disclosed embodiment herein may be embodied in other specific forms without departing from the structures, methods, or other characteristics as broadly described herein and claimed hereinafter. The described embodiments are to be considered in all respects only as illustrative, and not restrictive. All changes that come within the meaning and range of equivalency of the claims are to be embraced within their scope.

What is claimed is:

1. A non-naturally occurring polypeptide produced in a microbial host cell, the non-naturally occurring polypeptide comprising an amino acid sequence having at least about 80% sequence identity to a truncate of SEQ ID NO: 31, wherein:

i) the truncate of SEQ ID NO: 31 has a truncation at both the N-terminal end and the C-terminal end, ii) the truncate of SEQ ID NO: 31 has a total truncation of 500 amino acids to 770 amino acids, iii) the non-naturally occurring polypeptide comprises the amino acid sequence of SEQ ID NO: 16, and iv) the non-naturally occurring polypeptide lacks glycine-proline-hydroxyproline triplets and does not form a triple helix structure of natural collagen.

2. The non-naturally occurring polypeptide of claim 1, wherein the truncate of SEQ ID NO: 31 has an N-terminal truncation of 450 to 558 amino acids and a C-terminal truncation of 50 to 212 amino acids.

3. The non-naturally occurring polypeptide of claim 1, wherein the non-naturally occurring polypeptide is a fusion polypeptide further comprising a secretion tag, a histidine tag, a fluorescent protein, a protease cleavage side, one or more GEK repeats, one or more GDK repeats and/or beta-lactamase.

4. The non-naturally occurring polypeptide of claim 1, wherein the microbial host cell is a bacterial cell, a yeast cell, or a fungal cell.

5. The non-naturally occurring polypeptide of claim 1, wherein the microbial host cell is *Escherichia coli.*

6. A composition comprising about 0.001% to about 30% w/w of a non-naturally occurring polypeptide of claim 1.

7. The composition of claim 6, wherein the composition is formulated for topical application.

8. The composition of claim 7, wherein the composition is a personal care product for application to skin or hair.

9. The composition of claim 8, wherein the personal care product is selected from the group consisting of: a facial cream, a facial lotion, a facial serum, a facial mask, a facial toner, a boy cream, a body moisturizer, an eye cream, an eye treatment, a lip balm, a lipstick, a hair shampoo, a hair conditioner, a hair serum, a scalp serum, a hair mist, and a hair spray.

10. The composition of claim 7, wherein the composition is a cosmetic.

11. The composition of claim 7, further comprising a topical carrier selected from the group consisting of a liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monosterate, polysorbate, cetyl ester wax, cetearyl alcohol, 2-oxtyldodecanol, benzyl alcohol, cyclomethicone, cycopentasiloxane, and water.

12. A topical formulation comprising a non-naturally occurring polypeptide of claim 1 and one or more additional ingredients selected from the group consisting of water, oil, glycereth-8 esters, glycerin, coconut alkanes, hydroxyethyl acrylate/sodium acryloyldimethyl taurate copolymer, pentylene glycol, disodium ethylenediaminetraacetic acid (EDTA), caprylyl glycol, chlorophenesin, and phenoxyethanol.

* * * * *

SEQUENCE LISTING

```
<160> NUMBER OF SEQ ID NOS: 47

<210> SEQ ID NO 1
<211> LENGTH: 825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atgaaaaaga tttggctggc gctggctggt ttagttttag cgtttagcgc atcggcggcg     60

cagtatgaag atcaccatca ccaccaccac catcaccact ctggctcgag cctggtgccg    120

cgcggcagcc atatgggtcc gcagggtgtt gttggtgcag atggtaaaga cggtaccccg    180

ggtgaaaaag gagaacaggg acgtacaggt gcagcaggta aacagggcag cccgggtgcc    240

gatggtgccc gtggcccgct gggtagcatt ggtcagcagg gtgcaagagg cgaaccgggc    300

gatccgggta gtccgggcct gcgtggtgat acgggtctgg ccggtgttaa aggcgttgca    360

ggtccttcag gtcgtccagg tcaaccgggt gcaaatggtc tgccgggtgt taatggtcgt    420

ggcggtctgg aacgtggtct ggcaggaccg ccgggtcctg atggtcgccg cggtgaaacg    480
```

ggttcaccgg gtattgccgg tgccctgggt aaaccaggtc tggaaggtcc gaaaggttat 540
cctggtctgc gcggtcgtga tggtaccaat ggcaaacgtg gcgaacaggg cgaaaccggt 600
ccagatggtg ttcgtggtat tccgggtaac gatggtcaga gcggtaaacc gggcattgat 660
ggtattgatg gcaccaatgg tcagcctggc gaagcaggtt atcagggtgg tcgcggtacc 720
cgtggtcagc tgggtgaaac aggtgatgtt ggtcagaatg gtgatcgcgg cgcaccgggt 780
ccggatggta gcaaaggtag cgccggtcgt ccgggtttac gttaa 825

<210> SEQ ID NO 2
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Met Lys Lys Ile Trp Leu Ala Leu Ala Gly Leu Val Leu Ala Phe Ser
1 5 10 15

Ala Ser Ala Ala Gln Tyr Glu Asp His His His His His His His His
20 25 30

His Ser Gly Ser Ser Leu Val Pro Arg Gly Ser His Met Gly Pro Gln
35 40 45

Gly Val Val Gly Ala Asp Gly Lys Asp Gly Thr Pro Gly Glu Lys Gly
50 55 60

Glu Gln Gly Arg Thr Gly Ala Ala Gly Lys Gln Gly Ser Pro Gly Ala
65 70 75 80

Asp Gly Ala Arg Gly Pro Leu Gly Ser Ile Gly Gln Gln Gly Ala Arg
85 90 95

Gly Glu Pro Gly Asp Pro Gly Ser Pro Gly Leu Arg Gly Asp Thr Gly
100 105 110

Leu Ala Gly Val Lys Gly Val Ala Gly Pro Ser Gly Arg Pro Gly Gln
115 120 125

Pro Gly Ala Asn Gly Leu Pro Gly Val Asn Gly Arg Gly Gly Leu Glu
130 135 140

Arg Gly Leu Ala Gly Pro Pro Gly Pro Asp Gly Arg Arg Gly Glu Thr
145 150 155 160

Gly Ser Pro Gly Ile Ala Gly Ala Leu Gly Lys Pro Gly Leu Glu Gly
165 170 175

Pro Lys Gly Tyr Pro Gly Leu Arg Gly Arg Asp Gly Thr Asn Gly Lys
180 185 190

Arg Gly Glu Gln Gly Glu Thr Gly Pro Asp Gly Val Arg Gly Ile Pro
195 200 205

Gly Asn Asp Gly Gln Ser Gly Lys Pro Gly Ile Asp Gly Ile Asp Gly
210 215 220

Thr Asn Gly Gln Pro Gly Glu Ala Gly Tyr Gln Gly Gly Arg Gly Thr
225 230 235 240

Arg Gly Gln Leu Gly Glu Thr Gly Asp Val Gly Gln Asn Gly Asp Arg
245 250 255

Gly Ala Pro Gly Pro Asp Gly Ser Lys Gly Ser Ala Gly Arg Pro Gly
260 265 270

Leu Arg

<210> SEQ ID NO 3
<211> LENGTH: 689

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

gtccgcaggg tgttgttggt gcagatggta aagacggtac cccgggtgaa aaaggagaac     60

agggacgtac aggtgcagca ggtaaacagg gcagcccggg tgccgatggt gcccgtggcc    120

cgctgggtag cattggtcag cagggtgcaa gaggcgaacc gggcgatccg ggtagtccgg    180

gcctgcgtgg tgatacgggt ctggccggtg ttaaaggcgt tgcaggtcct tcaggtcgtc    240

caggtcaacc gggtgcaaat ggtctgccgg gtgttaatgg tcgtggcggt ctggaacgtg    300

gtctggcagg accgccgggt cctgatggtc gccgcggtga aacgggttca ccgggtattg    360

ccggtgccct gggtaaacca ggtctggaag gtccgaaagg ttatcctggt ctgcgcggtc    420

gtgatggtac caatggcaaa cgtggcgaac agggcgaaac cggtccagat ggtgttcgtg    480

gtattccggg taacgatggt cagagcggta aaccgggcat tgatggtatt gatggcacca    540

atggtcagcc tggcgaagca ggttatcagg gtggtcgcgg tacccgtggt cagctgggtg    600

aaacaggtga tgttggtcag aatggtgatc gcggcgcacc gggtccggat ggtagcaaag    660

gtagcgccgg tcgtccgggt ttacgttaa                                      689


<210> SEQ ID NO 4
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Pro Gln Gly Val Val Gly Ala Asp Gly Lys Asp Gly Thr Pro Gly
1               5                   10                  15

Glu Lys Gly Glu Gln Gly Arg Thr Gly Ala Ala Gly Lys Gln Gly Ser
            20                  25                  30

Pro Gly Ala Asp Gly Ala Arg Gly Pro Leu Gly Ser Ile Gly Gln Gln
        35                  40                  45

Gly Ala Arg Gly Glu Pro Gly Asp Pro Gly Ser Pro Gly Leu Arg Gly
    50                  55                  60

Asp Thr Gly Leu Ala Gly Val Lys Gly Val Ala Gly Pro Ser Gly Arg
65                  70                  75                  80

Pro Gly Gln Pro Gly Ala Asn Gly Leu Pro Gly Val Asn Gly Arg Gly
                85                  90                  95

Gly Leu Glu Arg Gly Leu Ala Gly Pro Pro Gly Pro Asp Gly Arg Arg
            100                 105                 110

Gly Glu Thr Gly Ser Pro Gly Ile Ala Gly Ala Leu Gly Lys Pro Gly
        115                 120                 125

Leu Glu Gly Pro Lys Gly Tyr Pro Gly Leu Arg Gly Arg Asp Gly Thr
    130                 135                 140

Asn Gly Lys Arg Gly Glu Gln Gly Glu Thr Gly Pro Asp Gly Val Arg
145                 150                 155                 160

Gly Ile Pro Gly Asn Asp Gly Gln Ser Gly Lys Pro Gly Ile Asp Gly
                165                 170                 175

Ile Asp Gly Thr Asn Gly Gln Pro Gly Glu Ala Gly Tyr Gln Gly Gly
            180                 185                 190
```

Arg Gly Thr Arg Gly Gln Leu Gly Glu Thr Gly Asp Val Gly Gln Asn
195 200 205

Gly Asp Arg Gly Ala Pro Gly Pro Asp Gly Ser Lys Gly Ser Ala Gly
210 215 220

Arg Pro Gly Leu Arg
225

<210> SEQ ID NO 5
<211> LENGTH: 189
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Gly Pro Gln Gly Val Val Gly Ala Asp Gly Lys Asp Gly Thr Pro Gly
1 5 10 15

Asn Ala Gly Gln Lys Gly Pro Ser Gly Glu Pro Gly Ser Pro Gly Lys
20 25 30

Ala Gly Ser Ala Gly Glu Gln Gly Pro Pro Gly Lys Asp Gly Ser Asn
35 40 45

Gly Glu Pro Gly Ser Pro Gly Lys Glu Gly Glu Arg Gly Leu Ala Gly
50 55 60

Pro Pro Gly Pro Asp Gly Arg Arg Gly Glu Thr Gly Ser Pro Gly Ile
65 70 75 80

Ala Gly Ala Leu Gly Lys Pro Gly Leu Glu Gly Pro Lys Gly Tyr Pro
85 90 95

Gly Leu Arg Gly Arg Asp Gly Thr Asn Gly Lys Arg Gly Glu Gln Gly
100 105 110

Glu Thr Gly Pro Asp Gly Val Arg Gly Ile Pro Gly Asn Asp Gly Gln
115 120 125

Ser Gly Lys Pro Gly Ile Asp Gly Ile Asp Gly Thr Asn Gly Gln Pro
130 135 140

Gly Glu Ala Gly Tyr Gln Gly Gly Arg Gly Thr Arg Gly Gln Leu Gly
145 150 155 160

Glu Thr Gly Asp Val Gly Gln Asn Gly Asp Arg Gly Ala Pro Gly Pro
165 170 175

Asp Gly Ser Lys Gly Ser Ala Gly Arg Pro Gly Leu Arg
180 185

<210> SEQ ID NO 6
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
atgaaaaaga tttggctggc gctggctggt ttagttttag cgtttagcgc atcggcggcg 60
cagtatgaag atggtccgca gggtgttgtt ggtgcagatg gtaaagacgg taccccgggt 120
aatgcaggtc agaaaggtcc gtcaggtgaa cctggcagcc ctggtaaagc aggtagtgcc 180
ggtgagcagg gtccgccggg caaagatggt agtaatggtg agccgggtag ccctggcaaa 240
gaaggtgaac gtggtctggc aggaccgccg ggtcctgatg gtcgccgcgg tgaaacgggt 300
tcaccgggta ttgccggtgc cctgggtaaa ccaggtctgg aaggtccgaa aggttatcct 360
ggtctgcgcg gtcgtgatgg taccaatggc aaacgtggcg aacagggcga aaccggtcca 420
gatggtgttc gtggtattcc gggtaacgat ggtcagagcg gtaaaccggg cattgatggt 480
attgatggca ccaatggtca gcctggcgaa gcaggttatc agggtggtcg cggtacccgt 540
ggtcagctgg gtgaaacagg tgatgttggt cagaatggtg atcgcggcgc accgggtccg 600
gatggtagca aaggtagcgc cggtcgtccg ggtttacgtt aa 642

<210> SEQ ID NO 7
<211> LENGTH: 213
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

Met Lys Lys Ile Trp Leu Ala Leu Ala Gly Leu Val Leu Ala Phe Ser
1 5 10 15

Ala Ser Ala Ala Gln Tyr Glu Asp Gly Pro Gln Gly Val Val Gly Ala
20 25 30

Asp Gly Lys Asp Gly Thr Pro Gly Asn Ala Gly Gln Lys Gly Pro Ser
35 40 45

Gly Glu Pro Gly Ser Pro Gly Lys Ala Gly Ser Ala Gly Glu Gln Gly
50 55 60

Pro Pro Gly Lys Asp Gly Ser Asn Gly Glu Pro Gly Ser Pro Gly Lys
65 70 75 80

Glu Gly Glu Arg Gly Leu Ala Gly Pro Pro Gly Pro Asp Gly Arg Arg
85 90 95

Gly Glu Thr Gly Ser Pro Gly Ile Ala Gly Ala Leu Gly Lys Pro Gly
100 105 110

Leu Glu Gly Pro Lys Gly Tyr Pro Gly Leu Arg Gly Arg Asp Gly Thr
115 120 125

Asn Gly Lys Arg Gly Glu Gln Gly Glu Thr Gly Pro Asp Gly Val Arg
130 135 140

Gly Ile Pro Gly Asn Asp Gly Gln Ser Gly Lys Pro Gly Ile Asp Gly
145 150 155 160

Ile Asp Gly Thr Asn Gly Gln Pro Gly Glu Ala Gly Tyr Gln Gly Gly
165 170 175

Arg Gly Thr Arg Gly Gln Leu Gly Glu Thr Gly Asp Val Gly Gln Asn
180 185 190

Gly Asp Arg Gly Ala Pro Gly Pro Asp Gly Ser Lys Gly Ser Ala Gly
195 200 205

Arg Pro Gly Leu Arg
210

<210> SEQ ID NO 8
<211> LENGTH: 570
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
ggtccgcagg gtgttgttgg tgcagatggt aaagacggta ccccgggtaa tgcaggtcag 60
aaaggtccgt caggtgaacc tggcagccct ggtaaagcag gtagtgccgg tgagcagggt 120
ccgccgggca aagatggtag taatggtgag ccgggtagcc ctggcaaaga aggtgaacgt 180
ggtctggcag gaccgccggg tcctgatggt cgccgcggtg aaacgggttc accgggtatt 240
gccggtgccc tgggtaaacc aggtctggaa ggtccgaaag gttatcctgg tctgcgcggt 300
cgtgatggta ccaatggcaa acgtggcgaa cagggcgaaa ccggtccaga tggtgttcgt 360
ggtattccgg gtaacgatgg tcagagcggt aaaccgggca ttgatggtat tgatggcacc 420
aatggtcagc ctggcgaagc aggttatcag ggtggtcgcg gtacccgtgg tcagctgggt 480
gaaacaggtg atgttggtca gaatggtgat cgcggcgcac cgggtccgga tggtagcaaa 540
ggtagcgccg gtcgtccggg tttacgttaa 570

<210> SEQ ID NO 9
<211> LENGTH: 2232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
atgaaaaaga tttggctggc gctggctggt ttagttttag cgtttagcgc atcggcggcg 60
cagtatgaag atcaccatca ccaccaccac catcaccact ctggctcgag cctggtgccg 120
cgcggcagcc atatgtctgg ctcgagcagt aaaggtgaag aactgttcac cggtgttgtt 180
ccgatcctgg ttgaactgga tggtgatgtt aacggccaca aattctctgt tcgtggtgaa 240
ggtgaaggtg atgcaaccaa cggtaaactg accctgaaat tcatctgcac taccggtaaa 300
ctgccggttc catggccgac tctggtgact accctgacct atggtgttca gtgtttttct 360
cgttacccgg atcacatgaa gcagcatgat ttcttcaaat ctgcaatgcc ggaaggttat 420
gtacaggagc gcaccatttc tttcaaagac gatggcacct acaaaacccg tgcagaggtt 480
aaatttgaag gtgatactct ggtgaaccgt attgaactga aaggcattga tttcaaagag 540
gacggcaaca tcctgggcca caaactggaa tataacttca actcccataa cgtttacatc 600
accgcagaca aacagaagaa cggtatcaaa gctaacttca aaattcgcca taacgttgaa 660
gacggtagcg tacagctggc ggaccactac cagcagaaca ctccgatcgg tgatggtccg 720
gttctgctgc cggataacca ctacctgtcc acccagtcta aactgtccaa agacccgaac 780
gaaaagcgcg accacatggt gctgctggag ttcgttactg cagcaggtat cacgcacggc 840
atggatgaac tctacaaatc tggcgcgccg ggcggtccgc agggtgttgt tggtgcagat 900
ggtaaagacg gtaccccggg taatgcaggt cagaaaggtc cgtcaggtga acctggcagc 960
cctggtaaag caggtagtgc cggtgagcag ggtccgccgg gcaaagatgg tagtaatggt 1020
gagccgggta gccctggcaa agaaggtgaa cgtggtctgg caggaccgcc gggtcctgat 1080
ggtcgccgcg gtgaaacggg ttcaccgggt attgccggtg ccctgggtaa accaggtctg 1140
gaaggtccga aaggttatcc tggtctgcgc ggtcgtgatg gtaccaatgg caaacgtggc 1200
gaacagggcg aaaccggtcc agatggtgtt cgtggtattc cgggtaacga tggtcagagc 1260
ggtaaaccgg gcattgatgg tattgatggc accaatggtc agcctggcga agcaggttat 1320
cagggtggtc gcggtacccg tggtcagctg ggtgaaacag gtgatgttgg tcagaatggt 1380
gatcgcggcg caccgggtcc ggatggtagc aaaggtagcg ccggtcgtcc gggtttacgt 1440
cacccagaaa cgctggtgaa agtaaaagat gctgaagatc agttgggtgc acgagtgggt 1500
tacatcgaac tggatctcaa cagcggtaag atccttgaga gttttcgccc cgaagaacgt 1560
tttccaatga tgagcacttt taaagttctg ctatgtggcg cggtattatc ccgtattgac 1620
gccgggcaag agcaactcgg tcgccgcata cactattctc agaatgactt ggttgagtac 1680
tcaccagtca cagaaaagca tcttacggat ggcatgacag taagagaatt atgcagtgct 1740
gccataacca tgagtgataa cactgcggcc aacttacttc tgacaacgat cggaggaccg 1800
aaggagctaa ccgctttttt gcacaacatg ggggatcatg taactcgcct tgatcgttgg 1860
gaaccggagc tgaatgaagc cataccaaac gacgagcgtg acaccacgat gcctgtagca 1920
atggcaacaa cgttgcgcaa actattaact ggcgaactac ttactctagc ttcccggcaa 1980
caattaatag actggatgga ggcggataaa gttgcaggac cacttctgcg ctcggccctt 2040
ccggctggct ggtttattgc tgataaatct ggagccggtg agcgtgggtc tcgcggtatc 2100
attgcagcac tggggccaga tggtaagccc tcccgtatcg tagttatcta cacgacgggg 2160
agtcaggcaa ctatggatga acgaaataga cagatcgctg agataggtgc ctcactgatt 2220
aagcattggt aa 2232

<210> SEQ ID NO 10
<211> LENGTH: 743
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

Met Lys Lys Ile Trp Leu Ala Leu Ala Gly Leu Val Leu Ala Phe Ser
1 5 10 15

Ala Ser Ala Ala Gln Tyr Glu Asp His His His His His His His His
20 25 30

His Ser Gly Ser Ser Leu Val Pro Arg Gly Ser His Met Ser Gly Ser
35 40 45

Ser Ser Lys Gly Glu Glu Leu Phe Thr Gly Val Val Pro Ile Leu Val
50 55 60

Glu Leu Asp Gly Asp Val Asn Gly His Lys Phe Ser Val Arg Gly Glu
65 70 75 80

Gly Glu Gly Asp Ala Thr Asn Gly Lys Leu Thr Leu Lys Phe Ile Cys
85 90 95

Thr Thr Gly Lys Leu Pro Val Pro Trp Pro Thr Leu Val Thr Thr Leu
100 105 110

Thr Tyr Gly Val Gln Cys Phe Ser Arg Tyr Pro Asp His Met Lys Gln
115 120 125

His Asp Phe Phe Lys Ser Ala Met Pro Glu Gly Tyr Val Gln Glu Arg
130 135 140

Thr Ile Ser Phe Lys Asp Asp Gly Thr Tyr Lys Thr Arg Ala Glu Val
145 150 155 160

Lys Phe Glu Gly Asp Thr Leu Val Asn Arg Ile Glu Leu Lys Gly Ile
165 170 175

Asp Phe Lys Glu Asp Gly Asn Ile Leu Gly His Lys Leu Glu Tyr Asn
180 185 190

Phe Asn Ser His Asn Val Tyr Ile Thr Ala Asp Lys Gln Lys Asn Gly
195 200 205

Ile Lys Ala Asn Phe Lys Ile Arg His Asn Val Glu Asp Gly Ser Val
210 215 220

Gln Leu Ala Asp His Tyr Gln Gln Asn Thr Pro Ile Gly Asp Gly Pro
225 230 235 240

-continued

```
Val Leu Leu Pro Asp Asn His Tyr Leu Ser Thr Gln Ser Lys Leu Ser
                245                 250                 255

Lys Asp Pro Asn Glu Lys Arg Asp His Met Val Leu Leu Glu Phe Val
            260                 265                 270

Thr Ala Ala Gly Ile Thr His Gly Met Asp Glu Leu Tyr Lys Ser Gly
        275                 280                 285

Ala Pro Gly Gly Pro Gln Gly Val Val Gly Ala Asp Gly Lys Asp Gly
    290                 295                 300

Thr Pro Gly Asn Ala Gly Gln Lys Gly Pro Ser Gly Glu Pro Gly Ser
305                 310                 315                 320

Pro Gly Lys Ala Gly Ser Ala Gly Glu Gln Gly Pro Pro Gly Lys Asp
                325                 330                 335

Gly Ser Asn Gly Glu Pro Gly Ser Pro Gly Lys Glu Gly Glu Arg Gly
            340                 345                 350

Leu Ala Gly Pro Pro Gly Pro Asp Gly Arg Arg Gly Glu Thr Gly Ser
        355                 360                 365

Pro Gly Ile Ala Gly Ala Leu Gly Lys Pro Gly Leu Glu Gly Pro Lys
    370                 375                 380

Gly Tyr Pro Gly Leu Arg Gly Arg Asp Gly Thr Asn Gly Lys Arg Gly
385                 390                 395                 400

Glu Gln Gly Glu Thr Gly Pro Asp Gly Val Arg Gly Ile Pro Gly Asn
                405                 410                 415

Asp Gly Gln Ser Gly Lys Pro Gly Ile Asp Gly Ile Asp Gly Thr Asn
            420                 425                 430

Gly Gln Pro Gly Glu Ala Gly Tyr Gln Gly Gly Arg Gly Thr Arg Gly
        435                 440                 445

Gln Leu Gly Glu Thr Gly Asp Val Gly Gln Asn Gly Asp Arg Gly Ala
    450                 455                 460

Pro Gly Pro Asp Gly Ser Lys Gly Ser Ala Gly Arg Pro Gly Leu Arg
465                 470                 475                 480

His Pro Glu Thr Leu Val Lys Val Lys Asp Ala Glu Asp Gln Leu Gly
                485                 490                 495

Ala Arg Val Gly Tyr Ile Glu Leu Asp Leu Asn Ser Gly Lys Ile Leu
            500                 505                 510

Glu Ser Phe Arg Pro Glu Glu Arg Phe Pro Met Met Ser Thr Phe Lys
        515                 520                 525

Val Leu Leu Cys Gly Ala Val Leu Ser Arg Ile Asp Ala Gly Gln Glu
    530                 535                 540

Gln Leu Gly Arg Arg Ile His Tyr Ser Gln Asn Asp Leu Val Glu Tyr
545                 550                 555                 560

Ser Pro Val Thr Glu Lys His Leu Thr Asp Gly Met Thr Val Arg Glu
                565                 570                 575

Leu Cys Ser Ala Ala Ile Thr Met Ser Asp Asn Thr Ala Ala Asn Leu
            580                 585                 590

Leu Leu Thr Thr Ile Gly Gly Pro Lys Glu Leu Thr Ala Phe Leu His
        595                 600                 605

Asn Met Gly Asp His Val Thr Arg Leu Asp Arg Trp Glu Pro Glu Leu
    610                 615                 620

Asn Glu Ala Ile Pro Asn Asp Glu Arg Asp Thr Thr Met Pro Val Ala
625                 630                 635                 640

Met Ala Thr Thr Leu Arg Lys Leu Leu Thr Gly Glu Leu Leu Thr Leu
                645                 650                 655

Ala Ser Arg Gln Gln Leu Ile Asp Trp Met Glu Ala Asp Lys Val Ala
```

```
            660                 665                 670

Gly Pro Leu Leu Arg Ser Ala Leu Pro Ala Gly Trp Phe Ile Ala Asp
        675                 680                 685

Lys Ser Gly Ala Gly Glu Arg Gly Ser Arg Gly Ile Ile Ala Ala Leu
    690                 695                 700

Gly Pro Asp Gly Lys Pro Ser Arg Ile Val Val Ile Tyr Thr Thr Gly
705                 710                 715                 720

Ser Gln Ala Thr Met Asp Glu Arg Asn Arg Gln Ile Ala Glu Ile Gly
                725                 730                 735

Ala Ser Leu Ile Lys His Trp
            740


<210> SEQ ID NO 11
<211> LENGTH: 2232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

atgaaaaaga tttggctggc gctggctggt ttagttttag cgtttagcgc atcggcggcg     60

cagtatgaag atcaccatca ccaccaccac catcaccact ctggctcgag cctggtgccg    120

cgcggcagcc atatgtctgg ctcgagcagt aaaggtgaag aactgttcac cggtgttgtt    180

ccgatcctgg ttgaactgga tggtgatgtt aacggccaca aattctctgt tcgtggtgaa    240

ggtgaaggtg atgcaaccaa cggtaaactg accctgaaat tcatctgcac taccggtaaa    300

ctgccggttc catggccgac tctggtgact accctgacct atggtgttca gtgtttttct    360

cgttacccgg atcacatgaa gcagcatgat ttcttcaaat ctgcaatgcc ggaaggttat    420

gtacaggagc gcaccatttc tttcaaagac gatggcacct acaaaacccg tgcagaggtt    480

aaatttgaag gtgatactct ggtgaaccgt attgaactga aaggcattga tttcaaagag    540

gacggcaaca tcctgggcca caaactggaa tataacttca actcccataa cgtttacatc    600

accgcagaca aacagaagaa cggtatcaaa gctaacttca aaattcgcca taacgttgaa    660

gacggtagcg tacagctggc ggaccactac cagcagaaca ctccgatcgg tgatggtccg    720

gttctgctgc cggataacca ctacctgtcc acccagtcta aactgtccaa agacccgaac    780

gaaaagcgcg accacatggt gctgctggag ttcgttactg cagcaggtat cacgcacggc    840

atggatgaac tctacaaatc tggcgcgccg ggcggtccgc agggtgttgt tggtgcagat    900

ggtaaagacg gtaccccggg taatgcaggt cagaaaggtc cgtcaggtga acctggcagc    960

cctggtaaag caggtagtgc cggtgagcag ggtccgccgg gcaaagatgg tagtaatggt   1020

gagccgggta gccctggcaa agaaggtgaa cgtggtctgg caggaccgcc gggtcctgat   1080

ggtcgccgcg gtgaaacggg ttcaccgggt attgccggtg ccctgggtaa accaggtctg   1140

gaaggtccga aaggttatcc tggtctgcgc ggtcgtgatg gtaccaatgg caaacgtggc   1200

gaacagggcg aaaccggtcc agatggtgtt cgtggtattc cgggtaacga tggtcagagc   1260

ggtaaaccgg gcattgatgg tattgatggc accaatggtc agcctggcga agcaggttat   1320

cagggtggtc gcggtacccg tggtcagctg ggtgaaacag gtgatgttgg tcagaatggt   1380

gatcgcggcg caccgggtcc ggatggtagc aaaggtagcg ccggtcgtcc gggtttacgt   1440

cacccagaaa cgctggtgaa agtaaaagat gctgaagatc agttgggtgc acgagtgggt   1500

tacatcgaac tggatctcaa cagcggtaag atccttgaga gttttcgccc cgaagaacgt   1560
```

```
tttccaatga tgagcacttt taaagttctg ctatgtggcg cggtattatc ccgtattgac   1620

gccgggcaag agcaactcgg tcgccgcata cactattctc agaatgactt ggttgagtac   1680

tcaccagtca cagaaaagca tcttacggat ggcatgacag taagagaatt atgcagtgct   1740

gccataacca tgagtgataa cactgcggcc aacttacttc tgacaacgat cggaggaccg   1800

aaggagctaa ccgctttttt gcacaacatg ggggatcatg taactcgcct tgatcgttgg   1860

gaaccggagc tgaatgaagc cataccaaac gacgagcgtg acaccacgat gcctgtagca   1920

atggcaacaa cgttgcgcaa actattaact ggcgaactac ttactctagc ttcccggcaa   1980

caattaatag actggatgga ggcggataaa gttgcaggac cacttctgcg ctcggccctt   2040

ccggctggct ggtttattgc tgataaatct ggagccggtg agcgtgggtc tcgcggtatc   2100

attgcagcac tggggccaga tggtaagccc tcccgtatcg tagttatcta cacgacgggg   2160

agtcaggcaa ctatggatga acgaaataga cagatcgctg agataggtgc ctcactgatt   2220

aagcattggt aa                                                       2232


<210> SEQ ID NO 12
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Lys Ile Trp Leu Ala Leu Ala Gly Leu Val Leu Ala Phe Ser
1               5                   10                  15

Ala Ser Ala Ala Gln Tyr Glu Asp His His His His His His His His
            20                  25                  30

His Ser Gly Ser Ser Leu Val Pro Arg Gly Ser His Met Ser Gly Ser
        35                  40                  45

Ser Ser Lys Gly Glu Glu Leu Phe Thr Gly Val Val Pro Ile Leu Val
    50                  55                  60

Glu Leu Asp Gly Asp Val Asn Gly His Lys Phe Ser Val Arg Gly Glu
65                  70                  75                  80

Gly Glu Gly Asp Ala Thr Asn Gly Lys Leu Thr Leu Lys Phe Ile Cys
                85                  90                  95

Thr Thr Gly Lys Leu Pro Val Pro Trp Pro Thr Leu Val Thr Thr Leu
            100                 105                 110

Thr Tyr Gly Val Gln Cys Phe Ser Arg Tyr Pro Asp His Met Lys Gln
        115                 120                 125

His Asp Phe Phe Lys Ser Ala Met Pro Glu Gly Tyr Val Gln Glu Arg
    130                 135                 140

Thr Ile Ser Phe Lys Asp Asp Gly Thr Tyr Lys Thr Arg Ala Glu Val
145                 150                 155                 160

Lys Phe Glu Gly Asp Thr Leu Val Asn Arg Ile Glu Leu Lys Gly Ile
                165                 170                 175

Asp Phe Lys Glu Asp Gly Asn Ile Leu Gly His Lys Leu Glu Tyr Asn
            180                 185                 190

Phe Asn Ser His Asn Val Tyr Ile Thr Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
```

-continued

```
225                 230                 235                 240

Val Leu Leu Pro Asp Asn His Tyr Leu Ser Thr Gln Ser Lys Leu Ser
                245                 250                 255

Lys Asp Pro Asn Glu Lys Arg Asp His Met Val Leu Leu Glu Phe Val
            260                 265                 270

Thr Ala Ala Gly Ile Thr His Gly Met Asp Glu Leu Tyr Lys Ser Gly
        275                 280                 285

Ala Pro Gly Gly Pro Gln Gly Val Val Gly Ala Asp Gly Lys Asp Gly
    290                 295                 300

Thr Pro Gly Asn Ala Gly Gln Lys Gly Pro Ser Gly Glu Pro Gly Ser
305                 310                 315                 320

Pro Gly Lys Ala Gly Ser Ala Gly Glu Gln Gly Pro Pro Gly Lys Asp
                325                 330                 335

Gly Ser Asn Gly Glu Pro Gly Ser Pro Gly Lys Glu Gly Glu Arg Gly
            340                 345                 350

Leu Ala Gly Pro Pro Gly Pro Asp Gly Arg Arg Gly Glu Thr Gly Ser
        355                 360                 365

Pro Gly Ile Ala Gly Ala Leu Gly Lys Pro Gly Leu Glu Gly Pro Lys
    370                 375                 380

Gly Tyr Pro Gly Leu Arg Gly Arg Asp Gly Thr Asn Gly Lys Arg Gly
385                 390                 395                 400

Glu Gln Gly Glu Thr Gly Pro Asp Gly Val Arg Gly Ile Pro Gly Asn
                405                 410                 415

Asp Gly Gln Ser Gly Lys Pro Gly Ile Asp Gly Ile Asp Gly Thr Asn
            420                 425                 430

Gly Gln Pro Gly Glu Ala Gly Tyr Gln Gly Gly Arg Gly Thr Arg Gly
        435                 440                 445

Gln Leu Gly Glu Thr Gly Asp Val Gly Gln Asn Gly Asp Arg Gly Ala
    450                 455                 460

Pro Gly Pro Asp Gly Ser Lys Gly Ser Ala Gly Arg Pro Gly Leu Arg
465                 470                 475                 480

His Pro Glu Thr Leu Val Lys Val Lys Asp Ala Glu Asp Gln Leu Gly
                485                 490                 495

Ala Arg Val Gly Tyr Ile Glu Leu Asp Leu Asn Ser Gly Lys Ile Leu
            500                 505                 510

Glu Ser Phe Arg Pro Glu Glu Arg Phe Pro Met Met Ser Thr Phe Lys
        515                 520                 525

Val Leu Leu Cys Gly Ala Val Leu Ser Arg Ile Asp Ala Gly Gln Glu
    530                 535                 540

Gln Leu Gly Arg Arg Ile His Tyr Ser Gln Asn Asp Leu Val Glu Tyr
545                 550                 555                 560

Ser Pro Val Thr Glu Lys His Leu Thr Asp Gly Met Thr Val Arg Glu
                565                 570                 575

Leu Cys Ser Ala Ala Ile Thr Met Ser Asp Asn Thr Ala Ala Asn Leu
            580                 585                 590

Leu Leu Thr Thr Ile Gly Gly Pro Lys Glu Leu Thr Ala Phe Leu His
        595                 600                 605

Asn Met Gly Asp His Val Thr Arg Leu Asp Arg Trp Glu Pro Glu Leu
    610                 615                 620

Asn Glu Ala Ile Pro Asn Asp Glu Arg Asp Thr Thr Met Pro Val Ala
625                 630                 635                 640

Met Ala Thr Thr Leu Arg Lys Leu Leu Thr Gly Glu Leu Leu Thr Leu
                645                 650                 655
```

```
Ala Ser Arg Gln Gln Leu Ile Asp Trp Met Glu Ala Asp Lys Val Ala
            660                 665                 670

Gly Pro Leu Leu Arg Ser Ala Leu Pro Ala Gly Trp Phe Ile Ala Asp
        675                 680                 685

Lys Ser Gly Ala Gly Glu Arg Gly Ser Arg Gly Ile Ile Ala Ala Leu
    690                 695                 700

Gly Pro Asp Gly Lys Pro Ser Arg Ile Val Val Ile Tyr Thr Thr Gly
705                 710                 715                 720

Ser Gln Ala Thr Met Asp Glu Arg Asn Arg Gln Ile Ala Glu Ile Gly
                725                 730                 735

Ala Ser Leu Ile Lys His Trp
            740


<210> SEQ ID NO 13
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

atgaaaaaga tttggctggc gctggctggt ttagttttag cgtttagcgc atcggcggcg      60

cagtatgaag atgcaggttt tccgggtctg cctggtccgg caggcgaacc gggtcgtcat     120

ggtaaagatg gtctgatggg tagtccgggt tttaaaggtg aagcaggttc accgggtgca     180

cctggtcagg atggcacccg tggtgaaccg ggtattccgg gatttccggg taatcgtggc     240

ctgatgggtc agaaaggtga aattggtccg cctggtcagc agggtaaaaa aggcgcaccg     300

ggtatgccag gactgatggg ttcaaatggc agtccgggtc agccaggcac accgggttca     360

aaaggtagca aaggcgaacc tggtattcag ggtatgcctg gtgcaagcgg tctgaaaggc     420

gagccaggtg ccaccggttc tccgggtgaa ccaggttata tgggtctgcc aggtatccaa     480

ggcaaaaaag gtgataaagg taatcagggc gaaaaaggca ttcagggcca gaaaggcgaa     540

aatggccgtc agggtattcc aggccagcag ggcatccagg gtcatcatgg tgcaaaaggt     600

gaacgtggtg aaaagggcga accaggtgtt cgttta                               636


<210> SEQ ID NO 14
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Lys Lys Ile Trp Leu Ala Leu Ala Gly Leu Val Leu Ala Phe Ser
1               5                   10                  15

Ala Ser Ala Ala Gln Tyr Glu Asp Ala Gly Phe Pro Gly Leu Pro Gly
            20                  25                  30

Pro Ala Gly Glu Pro Gly Arg His Gly Lys Asp Gly Leu Met Gly Ser
        35                  40                  45

Pro Gly Phe Lys Gly Glu Ala Gly Ser Pro Gly Ala Pro Gly Gln Asp
    50                  55                  60

Gly Thr Arg Gly Glu Pro Gly Ile Pro Gly Phe Pro Gly Asn Arg Gly
65                  70                  75                  80

Leu Met Gly Gln Lys Gly Glu Ile Gly Pro Pro Gly Gln Gln Gly Lys
```

85 90 95

Lys Gly Ala Pro Gly Met Pro Gly Leu Met Gly Ser Asn Gly Ser Pro
100 105 110

Gly Gln Pro Gly Thr Pro Gly Ser Lys Gly Ser Lys Gly Glu Pro Gly
115 120 125

Ile Gln Gly Met Pro Gly Ala Ser Gly Leu Lys Gly Glu Pro Gly Ala
130 135 140

Thr Gly Ser Pro Gly Glu Pro Gly Tyr Met Gly Leu Pro Gly Ile Gln
145 150 155 160

Gly Lys Lys Gly Asp Lys Gly Asn Gln Gly Glu Lys Gly Ile Gln Gly
165 170 175

Gln Lys Gly Glu Asn Gly Arg Gln Gly Ile Pro Gly Gln Gln Gly Ile
180 185 190

Gln Gly His His Gly Ala Lys Gly Glu Arg Gly Glu Lys Gly Glu Pro
195 200 205

Gly Val Arg
210

<210> SEQ ID NO 15
<211> LENGTH: 565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
tgcaggtttt ccgggtctgc ctggtccggc aggcgaaccg ggtcgtcatg gtaaagatgg 60
tctgatgggt agtccgggtt ttaaaggtga agcaggttca ccgggtgcac ctggtcagga 120
tggcacccgt ggtgaaccgg gtattccggg atttccgggt aatcgtggcc tgatgggtca 180
gaaaggtgaa attggtccgc ctggtcagca gggtaaaaaa ggcgcaccgg gtatgccagg 240
actgatgggt tcaaatggca gtccgggtca gccaggcaca ccgggttcaa aaggtagcaa 300
aggcgaacct ggtattcagg gtatgcctgg tgcaagcggt ctgaaaggcg agccaggtgc 360
caccggttct ccgggtgaac caggttatat gggtctgcca ggtatccaag gcaaaaaagg 420
tgataaaggt aatcagggcg aaaaaggcat tcagggccag aaaggcgaaa atggccgtca 480
gggtattcca ggccagcagg gcatccaggg tcatcatggt gcaaaaggtg aacgtggtga 540
aaagggcgaa ccaggtgttc gttaa 565

<210> SEQ ID NO 16
<211> LENGTH: 187
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Ala Gly Phe Pro Gly Leu Pro Gly Pro Ala Gly Glu Pro Gly Arg His
1 5 10 15

Gly Lys Asp Gly Leu Met Gly Ser Pro Gly Phe Lys Gly Glu Ala Gly
20 25 30

Ser Pro Gly Ala Pro Gly Gln Asp Gly Thr Arg Gly Glu Pro Gly Ile
35 40 45

Pro Gly Phe Pro Gly Asn Arg Gly Leu Met Gly Gln Lys Gly Glu Ile
50 55 60

Gly Pro Pro Gly Gln Gln Gly Lys Lys Gly Ala Pro Gly Met Pro Gly
65 70 75 80

Leu Met Gly Ser Asn Gly Ser Pro Gly Gln Pro Gly Thr Pro Gly Ser
85 90 95

Lys Gly Ser Lys Gly Glu Pro Gly Ile Gln Gly Met Pro Gly Ala Ser
100 105 110

Gly Leu Lys Gly Glu Pro Gly Ala Thr Gly Ser Pro Gly Glu Pro Gly
115 120 125

Tyr Met Gly Leu Pro Gly Ile Gln Gly Lys Lys Gly Asp Lys Gly Asn
130 135 140

Gln Gly Glu Lys Gly Ile Gln Gly Gln Lys Gly Glu Asn Gly Arg Gln
145 150 155 160

Gly Ile Pro Gly Gln Gln Gly Ile Gln Gly His His Gly Ala Lys Gly
165 170 175

Glu Arg Gly Glu Lys Gly Glu Pro Gly Val Arg
180 185

<210> SEQ ID NO 17
<211> LENGTH: 639
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
atgaaaaaga tttggctggc gctggctggt ttagttttag cgtttagcgc atcggcggcg 60
cagtatgaag atatgggtcc gcctggtagc cgtggtgcaa gtggtccggc aggcgttcgt 120
ggtccgaatg gtgatgcagg tcgtccgggt gaaccgggtc tgatgggtcc tcgtggtctg 180
cctggttcac cgggtaatat tggtcctgca ggtaaagaag gtccggttgg tctgccaggt 240
attgatggcc gtccgggtcc gattggtcca gccggtgcac gtggtgaacc tggcaatatt 300
ggttttccgg gtcctaaagg tccgaccggt gatccgggta aaaatggtga taaaggtcat 360
gcaggtctgg caggcgcacg cggtgcacct ggtccggatg gtaataatgg tgcacagggt 420
ccaccgggtc cgcagggtgt tcaaggtggt aaaggcgaac agggtcctgc cggtcctccg 480
ggttttcagg gactgcctgg tccgagcggt cctgcgggtg aagttggtaa acctggtgaa 540
cgcggtctgc atggtgaatt tggcctgcct gggcctgcag gtccgcgtgg cgaacgtggt 600
ccgccaggtg aaagcggtgc agcaggtccg acaggttaa 639

<210> SEQ ID NO 18
<211> LENGTH: 212
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Met Lys Lys Ile Trp Leu Ala Leu Ala Gly Leu Val Leu Ala Phe Ser
1 5 10 15

Ala Ser Ala Ala Gln Tyr Glu Asp Met Gly Pro Pro Gly Ser Arg Gly
20 25 30

Ala Ser Gly Pro Ala Gly Val Arg Gly Pro Asn Gly Asp Ala Gly Arg
35 40 45

Pro Gly Glu Pro Gly Leu Met Gly Pro Arg Gly Leu Pro Gly Ser Pro

```
    50                  55                  60

Gly Asn Ile Gly Pro Ala Gly Lys Glu Gly Pro Val Gly Leu Pro Gly
65                  70                  75                  80

Ile Asp Gly Arg Pro Gly Pro Ile Gly Pro Ala Gly Ala Arg Gly Glu
                85                  90                  95

Pro Gly Asn Ile Gly Phe Pro Gly Pro Lys Gly Pro Thr Gly Asp Pro
            100                 105                 110

Gly Lys Asn Gly Asp Lys Gly His Ala Gly Leu Ala Gly Ala Arg Gly
        115                 120                 125

Ala Pro Gly Pro Asp Gly Asn Asn Gly Ala Gln Gly Pro Pro Gly Pro
    130                 135                 140

Gln Gly Val Gln Gly Gly Lys Gly Glu Gln Gly Pro Ala Gly Pro Pro
145                 150                 155                 160

Gly Phe Gln Gly Leu Pro Gly Pro Ser Gly Pro Ala Gly Glu Val Gly
                165                 170                 175

Lys Pro Gly Glu Arg Gly Leu His Gly Glu Phe Gly Leu Pro Gly Pro
            180                 185                 190

Ala Gly Pro Arg Gly Glu Arg Gly Pro Pro Gly Glu Ser Gly Ala Ala
        195                 200                 205

Gly Pro Thr Gly
    210


<210> SEQ ID NO 19
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

atgggtccgc ctggtagccg tggtgcaagt ggtccggcag gcgttcgtgg tccgaatggt     60

gatgcaggtc gtccgggtga accgggtctg atgggtcctc gtggtctgcc tggttcaccg    120

ggtaatattg gtcctgcagg taaagaaggt ccggttggtc tgccaggtat tgatggccgt    180

ccgggtccga ttggtccagc cggtgcacgt ggtgaacctg gcaatattgg ttttccgggt    240

cctaaaggtc cgaccggtga tccgggtaaa aatggtgata aaggtcatgc aggtctggca    300

ggcgcacgcg gtgcacctgg tccggatggt aataatggtg cacagggtcc accgggtccg    360

cagggtgttc aaggtggtaa aggcgaacag ggtcctgccg gtcctccggg ttttcaggga    420

ctgcctggtc cgagcggtcc tgcgggtgaa gttggtaaac ctggtgaacg cggtctgcat    480

ggtgaatttg gcctgcctgg gcctgcaggt ccgcgtggcg aacgtggtcc gccaggtgaa    540

agcggtgcag caggtccgac aggttaa                                        567


<210> SEQ ID NO 20
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Pro Pro Gly Ser Arg Gly Ala Ser Gly Pro Ala Gly Val Arg
1               5                   10                  15

Gly Pro Asn Gly Asp Ala Gly Arg Pro Gly Glu Pro Gly Leu Met Gly
            20                  25                  30
```

Pro Arg Gly Leu Pro Gly Ser Pro Gly Asn Ile Gly Pro Ala Gly Lys
35 40 45

Glu Gly Pro Val Gly Leu Pro Gly Ile Asp Gly Arg Pro Gly Pro Ile
50 55 60

Gly Pro Ala Gly Ala Arg Gly Glu Pro Gly Asn Ile Gly Phe Pro Gly
65 70 75 80

Pro Lys Gly Pro Thr Gly Asp Pro Gly Lys Asn Gly Asp Lys Gly His
85 90 95

Ala Gly Leu Ala Gly Ala Arg Gly Ala Pro Gly Pro Asp Gly Asn Asn
100 105 110

Gly Ala Gln Gly Pro Pro Gly Pro Gln Gly Val Gln Gly Gly Lys Gly
115 120 125

Glu Gln Gly Pro Ala Gly Pro Pro Gly Phe Gln Gly Leu Pro Gly Pro
130 135 140

Ser Gly Pro Ala Gly Glu Val Gly Lys Pro Gly Glu Arg Gly Leu His
145 150 155 160

Gly Glu Phe Gly Leu Pro Gly Pro Ala Gly Pro Arg Gly Glu Arg Gly
165 170 175

Pro Pro Gly Glu Ser Gly Ala Ala Gly Pro Thr Gly
180 185

<210> SEQ ID NO 21
<211> LENGTH: 612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
atgaaaaaga tttggctggc gctggctggt ttagttttag cgtttagcgc atcggcggcg 60
cagtatgaag atggttttca gggtcctgcc ggtgaaccgg gtgaacctgg tcagacaggt 120
ccggcaggcg cacgtggtcc tgcaggtcct cctggtaaag ccggtgaaga tggtcatccg 180
ggtaaaccgg gtcgtcctgg tgaacgtggt gttgttggtc cgcagggtgc ccgtggtttt 240
ccgggtactc cgggtctgcc aggttttaaa ggtattcgtg gtcataatgg tctggatggt 300
ctgaaaggtc agcctggtgc accgggtgtt aaaggtgaac caggtgctcc gggtgaaaat 360
ggcacaccgg gtcagaccgg tgcgcgtggt ctgcctggcg aacgcggtcg tgttggtgca 420
cctggtccag ccggtgcacg cggtagtgat ggtagcgttg gtccggttgg tccagcgggt 480
ccgattggta gcgcaggtcc accgggtttt ccaggcgcac cgggtccgaa aggtgaaatt 540
ggtgcagttg gtaatgcagg ccctgccggt ccagcaggac cgcgtggtga agttggcctg 600
cctggtctgt aa 612

<210> SEQ ID NO 22
<211> LENGTH: 203
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Met Lys Lys Ile Trp Leu Ala Leu Ala Gly Leu Val Leu Ala Phe Ser
1 5 10 15

Ala Ser Ala Ala Gln Tyr Glu Asp Gly Phe Gln Gly Pro Ala Gly Glu

```
            20                  25                  30

Pro Gly Glu Pro Gly Gln Thr Gly Pro Ala Gly Ala Arg Gly Pro Ala
        35                  40                  45

Gly Pro Pro Gly Lys Ala Gly Glu Asp Gly His Pro Gly Lys Pro Gly
    50                  55                  60

Arg Pro Gly Glu Arg Gly Val Val Gly Pro Gln Gly Ala Arg Gly Phe
65                  70                  75                  80

Pro Gly Thr Pro Gly Leu Pro Gly Phe Lys Gly Ile Arg Gly His Asn
                85                  90                  95

Gly Leu Asp Gly Leu Lys Gly Gln Pro Gly Ala Pro Gly Val Lys Gly
            100                 105                 110

Glu Pro Gly Ala Pro Gly Glu Asn Gly Thr Pro Gly Gln Thr Gly Ala
        115                 120                 125

Arg Gly Leu Pro Gly Glu Arg Gly Arg Val Gly Ala Pro Gly Pro Ala
    130                 135                 140

Gly Ala Arg Gly Ser Asp Gly Ser Val Gly Pro Val Gly Pro Ala Gly
145                 150                 155                 160

Pro Ile Gly Ser Ala Gly Pro Pro Gly Phe Pro Gly Ala Pro Gly Pro
                165                 170                 175

Lys Gly Glu Ile Gly Ala Val Gly Asn Ala Gly Pro Ala Gly Pro Ala
            180                 185                 190

Gly Pro Arg Gly Glu Val Gly Leu Pro Gly Leu
        195                 200
```

<210> SEQ ID NO 23
<211> LENGTH: 540
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
ggttttcagg gtcctgccgg tgaaccgggt gaacctggtc agacaggtcc ggcaggcgca     60

cgtggtcctg caggtcctcc tggtaaagcc ggtgaagatg gtcatccggg taaaccgggt    120

cgtcctggtg aacgtggtgt tgttggtccg cagggtgccc gtggttttcc gggtactccg    180

ggtctgccag gttttaaagg tattcgtggt cataatggtc tggatggtct gaaaggtcag    240

cctggtgcac cgggtgttaa aggtgaacca ggtgctccgg gtgaaaatgg cacaccgggt    300

cagaccggtg cgcgtggtct gcctggcgaa cgcggtcgtg ttggtgcacc tggtccagcc    360

ggtgcacgcg gtagtgatgg tagcgttggt ccggttggtc cagcgggtcc gattggtagc    420

gcaggtccac cgggttttcc aggcgcaccg ggtccgaaag gtgaaattgg tgcagttggt    480

aatgcaggcc ctgccggtcc agcaggaccg cgtggtgaag ttggcctgcc tggtctgtaa    540
```

<210> SEQ ID NO 24
<211> LENGTH: 179
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Gly Phe Gln Gly Pro Ala Gly Glu Pro Gly Glu Pro Gly Gln Thr Gly
1               5                   10                  15

Pro Ala Gly Ala Arg Gly Pro Ala Gly Pro Pro Gly Lys Ala Gly Glu
```

```
            20                  25                  30

Asp Gly His Pro Gly Lys Pro Gly Arg Pro Gly Glu Arg Gly Val Val
        35                  40                  45

Gly Pro Gln Gly Ala Arg Gly Phe Pro Gly Thr Pro Gly Leu Pro Gly
    50                  55                  60

Phe Lys Gly Ile Arg Gly His Asn Gly Leu Asp Gly Leu Lys Gly Gln
65                  70                  75                  80

Pro Gly Ala Pro Gly Val Lys Gly Glu Pro Gly Ala Pro Gly Glu Asn
                85                  90                  95

Gly Thr Pro Gly Gln Thr Gly Ala Arg Gly Leu Pro Gly Glu Arg Gly
            100                 105                 110

Arg Val Gly Ala Pro Gly Pro Ala Gly Ala Arg Gly Ser Asp Gly Ser
        115                 120                 125

Val Gly Pro Val Gly Pro Ala Gly Pro Ile Gly Ser Ala Gly Pro Pro
    130                 135                 140

Gly Phe Pro Gly Ala Pro Gly Pro Lys Gly Glu Ile Gly Ala Val Gly
145                 150                 155                 160

Asn Ala Gly Pro Ala Gly Pro Ala Gly Pro Arg Gly Glu Val Gly Leu
                165                 170                 175

Pro Gly Leu


<210> SEQ ID NO 25
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Lys Lys Ile Trp Leu Ala Leu Ala Gly Leu Val Leu Ala Phe Ser
1               5                   10                  15

Ala Ser Ala Gly Asp Gln Gly Pro Val Gly Arg Thr Gly Glu Val Gly
            20                  25                  30

Ala Val Gly Pro Pro Gly Phe Ala Gly Glu Lys Gly Pro Ser Gly Glu
        35                  40                  45

Ala Gly Thr Ala Gly Pro Pro Gly Thr Pro Gly Pro Gln Gly Leu Leu
    50                  55                  60

Gly Ala Pro Gly Ile Leu Gly Leu Pro Gly Ser Arg Gly Glu Arg Gly
65                  70                  75                  80

Leu Pro Gly Val Ala Gly Ala Val Gly Glu Pro Gly Pro Leu Gly Ile
                85                  90                  95

Ala Gly Pro Pro Gly Ala Arg Gly Pro Pro Gly Ala Val Gly Ser Pro
            100                 105                 110

Gly Val Asn Gly Ala Pro Gly Glu Ala Gly Arg Asp Gly Asn Pro Gly
        115                 120                 125

Asn Asp Gly Pro Pro Gly Arg Asp Gly Gln Pro Gly His Lys Gly Glu
    130                 135                 140

Arg Gly Tyr Pro Gly Asn Ile Gly Pro Val Gly Ala Ala Gly Ala Pro
145                 150                 155                 160

Gly Pro His Gly Pro Val Gly Pro Ala Gly Lys His Gly Asn Arg Gly
                165                 170                 175

Glu Thr Gly Pro Ser Gly Pro Val Gly Pro Ala Gly Ala Val Gly Pro
            180                 185                 190

Arg Gly Pro Ser Gly Pro Gln Gly Ile Arg Gly Asp Lys Gly Glu Pro
```

```
        195                 200                 205

Gly Glu Lys Gly Pro Arg Gly Leu Pro Gly Leu Gly Asp Tyr Lys Asp
    210                 215                 220

Asp Asp Asp Lys
225


<210> SEQ ID NO 26
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

atgaaaaaga tttggctggc gctggctggt ttagttttag cgtttagcgc atcggcgggt      60

gatcagggtc cggttggtcg taccggtgaa gttggtgcag tcgggccgcc gggttttgcg     120

ggtgaaaaag gcccgtcagg tgaagcaggc accgctggcc ctcctggcac gcctggccca     180

cagggtttac tgggcgcacc tggaattctg ggactgccgg gcagccgtgg agaacgcggt     240

ttaccaggtg ttgccggtgc cgttggtgaa cctggtccac tgggcattgc agggccgcct     300

ggcgcacggg gaccgcctgg tgctgttggt agtccgggtg tgaatggtgc tccgggtgaa     360

gccggtcgtg acggtaatcc gggaaatgac ggcccgccag gccgcgatgg tcagccgggt     420

cataaaggtg agcgtggtta cccaggtaat attggtccag tcggtgccgc cggtgcgccg     480

ggtcctcatg gccctgtcgg tccagccggt aaacatggta atcgcggtga gacaggtccg     540

tcaggaccag tgggccctgc tggcgcagtc ggtccgcgcg ggccgagtgg ccctcagggt     600

attcgtggcg ataaagggga accgggcgaa aaagggccgc ggggtctgcc aggcctgggt     660

gactacaaag acgacgacga caaataa                                         687


<210> SEQ ID NO 27
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Lys Lys Ile Trp Leu Ala Leu Ala Gly Leu Val Leu Ala Phe Ser
1               5                   10                  15

Ala Ser Ala Lys Gly His Asn Gly Leu Gln Gly Leu Pro Gly Ile Ala
            20                  25                  30

Gly His His Gly Asp Gln Gly Ala Pro Gly Ser Val Gly Pro Ala Gly
        35                  40                  45

Pro Arg Gly Pro Ala Gly Pro Ser Gly Pro Ala Gly Lys Asp Gly Arg
    50                  55                  60

Thr Gly His Pro Gly Thr Val Gly Pro Ala Gly Ile Arg Gly Pro Gln
65                  70                  75                  80

Gly His Gln Gly Pro Ala Gly Pro Pro Gly Pro Pro Gly Pro Pro Gly
                85                  90                  95

Pro Pro Gly Val Ser Gly Gly Gly Tyr Asp Phe Gly Tyr Asp Gly Asp
            100                 105                 110

Phe Tyr Arg Ala Asp Gln Pro Arg Ser Ala Pro Ser Leu Arg Pro Lys
        115                 120                 125

Asp Tyr Glu Val Asp Ala Thr Leu Lys Ser Leu Asn Asn Gln Ile Glu
```

```
    130                 135                 140

Thr Leu Leu Thr Pro Glu Gly Ser Arg Lys Asn Pro Ala Arg Thr Cys
145                 150                 155                 160

Arg Asp Leu Arg Leu Ser His Pro Glu Trp Ser Ser Gly Tyr Tyr Trp
                165                 170                 175

Ile Asp Pro Asn Gln Gly Cys Thr Met Asp Ala Ile Lys Val Tyr Cys
            180                 185                 190

Asp Phe Ser Thr Gly Glu Thr Cys Ile Arg Ala Gln Pro Glu Asn Ile
        195                 200                 205

Pro Ala Lys Asn Trp Tyr Arg Ser Ser Lys Asp Gly Asp Tyr Lys Asp
    210                 215                 220

Asp Asp Asp Lys
225


<210> SEQ ID NO 28
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

atgaaaaaga tttggctggc gctggctggt ttagttttag cgtttagcgc atcggcgaaa      60

ggtcacaatg gactgcaagg cctgccaggt attgcaggtc atcatggtga tcaaggtgcc     120

ccgggaagcg ttggtccggc ggggccgaga ggccctgcgg gaccttcagg tccggcaggc     180

aaagatggtc ggacaggcca tccgggcacc gttggccctg caggaattcg tggaccgcag     240

ggtcatcagg gacctgctgg tccgccaggt cccccgggcc ctccgggacc accgggtgtt     300

agtggtggtg gttatgattt tggctatgat ggtgattttt atcgtgcaga tcagccgcgt     360

agcgcaccga gcctgcgtcc taaagattat gaagttgatg caaccctgaa aagcctgaat     420

aatcagattg aaacactgct gacaccggaa ggtagccgta aaaatccggc ccgtacctgt     480

cgtgatctgc gtctgagcca cccggaatgg agcagcggtt attattggat tgatccgaat     540

caaggttgta ccatggatgc aattaaagtt tattgtgatt ttagcacagg tgaaacatgt     600

atccgtgcac agccggaaaa tattccggcc aaaaattggt atcgtagtag caaagatggt     660

gactacaaag acgacgacga caaataa                                         687


<210> SEQ ID NO 29
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Lys Lys Ile Trp Leu Ala Leu Ala Gly Leu Val Leu Ala Phe Ser
1               5                   10                  15

Ala Ser Ala Tyr Glu Val Asp Ala Thr Leu Lys Ser Leu Asn Asn Gln
            20                  25                  30

Ile Glu Thr Leu Leu Thr Pro Glu Gly Ser Arg Lys Asn Pro Ala Arg
        35                  40                  45

Thr Cys Arg Asp Leu Arg Leu Ser His Pro Glu Trp Ser Ser Gly Tyr
    50                  55                  60

Tyr Trp Ile Asp Pro Asn Gln Gly Cys Thr Met Asp Ala Ile Lys Val
```

```
65                  70                  75                  80

Tyr Cys Asp Phe Ser Thr Gly Glu Thr Cys Ile Arg Ala Gln Pro Glu
                85                  90                  95

Asn Ile Pro Ala Lys Asn Trp Tyr Arg Ser Ser Lys Asp Lys Lys His
            100                 105                 110

Val Trp Leu Gly Glu Thr Ile Asn Ala Gly Ser Gln Phe Glu Tyr Asn
        115                 120                 125

Val Glu Gly Val Thr Ser Lys Glu Met Ala Thr Gln Leu Ala Phe Met
    130                 135                 140

Arg Leu Leu Ala Asn Tyr Ala Ser Gln Asn Ile Thr Tyr His Cys Lys
145                 150                 155                 160

Asn Ser Ile Ala Tyr Met Asp Glu Glu Thr Gly Asn Leu Lys Lys Ala
                165                 170                 175

Val Ile Leu Gln Gly Ser Asn Asp Val Glu Leu Val Ala Glu Gly Asn
            180                 185                 190

Ser Arg Phe Thr Tyr Thr Val Leu Val Asp Gly Cys Ser Lys Lys Thr
        195                 200                 205

Asn Glu Trp Gly Lys Thr Ile Ile Glu Tyr Lys Thr Asn Lys Pro Ser
    210                 215                 220

Arg Leu Pro Phe Leu Asp Ile Ala Pro Leu Asp Ile Gly Gly Ala Asp
225                 230                 235                 240

Gln Glu Phe Phe Val Asp Ile Gly Pro Val Cys Phe Lys Gly Asp Tyr
                245                 250                 255

Lys Asp Asp Asp Asp Lys
            260
```

<210> SEQ ID NO 30
<211> LENGTH: 788
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
tgaaaaagat ttggctggcg ctggctggtt tagttttagc gtttagcgca tcggcgtatg     60

aagttgatgc aaccctgaaa agcctgaata atcagattga aacactgctg acaccggaag    120

gtagccgtaa aaatccggcc cgtacctgtc gtgatctgcg tctgagccac ccggaatgga    180

gcagcggtta ttattggatt gatccgaatc aaggttgtac catggatgca attaaagttt    240

attgtgattt tagcacaggt gaaacatgta tccgtgcaca gccggaaaat attccggcca    300

aaaattggta tcgtagtagc aaagataaaa aacatgtgtg gctgggtgaa accattaatg    360

caggtagcca gtttgaatac aatgttgaag gtgttaccag caaagaaatg gcaacacagc    420

tggcatttat gcgtctgctg gcaaattatg caagccagaa tattacatat cattgtaaaa    480

atagcattgc atatatggat gaagaaaccg gtaatctgaa aaaagcagtt attctgcagg    540

gtagcaatga tgttgaactg gttgccgaag gtaatagccg ttttacatat accgttctgg    600

ttgatggttg tagcaaaaaa accaatgaat ggggtaaaac catcattgaa tataaaacca    660

acaaaccgag ccgtctgccg tttctggata tcgctccgct ggatattggt ggtgccgatc    720

aggaattttt tgtcgatatc ggtcctgtgt gttttaaagg tgactacaaa gacgacgacg    780

acaaataa                                                              788
```

<210> SEQ ID NO 31

<211> LENGTH: 957
<212> TYPE: PRT
<213> ORGANISM: Homo sapiens

<400> SEQUENCE: 31

```
Met Ala His Tyr Ile Thr Phe Leu Cys Met Val Leu Val Leu Leu Leu
1               5                   10                  15

Gln Asn Ser Val Leu Ala Glu Asp Gly Glu Val Arg Ser Ser Cys Arg
            20                  25                  30

Thr Ala Pro Thr Asp Leu Val Phe Ile Leu Asp Gly Ser Tyr Ser Val
        35                  40                  45

Gly Pro Glu Asn Phe Glu Ile Val Lys Lys Trp Leu Val Asn Ile Thr
    50                  55                  60

Lys Asn Phe Asp Ile Gly Pro Lys Phe Ile Gln Val Gly Val Val Gln
65                  70                  75                  80

Tyr Ser Asp Tyr Pro Val Leu Glu Ile Pro Leu Gly Ser Tyr Asp Ser
                85                  90                  95

Gly Glu His Leu Thr Ala Ala Val Glu Ser Ile Leu Tyr Leu Gly Gly
            100                 105                 110

Asn Thr Lys Thr Gly Lys Ala Ile Gln Phe Ala Leu Asp Tyr Leu Phe
        115                 120                 125

Ala Lys Ser Ser Arg Phe Leu Thr Lys Ile Ala Val Val Leu Thr Asp
    130                 135                 140

Gly Lys Ser Gln Asp Asp Val Lys Asp Ala Ala Gln Ala Ala Arg Asp
145                 150                 155                 160

Ser Lys Ile Thr Leu Phe Ala Ile Gly Val Gly Ser Glu Thr Glu Asp
                165                 170                 175

Ala Glu Leu Arg Ala Ile Ala Asn Lys Pro Ser Ser Thr Tyr Val Phe
            180                 185                 190

Tyr Val Glu Asp Tyr Ile Ala Ile Ser Lys Ile Arg Glu Val Met Lys
        195                 200                 205

Gln Lys Leu Cys Glu Glu Ser Val Cys Pro Thr Arg Ile Pro Val Ala
    210                 215                 220

Ala Arg Asp Glu Arg Gly Phe Asp Ile Leu Leu Gly Leu Asp Val Asn
225                 230                 235                 240

Lys Lys Val Lys Lys Arg Ile Gln Leu Ser Pro Lys Lys Ile Lys Gly
                245                 250                 255

Tyr Glu Val Thr Ser Lys Val Asp Leu Ser Glu Leu Thr Ser Asn Val
            260                 265                 270

Phe Pro Glu Gly Leu Pro Pro Ser Tyr Val Phe Val Ser Thr Gln Arg
        275                 280                 285

Phe Lys Val Lys Lys Ile Trp Asp Leu Trp Arg Ile Leu Thr Ile Asp
    290                 295                 300

Gly Arg Pro Gln Ile Ala Val Thr Leu Asn Gly Val Asp Lys Ile Leu
305                 310                 315                 320

Leu Phe Thr Thr Thr Ser Val Ile Asn Gly Ser Gln Val Val Thr Phe
                325                 330                 335

Ala Asn Pro Gln Val Lys Thr Leu Phe Asp Glu Gly Trp His Gln Ile
            340                 345                 350

Arg Leu Leu Val Thr Glu Gln Asp Val Thr Leu Tyr Ile Asp Asp Gln
        355                 360                 365

Gln Ile Glu Asn Lys Pro Leu His Pro Val Leu Gly Ile Leu Ile Asn
    370                 375                 380

Gly Gln Thr Gln Ile Gly Lys Tyr Ser Gly Lys Glu Glu Thr Val Gln
```

-continued

```
385                 390                 395                 400

Phe Asp Val Gln Lys Leu Arg Ile Tyr Cys Asp Pro Glu Gln Asn Asn
                405                 410                 415

Arg Glu Thr Ala Cys Glu Ile Pro Gly Phe Asn Gly Glu Cys Leu Asn
            420                 425                 430

Gly Pro Ser Asp Val Gly Ser Thr Pro Ala Pro Cys Ile Cys Pro Pro
        435                 440                 445

Gly Lys Pro Gly Leu Gln Gly Pro Lys Gly Asp Pro Gly Leu Pro Gly
    450                 455                 460

Asn Pro Gly Tyr Pro Gly Gln Pro Gly Gln Asp Gly Lys Pro Gly Tyr
465                 470                 475                 480

Gln Gly Ile Ala Gly Thr Pro Gly Val Pro Gly Ser Pro Gly Ile Gln
                485                 490                 495

Gly Ala Arg Gly Leu Pro Gly Tyr Lys Gly Glu Pro Gly Arg Asp Gly
            500                 505                 510

Asp Lys Gly Asp Arg Gly Leu Pro Gly Phe Pro Gly Leu His Gly Met
        515                 520                 525

Pro Gly Ser Lys Gly Glu Met Gly Ala Lys Gly Asp Lys Gly Ser Pro
    530                 535                 540

Gly Phe Tyr Gly Lys Lys Gly Ala Lys Gly Glu Lys Gly Asn Ala Gly
545                 550                 555                 560

Phe Pro Gly Leu Pro Gly Pro Ala Gly Glu Pro Gly Arg His Gly Lys
                565                 570                 575

Asp Gly Leu Met Gly Ser Pro Gly Phe Lys Gly Glu Ala Gly Ser Pro
            580                 585                 590

Gly Ala Pro Gly Gln Asp Gly Thr Arg Gly Glu Pro Gly Ile Pro Gly
        595                 600                 605

Phe Pro Gly Asn Arg Gly Leu Met Gly Gln Lys Gly Glu Ile Gly Pro
    610                 615                 620

Pro Gly Gln Gln Gly Lys Lys Gly Ala Pro Gly Met Pro Gly Leu Met
625                 630                 635                 640

Gly Ser Asn Gly Ser Pro Gly Gln Pro Gly Thr Pro Gly Ser Lys Gly
                645                 650                 655

Ser Lys Gly Glu Pro Gly Ile Gln Gly Met Pro Gly Ala Ser Gly Leu
            660                 665                 670

Lys Gly Glu Pro Gly Ala Thr Gly Ser Pro Gly Glu Pro Gly Tyr Met
        675                 680                 685

Gly Leu Pro Gly Ile Gln Gly Lys Lys Gly Asp Lys Gly Asn Gln Gly
    690                 695                 700

Glu Lys Gly Ile Gln Gly Gln Lys Gly Glu Asn Gly Arg Gln Gly Ile
705                 710                 715                 720

Pro Gly Gln Gln Gly Ile Gln Gly His His Gly Ala Lys Gly Glu Arg
                725                 730                 735

Gly Glu Lys Gly Glu Pro Gly Val Arg Gly Ala Ile Gly Ser Lys Gly
            740                 745                 750

Glu Ser Gly Val Asp Gly Leu Met Gly Pro Ala Gly Pro Lys Gly Gln
        755                 760                 765

Pro Gly Asp Pro Gly Pro Gln Gly Pro Pro Gly Leu Asp Gly Lys Pro
    770                 775                 780

Gly Arg Glu Phe Ser Glu Gln Phe Ile Arg Gln Val Cys Thr Asp Val
785                 790                 795                 800

Ile Arg Ala Gln Leu Pro Val Leu Leu Gln Ser Gly Arg Ile Arg Asn
                805                 810                 815
```

```
Cys Asp His Cys Leu Ser Gln His Gly Ser Pro Gly Ile Pro Gly Pro
            820                 825                 830

Pro Gly Pro Ile Gly Pro Glu Gly Pro Arg Gly Leu Pro Gly Leu Pro
        835                 840                 845

Gly Arg Asp Gly Val Pro Gly Leu Val Gly Val Pro Gly Arg Pro Gly
    850                 855                 860

Val Arg Gly Leu Lys Gly Leu Pro Gly Arg Asn Gly Glu Lys Gly Ser
865                 870                 875                 880

Gln Gly Phe Gly Tyr Pro Gly Glu Gln Gly Pro Pro Gly Pro Pro Gly
                885                 890                 895

Pro Glu Gly Pro Pro Gly Ile Ser Lys Glu Gly Pro Pro Gly Asp Pro
            900                 905                 910

Gly Leu Pro Gly Lys Asp Gly Asp His Gly Lys Pro Gly Ile Gln Gly
        915                 920                 925

Gln Pro Gly Pro Pro Gly Ile Cys Asp Pro Ser Leu Cys Phe Ser Val
    930                 935                 940

Ile Ala Arg Arg Asp Pro Phe Arg Lys Gly Pro Asn Tyr
945                 950                 955


<210> SEQ ID NO 32
<211> LENGTH: 1366
<212> TYPE: PRT
<213> ORGANISM: Homo sapiens

<400> SEQUENCE: 32

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
        35                  40                  45

Pro Pro Gly Arg Asp Gly Glu Asp Gly Pro Thr Gly Pro Pro Gly Pro
    50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
```

```
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
            260                 265                 270

Ala Gly Pro Ala Gly Pro Ala Gly Pro Arg Gly Glu Val Gly Leu Pro
        275                 280                 285

Gly Leu Ser Gly Pro Val Gly Pro Pro Gly Asn Pro Gly Ala Asn Gly
    290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
            340                 345                 350

Ser Lys Gly Glu Ser Gly Asn Lys Gly Glu Pro Gly Ser Ala Gly Pro
        355                 360                 365

Gln Gly Pro Pro Gly Pro Ser Gly Glu Glu Gly Lys Arg Gly Pro Asn
    370                 375                 380

Gly Glu Ala Gly Ser Ala Gly Pro Pro Gly Pro Pro Gly Leu Arg Gly
385                 390                 395                 400

Ser Pro Gly Ser Arg Gly Leu Pro Gly Ala Asp Gly Arg Ala Gly Val
                405                 410                 415

Met Gly Pro Pro Gly Ser Arg Gly Ala Ser Gly Pro Ala Gly Val Arg
            420                 425                 430

Gly Pro Asn Gly Asp Ala Gly Arg Pro Gly Glu Pro Gly Leu Met Gly
        435                 440                 445

Pro Arg Gly Leu Pro Gly Ser Pro Gly Asn Ile Gly Pro Ala Gly Lys
    450                 455                 460

Glu Gly Pro Val Gly Leu Pro Gly Ile Asp Gly Arg Pro Gly Pro Ile
465                 470                 475                 480

Gly Pro Ala Gly Ala Arg Gly Glu Pro Gly Asn Ile Gly Phe Pro Gly
                485                 490                 495

Pro Lys Gly Pro Thr Gly Asp Pro Gly Lys Asn Gly Asp Lys Gly His
            500                 505                 510

Ala Gly Leu Ala Gly Ala Arg Gly Ala Pro Gly Pro Asp Gly Asn Asn
        515                 520                 525

Gly Ala Gln Gly Pro Pro Gly Pro Gln Gly Val Gln Gly Gly Lys Gly
    530                 535                 540

Glu Gln Gly Pro Pro Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
                565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
        595                 600                 605

Arg Gly Pro Ser Gly Pro Pro Gly Pro Asp Gly Asn Lys Gly Glu Pro
    610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655
```

```
Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685

Ala Thr Gly Asp Arg Gly Glu Ala Gly Ala Ala Gly Pro Ala Gly Pro
    690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765

Gly Pro Pro Gly Pro Ala Gly Ser Arg Gly Asp Gly Gly Pro Pro Gly
    770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845

Ser Gly Glu Ala Gly Thr Ala Gly Pro Pro Gly Thr Pro Gly Pro Gln
    850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
        915                 920                 925

Asn Pro Gly Asn Asp Gly Pro Pro Gly Arg Asp Gly Gln Pro Gly His
    930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly  Pro Gln Gly Ile Arg  Gly Asp Lys
        995                 1000                 1005

Gly Glu  Pro Gly Glu Lys Gly  Pro Arg Gly Leu Pro  Gly Leu Lys
    1010                 1015                 1020

Gly His  Asn Gly Leu Gln Gly  Leu Pro Gly Ile Ala  Gly His His
    1025                 1030                 1035

Gly Asp  Gln Gly Ala Pro Gly  Ser Val Gly Pro Ala  Gly Pro Arg
    1040                 1045                 1050

Gly Pro  Ala Gly Pro Ser Gly  Pro Ala Gly Lys Asp  Gly Arg Thr
    1055                 1060                 1065
```

```
Gly His  Pro Gly Thr Val Gly  Pro Ala Gly Ile Arg  Gly Pro Gln
    1070                 1075                 1080

Gly His  Gln Gly Pro Ala Gly  Pro Pro Gly Pro Pro  Gly Pro Pro
    1085                 1090                 1095

Gly Pro  Pro Gly Val Ser Gly  Gly Gly Tyr Asp Phe  Gly Tyr Asp
    1100                 1105                 1110

Gly Asp  Phe Tyr Arg Ala Asp  Gln Pro Arg Ser Ala  Pro Ser Leu
    1115                 1120                 1125

Arg Pro  Lys Asp Tyr Glu Val  Asp Ala Thr Leu Lys  Ser Leu Asn
    1130                 1135                 1140

Asn Gln  Ile Glu Thr Leu Leu  Thr Pro Glu Gly Ser  Arg Lys Asn
    1145                 1150                 1155

Pro Ala  Arg Thr Cys Arg Asp  Leu Arg Leu Ser His  Pro Glu Trp
    1160                 1165                 1170

Ser Ser  Gly Tyr Tyr Trp Ile  Asp Pro Asn Gln Gly  Cys Thr Met
    1175                 1180                 1185

Asp Ala  Ile Lys Val Tyr Cys  Asp Phe Ser Thr Gly  Glu Thr Cys
    1190                 1195                 1200

Ile Arg  Ala Gln Pro Glu Asn  Ile Pro Ala Lys Asn  Trp Tyr Arg
    1205                 1210                 1215

Ser Ser  Lys Asp Lys Lys His  Val Trp Leu Gly Glu  Thr Ile Asn
    1220                 1225                 1230

Ala Gly  Ser Gln Phe Glu Tyr  Asn Val Glu Gly Val  Thr Ser Lys
    1235                 1240                 1245

Glu Met  Ala Thr Gln Leu Ala  Phe Met Arg Leu Leu  Ala Asn Tyr
    1250                 1255                 1260

Ala Ser  Gln Asn Ile Thr Tyr  His Cys Lys Asn Ser  Ile Ala Tyr
    1265                 1270                 1275

Met Asp  Glu Glu Thr Gly Asn  Leu Lys Lys Ala Val  Ile Leu Gln
    1280                 1285                 1290

Gly Ser  Asn Asp Val Glu Leu  Val Ala Glu Gly Asn  Ser Arg Phe
    1295                 1300                 1305

Thr Tyr  Thr Val Leu Val Asp  Gly Cys Ser Lys Lys  Thr Asn Glu
    1310                 1315                 1320

Trp Gly  Lys Thr Ile Ile Glu  Tyr Lys Thr Asn Lys  Pro Ser Arg
    1325                 1330                 1335

Leu Pro  Phe Leu Asp Ile Ala  Pro Leu Asp Ile Gly  Gly Ala Asp
    1340                 1345                 1350

Gln Glu  Phe Phe Val Asp Ile  Gly Pro Val Cys Phe  Lys
    1355                 1360                 1365


<210> SEQ ID NO 33
<211> LENGTH: 429
<212> TYPE: PRT
<213> ORGANISM: Podocoryna carnea

<400> SEQUENCE: 33

Gly Pro Gln Gly Val Val Gly Ala Asp Gly Lys Asp Gly Thr Pro Gly
1               5                   10                  15

Glu Lys Gly Glu Gln Gly Arg Thr Gly Ala Ala Gly Lys Gln Gly Ser
            20                  25                  30

Pro Gly Ala Asp Gly Ala Arg Gly Pro Leu Gly Ser Ile Gly Gln Gln
        35                  40                  45

Gly Ala Arg Gly Glu Pro Gly Asp Pro Gly Ser Pro Gly Leu Arg Gly
    50                  55                  60
```

```
Asp Thr Gly Leu Ala Gly Val Lys Gly Val Ala Gly Pro Ser Gly Arg
65                  70                  75                  80

Pro Gly Gln Pro Gly Ala Asn Gly Leu Pro Gly Val Asn Gly Arg Gly
                85                  90                  95

Gly Leu Arg Gly Lys Pro Gly Ala Lys Gly Ile Ala Gly Ser Asp Gly
            100                 105                 110

Glu Ala Gly Glu Ser Gly Ala Pro Gly Gln Ser Gly Pro Thr Gly Pro
        115                 120                 125

Arg Gly Gln Arg Gly Pro Ser Gly Glu Asp Gly Asn Pro Gly Leu Gln
    130                 135                 140

Gly Leu Pro Gly Ser Asp Gly Glu Pro Gly Glu Glu Gly Gln Pro Gly
145                 150                 155                 160

Arg Ser Gly Gln Pro Gly Gln Gln Gly Pro Arg Gly Ser Pro Gly Glu
                165                 170                 175

Val Gly Pro Arg Gly Ser Lys Gly Pro Ser Gly Asp Arg Gly Asp Arg
            180                 185                 190

Gly Glu Arg Gly Val Pro Gly Gln Thr Gly Ser Ala Gly Asn Val Gly
        195                 200                 205

Glu Asp Gly Glu Gln Gly Gly Lys Gly Val Asp Gly Ala Ser Gly Pro
    210                 215                 220

Ser Gly Ala Leu Gly Ala Arg Gly Pro Pro Gly Ser Arg Gly Asp Thr
225                 230                 235                 240

Gly Ala Val Gly Pro Pro Gly Pro Thr Gly Arg Ser Gly Leu Pro Gly
                245                 250                 255

Asn Ala Gly Gln Lys Gly Pro Ser Gly Glu Pro Gly Ser Pro Gly Lys
            260                 265                 270

Ala Gly Ser Ala Gly Glu Gln Gly Pro Pro Gly Lys Asp Gly Ser Asn
        275                 280                 285

Gly Glu Pro Gly Ser Pro Gly Lys Glu Gly Glu Arg Gly Leu Ala Gly
    290                 295                 300

Pro Pro Gly Pro Asp Gly Arg Arg Gly Glu Thr Gly Ser Pro Gly Ile
305                 310                 315                 320

Ala Gly Ala Leu Gly Lys Pro Gly Leu Glu Gly Pro Lys Gly Tyr Pro
                325                 330                 335

Gly Leu Arg Gly Arg Asp Gly Thr Asn Gly Lys Arg Gly Glu Gln Gly
            340                 345                 350

Glu Thr Gly Pro Asp Gly Val Arg Gly Ile Pro Gly Asn Asp Gly Gln
        355                 360                 365

Ser Gly Lys Pro Gly Ile Asp Gly Ile Asp Gly Thr Asn Gly Gln Pro
    370                 375                 380

Gly Glu Ala Gly Tyr Gln Gly Gly Arg Gly Thr Arg Gly Gln Leu Gly
385                 390                 395                 400

Glu Thr Gly Asp Val Gly Gln Asn Gly Asp Arg Gly Ala Pro Gly Pro
                405                 410                 415

Asp Gly Ser Lys Gly Ser Ala Gly Arg Pro Gly Leu Arg
            420                 425
```

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic His tag
<220> FEATURE:

```
<221> NAME/KEY: MISC_FEATURE
<222> LOCATION: (1)..(30)
<223> OTHER INFORMATION: This sequence may encompass 2-30 residues

<400> SEQUENCE: 34

His His His His His His His His His His His His His His His His
1               5                   10                  15

His His His His His His His His His His His His His His
            20                  25                  30


<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(20)
<223> OTHER INFORMATION: This sequence may encompass 2-20 residues

<400> SEQUENCE: 35

His His His His His His His His His His His His His His His His
1               5                   10                  15

His His His His
            20


<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 36

His His His His His His His His His His His His His His His
1               5                   10                  15


<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(18)
<223> OTHER INFORMATION: This sequence may encompass 5-18 residues

<400> SEQUENCE: 37

His His His His His His His His His His His His His His His His
1               5                   10                  15

His His


<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      His tag
```

<220> FEATURE:
<221> NAME/KEY: MISC_FEATURE
<222> LOCATION: (1)..(16)
<223> OTHER INFORMATION: This sequence may encompass 5-16 residues

<400> SEQUENCE: 38

His His His His His His His His His His His His His His His His
1               5                   10                  15

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(14)
<223> OTHER INFORMATION: This sequence may encompass 5-14 residues

<400> SEQUENCE: 39

His His His His His His His His His His His His His His
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(13)
<223> OTHER INFORMATION: This sequence may encompass 5-13 residues

<400> SEQUENCE: 40

His His His His His His His His His His His His His
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(12)
<223> OTHER INFORMATION: This sequence may encompass 5-12 residues

<400> SEQUENCE: 41

His His His His His His His His His His His His
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
His tag
<220> FEATURE:
<221> NAME/KEY: MISC_FEATURE
<222> LOCATION: (1)..(11)
<223> OTHER INFORMATION: This sequence may encompass 5-11 residues

<400> SEQUENCE: 42

```
His His His His His His His His His His His
1               5                   10


<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 43

His His His His His His His His His His
1               5                   10


<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(12)
<223> OTHER INFORMATION: This sequence may encompass 6-12 residues

<400> SEQUENCE: 44

His His His His His His His His His His His His
1               5                   10


<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(11)
<223> OTHER INFORMATION: This sequence may encompass 6-11 residues

<400> SEQUENCE: 45

His His His His His His His His His His His
1               5                   10


<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(10)
<223> OTHER INFORMATION: This sequence may encompass 7-10 residues

<400> SEQUENCE: 46

His His His His His His His His His His
1               5                   10


<210> SEQ ID NO 47
<211> LENGTH: 9
<212> TYPE: PRT
```

-continued

```
<213> ORGANISM: Artificial Sequence
<220> FEATURE:
<223> OTHER INFORMATION: Description of Artificial Sequence: Synthetic
      His tag

<400> SEQUENCE: 47

His His His His His His His His His
1               5
```